United States Patent
Shadduck

(10) Patent No.: US 10,675,079 B2
(45) Date of Patent: *Jun. 9, 2020

(54) METHOD FOR TREATING TISSUE

(71) Applicant: Tsunami MedTech, LLC, Menlo Park, CA (US)

(72) Inventor: John H. Shadduck, Menlo Park, CA (US)

(73) Assignee: Tsunami MedTech, LLC, Menlo Park, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/374,030

(22) Filed: Apr. 3, 2019

(65) Prior Publication Data

US 2019/0223934 A1 Jul. 25, 2019

Related U.S. Application Data

(60) Division of application No. 14/018,379, filed on Sep. 4, 2013, now abandoned, which is a continuation of
(Continued)

(51) Int. Cl.
*A61B 18/04* (2006.01)
*A61B 18/18* (2006.01)
(Continued)

(52) U.S. Cl.
CPC .............. *A61B 18/04* (2013.01); *A61B 18/18* (2013.01); *A61B 18/1815* (2013.01);
(Continued)

(58) Field of Classification Search
CPC ..... A61B 18/04; A61B 18/18; A61B 18/1815; A61B 18/20; A61B 2018/00619;
(Continued)

(56) References Cited

U.S. PATENT DOCUMENTS

| 408,899 A | 8/1889 | Bioch et al. |
| 697,181 A | 4/1902 | Smith |

(Continued)

FOREIGN PATENT DOCUMENTS

| WO | WO 2000/011927 | 3/2000 |
| WO | WO 2000/029055 | 5/2000 |

(Continued)

OTHER PUBLICATIONS

Coda, et al., "Effects of pulmonary reventilation on gas exchange after cryolytic disobstruction of endobronchial tumors," *Minerva Medical*, vol. 72, pp. 1627-1631, Jun. 1981 (with English translation).

(Continued)

*Primary Examiner* — Michael F Peffley
(74) *Attorney, Agent, or Firm* — Levine Bagade Han LLP

(57) ABSTRACT

This invention relates to a novel surgical device scalable to small dimensions for thermally-mediated treatments or thermoplasties of targeted tissue volumes. An exemplary embodiment is adapted for fusing, sealing or welding tissue. The instruments and techniques utilize a thermal energy delivery means, for example an electrical energy source, to instantly elevate the temperature of a biocompatible fluid media within an electrically insulated instrument portion. The altered media which may then be a gas is characterized by a (i) a high heat content, and (ii) a high exit velocity from the working end, both of which characteristics are controlled to hydrate tissue and at the same time denature proteins to fuse, seal, weld or cause any other thermally-mediated treatment of an engaged tissue volume—while causing limited collateral thermal damage and while totally eliminating electrical current flow the engaged tissue volume. The system can further utilize a piezoelectric material that carried fluid channels to apply compressive forces to the fluid (Continued)

eject the fluid from the working end of make it require less electrical energy to convert it to a gas.

9 Claims, 31 Drawing Sheets

Related U.S. Application Data application No. 12/258,145, filed on Oct. 24, 2008, now Pat. No. 8,574,226, which is a continuation-in-part of application No. 10/830,372, filed on Apr. 22, 2004, now Pat. No. 7,549,987, and a continuation-in-part of application No. 10/017,582, filed on Dec. 7, 2001, now Pat. No. 6,669,694, said application No. 10/830,372 is a continuation-in-part of application No. 10/681,625, filed on Oct. 7, 2003, now Pat. No. 7,674,259.

(60) Provisional application No. 60/464,935, filed on Apr. 22, 2003, provisional application No. 60/254,487, filed on Dec. 9, 2000, provisional application No. 60/416,622, filed on Oct. 7, 2002.

(51) Int. Cl.
  A61B 18/20 (2006.01)
  A61B 17/00 (2006.01)
  A61B 18/00 (2006.01)

(52) U.S. Cl.
  CPC ..... A61B 18/20 (2013.01); A61B 2017/00504 (2013.01); A61B 2018/0063 (2013.01); A61B 2018/00619 (2013.01); A61B 2018/048 (2013.01); A61B 2218/005 (2013.01)

(58) Field of Classification Search
  CPC ...... A61B 2018/0063; A61B 2018/048; A61B 2017/00504; A61B 2218/005
  See application file for complete search history.

(56) References Cited

U.S. PATENT DOCUMENTS

| | | |
|---|---|---|
| 1,719,750 A | 9/1927 | Bridge et al. |
| 3,818,913 A | 6/1974 | Wallach |
| 3,880,168 A | 4/1975 | Berman |
| 3,930,505 A | 1/1976 | Wallach |
| 4,024,866 A | 5/1977 | Wallach |
| 4,083,077 A | 4/1978 | Knight et al. |
| 4,672,962 A | 6/1987 | Hershenson |
| 4,682,596 A | 7/1987 | Bales et al. |
| 4,748,979 A | 6/1988 | Hershenson |
| 4,773,410 A | 9/1988 | Blackmer et al. |
| 4,793,352 A | 12/1988 | Eichenlaub |
| 4,872,920 A | 10/1989 | Flynn et al. |
| 4,898,574 A | 2/1990 | Uchiyama et al. |
| 4,915,113 A | 4/1990 | Holman |
| 4,950,266 A | 8/1990 | Sinofsky |
| 4,985,027 A | 1/1991 | Dressel |
| 5,006,119 A | 4/1991 | Acker et al. |
| 5,011,566 A | 4/1991 | Hoffman |
| 5,084,043 A | 1/1992 | Hertzmann et al. |
| 5,102,410 A | 4/1992 | Dressel |
| 5,112,328 A | 5/1992 | Taboada et al. |
| 5,122,138 A | 6/1992 | Manwaring |
| 5,158,536 A | 10/1992 | Sekins et al. |
| 5,190,539 A | 3/1993 | Fletcher et al. |
| 5,217,459 A | 6/1993 | Kamerling |
| 5,217,465 A | 6/1993 | Steppe |
| 5,263,951 A | 11/1993 | Spears et al. |
| 5,277,696 A | 1/1994 | Hagen |
| 5,298,298 A | 3/1994 | Hoffman |
| 5,318,014 A | 6/1994 | Carter |
| 5,331,947 A | 7/1994 | Shturman |
| 5,334,190 A | 8/1994 | Seiler |
| 5,348,551 A | 9/1994 | Spears et al. |
| 5,352,512 A | 10/1994 | Hoffman |
| 5,417,686 A | 5/1995 | Peterson et al. |
| 5,424,620 A | 6/1995 | Cheon et al. |
| 5,433,708 A | 7/1995 | Nichols et al. |
| 5,433,739 A | 7/1995 | Sluijter |
| 5,462,521 A | 10/1995 | Brucker et al. |
| 5,500,012 A | 3/1996 | Brucker et al. |
| 5,503,638 A | 4/1996 | Cooper et al. |
| 5,524,620 A | 6/1996 | Rosenschein |
| 5,529,076 A | 6/1996 | Schachar |
| 5,542,928 A * | 8/1996 | Evans ................ A61B 18/082 604/113 |
| 5,549,628 A | 8/1996 | Cooper et al. |
| 5,554,172 A | 9/1996 | Horner et al. |
| 5,562,608 A | 10/1996 | Sekins et al. |
| 5,575,803 A | 11/1996 | Cooper et al. |
| 5,584,872 A | 12/1996 | LaFontaine et al. |
| 5,591,157 A | 1/1997 | Hennings et al. |
| 5,591,162 A | 1/1997 | Fletcher et al. |
| 5,616,120 A | 4/1997 | Andrew et al. |
| 5,620,440 A | 4/1997 | Heckele et al. |
| 5,669,907 A | 9/1997 | Platt, Jr. et al. |
| 5,681,282 A | 10/1997 | Eggers et al. |
| 5,683,366 A | 11/1997 | Eggers et al. |
| 5,695,507 A | 12/1997 | Auth et al. |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,700,262 A | 12/1997 | Acosta et al. |
| 5,707,352 A | 1/1998 | Sekins et al. |
| 5,735,811 A | 4/1998 | Brisken |
| 5,741,247 A | 4/1998 | Rizoiu et al. |
| 5,741,248 A | 4/1998 | Stern et al. |
| 5,752,965 A | 5/1998 | Francis et al. |
| 5,755,753 A | 5/1998 | Knowlton |
| 5,782,914 A | 7/1998 | Schankereli |
| 5,785,521 A | 7/1998 | Rizoiu et al. |
| 5,800,482 A | 9/1998 | Pomeranz et al. |
| 5,810,764 A | 9/1998 | Eggers et al. |
| 5,824,703 A | 10/1998 | Clark, Jr. |
| 5,827,268 A | 10/1998 | Laufer |
| 5,843,019 A | 12/1998 | Eggers et al. |
| 5,843,073 A | 12/1998 | Sinofsky |
| 5,871,469 A | 2/1999 | Eggers et al. |
| 5,879,329 A | 3/1999 | Ginsburg |
| 5,885,243 A | 3/1999 | Capetan et al. |
| 5,888,198 A | 3/1999 | Eggers et al. |
| 5,891,095 A | 4/1999 | Eggers et al. |
| 5,891,134 A | 4/1999 | Goble et al. |
| 5,913,856 A | 6/1999 | Chia et al. |
| 5,944,686 A | 8/1999 | Patterson et al. |
| 5,944,715 A | 8/1999 | Goble et al. |
| 5,957,919 A | 9/1999 | Laufer |
| 5,964,752 A * | 10/1999 | Stone .................. A61B 18/04 606/27 |
| 5,968,037 A | 10/1999 | Rizoiu |
| 5,980,504 A | 11/1999 | Sharkey et al. |
| 5,986,662 A | 11/1999 | Argiro et al. |
| 5,989,212 A | 11/1999 | Sussman et al. |
| 5,989,238 A | 11/1999 | Ginsburg |
| 5,989,249 A | 11/1999 | Kirwin |
| 5,989,445 A | 11/1999 | Wise et al. |
| 5,997,499 A | 12/1999 | Sussman et al. |
| 6,024,733 A | 2/2000 | Eggers et al. |
| 6,027,501 A | 2/2000 | Goble et al. |
| 6,032,077 A | 2/2000 | Pomeranz |
| 6,032,674 A | 3/2000 | Eggers et al. |
| 6,047,700 A | 4/2000 | Eggers et al. |
| 6,053,909 A | 4/2000 | Shadduck |
| 6,056,746 A | 5/2000 | Goble et al. |
| 6,059,011 A | 5/2000 | Giolo |
| 6,063,079 A | 5/2000 | Hovda et al. |
| 6,063,081 A | 5/2000 | Mulier et al. |
| 6,066,134 A | 5/2000 | Eggers et al. |
| 6,074,358 A | 6/2000 | Andrew et al. |

(56) References Cited

U.S. PATENT DOCUMENTS

| | | |
|---|---|---|
| 6,080,128 A | 6/2000 | Sussman et al. |
| 6,080,151 A | 6/2000 | Swartz et al. |
| 6,083,255 A | 7/2000 | Laufer et al. |
| 6,095,149 A | 8/2000 | Sharkey et al. |
| 6,099,251 A | 8/2000 | LaFleur |
| 6,102,046 A | 8/2000 | Weinstein et al. |
| 6,102,885 A | 8/2000 | Bass |
| 6,106,516 A | 8/2000 | Bmassengill |
| 6,110,162 A | 8/2000 | Sussman et al. |
| 6,113,722 A | 9/2000 | Hoffman et al. |
| 6,126,682 A | 10/2000 | Sharkey et al. |
| 6,130,671 A | 10/2000 | Argiro |
| 6,139,571 A | 10/2000 | Fuller et al. |
| 6,149,620 A | 11/2000 | Baker et al. |
| 6,156,036 A | 12/2000 | Sussman et al. |
| 6,159,194 A | 12/2000 | Eggers et al. |
| 6,162,232 A | 12/2000 | Shadduck |
| 6,168,594 B1 | 1/2001 | LaFontaine et al. |
| 6,174,308 B1 | 1/2001 | Goble et al. |
| 6,179,805 B1 | 1/2001 | Sussman et al. |
| 6,190,381 B1 | 2/2001 | Olsen et al. |
| 6,194,066 B1 | 2/2001 | Hoffman |
| 6,196,989 B1 | 3/2001 | Padget et al. |
| 6,200,333 B1 | 3/2001 | Laufer |
| 6,206,848 B1 | 3/2001 | Sussman et al. |
| 6,210,404 B1 | 4/2001 | Shadduck |
| 6,210,405 B1 | 4/2001 | Goble et al. |
| 6,219,059 B1 | 4/2001 | Argiro |
| 6,224,592 B1 | 5/2001 | Eggers et al. |
| 6,231,567 B1 | 5/2001 | Rizoiu et al. |
| 6,235,020 B1 | 5/2001 | Cheng et al. |
| 6,238,391 B1 | 5/2001 | Olsen et al. |
| 6,254,597 B1 | 7/2001 | Rizoiu et al. |
| 6,261,286 B1 | 7/2001 | Goble et al. |
| 6,261,311 B1 | 7/2001 | Sharkey et al. |
| 6,264,650 B1 | 7/2001 | Hovda et al. |
| 6,264,651 B1 | 7/2001 | Underwood et al. |
| 6,264,654 B1 | 7/2001 | Swartz et al. |
| 6,277,112 B1 | 8/2001 | Underwood et al. |
| 6,283,961 B1 | 9/2001 | Underwood et al. |
| 6,283,989 B1 | 9/2001 | Laufer et al. |
| 6,287,274 B1 | 9/2001 | Sussman et al. |
| 6,290,715 B1 | 9/2001 | Sharkey et al. |
| 6,296,636 B1 | 10/2001 | Cheng et al. |
| 6,296,638 B1 | 10/2001 | Davidson et al. |
| 6,299,633 B1 | 10/2001 | Laufer |
| 6,300,150 B1 | 10/2001 | Venkatasubramanian |
| 6,312,408 B1 | 11/2001 | Eggers et al. |
| 6,312,474 B1 | 11/2001 | Francis et al. |
| 6,315,755 B1 | 11/2001 | Sussman |
| 6,319,222 B1 | 11/2001 | Andrew et al. |
| 6,327,505 B1 * | 12/2001 | Medhkour ......... A61B 18/1492 604/114 |
| 6,331,171 B1 | 12/2001 | Cohen |
| 6,355,032 B1 | 3/2002 | Hovda et al. |
| 6,375,635 B1 | 4/2002 | Moutafis et al. |
| 6,379,350 B1 | 4/2002 | Sharkey et al. |
| 6,391,025 B1 | 5/2002 | Weinstein et al. |
| 6,394,949 B1 | 5/2002 | Crowley et al. |
| 6,394,996 B1 | 5/2002 | Lawrence et al. |
| 6,398,759 B1 | 6/2002 | Sussman et al. |
| 6,398,775 B1 | 6/2002 | Perkins et al. |
| 6,409,723 B1 | 6/2002 | Edwards |
| 6,416,508 B1 | 7/2002 | Eggers et al. |
| 6,458,231 B1 | 10/2002 | Wapner et al. |
| 6,461,350 B1 | 10/2002 | Underwood et al. |
| 6,464,694 B1 | 10/2002 | Massengil |
| 6,464,695 B2 | 10/2002 | Hovda et al. |
| 6,468,270 B1 | 10/2002 | Hovda et al. |
| 6,468,274 B1 | 10/2002 | Alleyne et al. |
| 6,468,313 B1 | 10/2002 | Claeson et al. |
| 6,482,201 B1 | 11/2002 | Olsen et al. |
| 6,482,202 B1 | 11/2002 | Goble et al. |
| 6,488,673 B1 | 12/2002 | Laufer et al. |
| 6,493,589 B1 | 12/2002 | Medhkour et al. |
| 6,500,173 B2 | 12/2002 | Underwood et al. |
| 6,508,816 B2 | 1/2003 | Shadduck |
| 6,517,568 B1 | 2/2003 | Sharkey et al. |
| 6,522,930 B1 | 2/2003 | Schaer et al. |
| 6,527,761 B1 | 3/2003 | Soltesz et al. |
| 6,527,766 B1 | 3/2003 | Bair |
| 6,540,741 B1 | 4/2003 | Underwood et al. |
| 6,544,211 B1 | 4/2003 | Andrew et al. |
| 6,544,248 B1 | 4/2003 | Bass |
| 6,547,810 B1 | 4/2003 | Sharkey et al. |
| 6,558,379 B1 | 5/2003 | Batchelor et al. |
| 6,575,929 B2 | 6/2003 | Sussman et al. |
| 6,575,968 B1 | 6/2003 | Eggers et al. |
| 6,579,270 B2 | 6/2003 | Sussman et al. |
| 6,582,423 B1 | 6/2003 | Thapliyal et al. |
| 6,585,639 B1 | 7/2003 | Kotmel et al. |
| 6,588,613 B1 | 7/2003 | Pechenik et al. |
| 6,589,201 B1 | 7/2003 | Sussman et al. |
| 6,589,204 B1 | 7/2003 | Sussman et al. |
| 6,592,594 B2 | 7/2003 | Rimbaugh et al. |
| 6,595,990 B1 | 7/2003 | Weinstein et al. |
| 6,599,311 B1 | 7/2003 | Biggs et al. |
| 6,602,248 B1 | 8/2003 | Sharps et al. |
| 6,605,087 B2 | 8/2003 | Swartz et al. |
| 6,610,043 B1 | 8/2003 | Ingenito |
| 6,620,130 B1 | 9/2003 | Ginsburg |
| 6,620,155 B2 | 9/2003 | Underwood et al. |
| 6,623,444 B2 | 9/2003 | Babaev |
| 6,632,193 B1 | 10/2003 | Davison et al. |
| 6,632,220 B1 | 10/2003 | Eggers et al. |
| 6,634,363 B1 | 10/2003 | Danek et al. |
| 6,648,847 B2 | 11/2003 | Sussman et al. |
| 6,652,594 B2 | 11/2003 | Francis et al. |
| 6,653,525 B2 | 11/2003 | Ingenito et al. |
| 6,659,106 B1 | 12/2003 | Hovda et al. |
| 6,669,685 B1 | 12/2003 | Rizoiu et al. |
| 6,669,694 B2 | 12/2003 | Shadduck |
| 6,676,628 B2 | 1/2004 | Sussman et al. |
| 6,676,629 B2 | 1/2004 | Andrew et al. |
| 6,679,264 B1 | 1/2004 | Deem et al. |
| 6,679,879 B2 | 1/2004 | Shadduck |
| 6,682,520 B2 | 1/2004 | Ingenito |
| 6,692,494 B1 | 2/2004 | Cooper et al. |
| 6,695,839 B2 | 2/2004 | Sharkey et al. |
| 6,699,212 B1 | 3/2004 | Kadziauskas et al. |
| 6,699,244 B2 | 3/2004 | Carranza et al. |
| 6,712,811 B2 | 3/2004 | Underwood et al. |
| 6,712,812 B2 | 3/2004 | Roschak et al. |
| 6,719,738 B2 | 4/2004 | Mehier |
| 6,719,754 B2 | 4/2004 | Underwood et al. |
| 6,723,064 B2 | 4/2004 | Babaev |
| 6,726,684 B1 | 4/2004 | Woloszko et al. |
| 6,726,708 B2 | 4/2004 | Lasheras |
| 6,746,447 B2 | 6/2004 | Davison et al. |
| 6,755,794 B2 | 6/2004 | Soukup |
| 6,758,846 B2 | 7/2004 | Goble et al. |
| 6,763,836 B2 | 7/2004 | Tasto et al. |
| 6,764,487 B2 | 7/2004 | Mulier et al. |
| 6,766,202 B2 | 7/2004 | Underwood et al. |
| 6,770,070 B1 | 8/2004 | Balbierz |
| 6,770,071 B2 | 8/2004 | Woloszko et al. |
| 6,772,012 B2 | 8/2004 | Ricart et al. |
| 6,776,765 B2 | 8/2004 | Soukup et al. |
| 6,780,180 B1 | 8/2004 | Goble et al. |
| 6,805,130 B2 | 10/2004 | Tasto et al. |
| 6,832,996 B2 | 12/2004 | Woloszko et al. |
| 6,837,884 B2 | 1/2005 | Woloszko |
| 6,837,888 B2 | 1/2005 | Ciarrocca et al. |
| 6,852,108 B2 | 2/2005 | Barry et al. |
| 6,860,847 B2 | 3/2005 | Alferness et al. |
| 6,860,868 B1 | 3/2005 | Sussman et al. |
| 6,875,194 B2 | 4/2005 | MacKool |
| 6,896,674 B1 | 5/2005 | Wolosko et al. |
| 6,896,675 B2 | 5/2005 | Leung et al. |
| 6,901,927 B2 | 6/2005 | Deem et al. |
| 6,904,909 B2 | 6/2005 | Andreas et al. |
| 6,907,881 B2 | 6/2005 | Suki et al. |
| 6,911,028 B2 | 6/2005 | Shadduck |
| 6,918,903 B2 | 7/2005 | Bass |

(56) References Cited

U.S. PATENT DOCUMENTS

| | | | |
|---|---|---|---|
| 6,921,385 B2 | 7/2005 | Clements et al. | |
| 6,929,640 B1 | 8/2005 | Underwood et al. | |
| 6,949,096 B2 | 9/2005 | Davison et al. | |
| 6,955,675 B2 | 10/2005 | Jain | |
| 6,960,182 B2 | 11/2005 | Moutafis et al. | |
| 6,972,014 B2 | 12/2005 | Eum et al. | |
| 6,986,769 B2 | 1/2006 | Nelson et al. | |
| 6,991,028 B2 | 1/2006 | Comeaux et al. | |
| 6,991,631 B2 | 1/2006 | Wolosko et al. | |
| 7,022,088 B2 | 4/2006 | Keast et al. | |
| 7,031,504 B1 | 4/2006 | Argiro et al. | |
| 7,083,612 B2 | 8/2006 | Littrup et al. | |
| 7,128,748 B2 | 10/2006 | Mooradian et al. | |
| 7,136,064 B2 | 11/2006 | Zuiderveld | |
| 7,144,402 B2 | 12/2006 | Kuester, III | |
| 7,144,588 B2 | 12/2006 | Oray et al. | |
| 7,192,400 B2 | 3/2007 | Campbell et al. | |
| 7,233,820 B2 | 6/2007 | Gilboa | |
| 7,235,070 B2 | 6/2007 | Vanney | |
| 7,335,195 B2 | 2/2008 | Mehier | |
| 7,347,859 B2 | 3/2008 | Garabedian et al. | |
| 7,549,987 B2 | 6/2009 | Shadduck | |
| 7,585,295 B2 | 9/2009 | Ben-Nun | |
| 7,674,259 B2 | 3/2010 | Shadduck | |
| 7,892,229 B2 | 2/2011 | Shadduck et al. | |
| 8,016,823 B2 | 9/2011 | Shadduck | |
| 8,574,226 B2 | 11/2013 | Shadduck | |
| 8,721,632 B2 * | 5/2014 | Hoey | A61B 18/18 604/113 |
| 8,758,341 B2 | 6/2014 | Shadduck | |
| 2001/0020167 A1 | 9/2001 | Woloszko et al. | |
| 2001/0029370 A1 | 10/2001 | Hodva et al. | |
| 2001/0037106 A1 | 11/2001 | Shadduck | |
| 2002/0049438 A1 | 4/2002 | Sharkey et al. | |
| 2002/0077516 A1 | 6/2002 | Flanigan | |
| 2002/0082667 A1 | 6/2002 | Shadduck | |
| 2002/0095152 A1 | 7/2002 | Ciarrocca et al. | |
| 2002/0111386 A1 | 8/2002 | Sekins et al. | |
| 2002/0128638 A1 | 9/2002 | Chauvet et al. | |
| 2002/0133147 A1 | 9/2002 | Marchitto et al. | |
| 2002/0161326 A1 | 10/2002 | Sussman et al. | |
| 2002/0177846 A1 | 11/2002 | Mulier et al. | |
| 2002/0193789 A1 | 12/2002 | Underwood et al. | |
| 2003/0028189 A1 | 2/2003 | Woloszko et al. | |
| 2003/0040742 A1 | 2/2003 | Underwood et al. | |
| 2003/0097126 A1 | 5/2003 | Woloszko et al. | |
| 2003/0099279 A1 | 5/2003 | Venkatasubramanian et al. | |
| 2003/0109869 A1 | 6/2003 | Shadduck | |
| 2003/0130655 A1 | 7/2003 | Woloszko et al. | |
| 2003/0130738 A1 | 7/2003 | Hovda et al. | |
| 2003/0158545 A1 | 8/2003 | Hovda et al. | |
| 2003/0163178 A1 | 8/2003 | Davison et al. | |
| 2003/0181922 A1 | 9/2003 | Alferness | |
| 2003/0212394 A1 | 11/2003 | Pearson et al. | |
| 2003/0212395 A1 | 11/2003 | Woloszko et al. | |
| 2003/0225364 A1 | 12/2003 | Kraft et al. | |
| 2004/0024398 A1 | 2/2004 | Hovda et al. | |
| 2004/0024399 A1 | 2/2004 | Sharps et al. | |
| 2004/0031494 A1 | 2/2004 | Danek et al. | |
| 2004/0038868 A1 | 2/2004 | Ingenito | |
| 2004/0047855 A1 | 3/2004 | Ingenito | |
| 2004/0049180 A1 | 3/2004 | Sharps et al. | |
| 2004/0054366 A1 | 3/2004 | Davison et al. | |
| 2004/0055606 A1 | 3/2004 | Hendricksen et al. | |
| 2004/0068256 A1 | 4/2004 | Rizoiu et al. | |
| 2004/0068306 A1 | 4/2004 | Shadduck | |
| 2004/0087937 A1 | 5/2004 | Eggers et al. | |
| 2004/0116922 A1 | 6/2004 | Hovda et al. | |
| 2004/0193150 A1 | 9/2004 | Sharkey et al. | |
| 2004/0199226 A1 | 10/2004 | Shadduck | |
| 2004/0230190 A1 | 11/2004 | Dahla et al. | |
| 2004/0254532 A1 | 12/2004 | Mehier | |
| 2005/0004634 A1 | 1/2005 | Ricart et al. | |
| 2005/0010205 A1 | 1/2005 | Hovda et al. | |
| 2005/0119650 A1 | 6/2005 | Sanders et al. | |
| 2005/0166925 A1 | 8/2005 | Wilson et al. | |
| 2005/0171582 A1 | 8/2005 | Matlock | |
| 2005/0187543 A1 | 8/2005 | Underwood et al. | |
| 2005/0215991 A1 | 9/2005 | Altman et al. | |
| 2005/0222485 A1 | 10/2005 | Shaw et al. | |
| 2005/0228423 A1 | 10/2005 | Khashayar et al. | |
| 2005/0228424 A1 | 10/2005 | Khashayar et al. | |
| 2005/0240171 A1 | 10/2005 | Forrest | |
| 2005/0267467 A1 | 12/2005 | Paul et al. | |
| 2005/0283143 A1 | 12/2005 | Rizoiu | |
| 2006/0004400 A1 | 1/2006 | McGurk et al. | |
| 2006/0047291 A1 | 3/2006 | Barry | |
| 2006/0085054 A1 | 4/2006 | Zikorus et al. | |
| 2006/0100619 A1 | 5/2006 | McClurken et al. | |
| 2006/0130830 A1 | 6/2006 | Barry | |
| 2006/0135955 A1 | 6/2006 | Shadduck | |
| 2006/0161233 A1 | 7/2006 | Barry et al. | |
| 2006/0200076 A1 | 9/2006 | Gonzalez et al. | |
| 2006/0224154 A1 | 10/2006 | Shadduck et al. | |
| 2007/0036417 A1 | 2/2007 | Argiro et al. | |
| 2007/0091087 A1 | 4/2007 | Zuiderveld | |
| 2008/0033493 A1 | 2/2008 | Deckman et al. | |
| 2008/0103566 A1 | 5/2008 | Mehier | |
| 2008/0110457 A1 | 5/2008 | Barry et al. | |
| 2008/0114297 A1 | 5/2008 | Barry et al. | |
| 2008/0132826 A1 | 6/2008 | Shadduck et al. | |
| 2009/0105702 A1 | 4/2009 | Shadduck | |
| 2009/0105703 A1 | 4/2009 | Shadduck | |
| 2009/0149846 A1 | 6/2009 | Hoey et al. | |
| 2009/0216220 A1 | 8/2009 | Hoey et al. | |
| 2009/0312753 A1 | 12/2009 | Shadduck | |
| 2010/0076416 A1 | 3/2010 | Hoey et al. | |
| 2010/0160905 A1 | 6/2010 | Shadduck | |
| 2010/0204688 A1 | 8/2010 | Hoey et al. | |
| 2010/0262133 A1 | 10/2010 | Hoey et al. | |
| 2011/0077628 A1 | 3/2011 | Hoey et al. | |
| 2011/0118717 A1 | 5/2011 | Shadduck | |
| 2011/0160648 A1 | 6/2011 | Hoey | |
| 2011/0264090 A1 | 10/2011 | Shadduck et al. | |
| 2012/0065632 A1 | 3/2012 | Shadduck | |
| 2012/0259271 A1 | 10/2012 | Shadduck et al. | |
| 2014/0031805 A1 | 1/2014 | Shadduck | |

FOREIGN PATENT DOCUMENTS

| | | |
|---|---|---|
| WO | WO 2002/069821 | 9/2002 |
| WO | WO 2003/070302 | 8/2003 |
| WO | WO 2003/086498 | 10/2003 |
| WO | WO 2005/025635 | 3/2005 |
| WO | WO 2005/102175 | 11/2005 |
| WO | WO 2006/003665 | 1/2006 |
| WO | WO 2006/055695 | 5/2006 |
| WO | WO 2009/009398 | 1/2009 |

OTHER PUBLICATIONS

Fishman et al., "A randomized trial comparing lung-volume-reduction surgery with medical therapy for severe emphysema," *N Engl J Med*, vol. 348, No. 21, pp. 2059-2073, May 22, 2003.

Homasson, et al., "Bronchoscopic cryotherapy for airway strictures caused by tumors," *Chest*, vol. 90, No. 2, pp. 159-164, Aug. 1, 1986.

Li, K., "Efficient optimal net surface detection for image segmentation—from theory to practice," M.Sc. Thesis, The University of Iowa, 2003.

Marasso, et al., "Cryosurgery in bronchoscopic treatment of tracheobronchial stenosis," *Chest*, vol. 103, No. 2, pp. 472-474, Feb. 1993.

Marasso, et al., "Radiofrequency resection of bronchial tumours in combination with cryotherapy: evaluation of a new technique," *Thorax*, vol. 53, pp. 106-109, 1998.

Mathur et al., "Fiberoptic bronchoscopic cryotherapy in the management of tracheobronchial obstruction," *Chest*, vol. 110, No. 3, pp. 718-723, Sep. 1996.

Morice et al. "Endobrinchial argon plasma coagulation for treatment of hemotysis and neoplastic airway obstruction," *Chest*, vol. 119, No. 3, pp. 781-787, Mar. 1, 2001.

(56) References Cited

OTHER PUBLICATIONS

Moulding et al., "Preliminary studies for achieving transcervical oviduct occlusion by hot water or low-pressure steam," *Advancesin Planned Parenthood*, vol. 12, No. 2; pp. 79-85, 1977.
Quin, J., "Use of neodymium yttrium aluminum garnet laser in long-term palliation of airway obstruction," *Connecticut Medicine*, vol. 59, No. 7, pp. 407-412, Jul. 1995.
Sutedja, et al., "Bronchoscopic treatment of lung tumors," *Elsevier, Lung Cancer*, 11, pp. 1-17, 1994.
Tschirren et al.; "Intrathoracic airway trees: segmentation and airway morphology analysis from low-dose CT scans;" *IEEE Trans. Med. Imaging*, vol. 24, No. 12; pp. 1529-1539, Dec. 2005.
Tschirren, J., "Segmentation, anatomical labeling, branchpoint matching, and quantitative analysis of human airway trees in volumetric CT images," Ph.D. Thesis, The University of Iowa, 231 pages, Aug. 2003.
Tschirren, J., "Segmentation, anatomical labeling, branchpoint matching, and quantitative analysis of human airway trees in volumetric CT images," Slides from Ph.D. defense, University of Iowa, 130 pages, Aug. 2003.
Unger, M. et al. "Monolithic Microfabricated Valves and Pumps by Multilayer Soft Lithography," *Science*, vol. 288, pp. 113-116, Apr. 7, 2000, accessed at http://web.mit.edu/thorsen/www/113.pdf.
Xia, Y. et al. "Soft Lithography," *Annu. Rev. Mater. Sci.*, vol. 28, pp. 153-184, 1998, accessed at http://www.bwfoundry.com/xia.pdf.

\* cited by examiner

METHOD FOR TREATING TISSUE

CROSS-REFERENCE TO RELATED APPLICATIONS

This application is a divisional of U.S. patent application Ser. No. 14/018,379 filed Sep. 4, 2013, now abandoned, which is a continuation of U.S. patent application Ser. No. 12/258,145 filed Oct. 24, 2008, now U.S. Pat. No. 8,574,226, which is a continuation-in-part of U.S. patent application Ser. No. 10/830,372 filed on Apr. 22, 2004, now U.S. Pat. No. 7,549,987, which claims the benefit of U.S. Provisional Application No. 60/464,935 filed Apr. 22, 2003, and is a continuation-in-part of U.S. patent application Ser. No. 10/017,582 filed Dec. 7, 2001, now U.S. Pat. No. 6,669,694, which claims benefit of Provisional U.S. Patent Application No. 60/254,487 filed Dec. 9, 2000. U.S. patent application Ser. No. 10/830,372 is also a continuation-in-part of U.S. patent application Ser. No. 10/681,625 filed Oct. 7, 2003, now U.S. Pat. No. 7,674,259, which claims the benefit of Provisional U.S. Patent Application No. 60/416,622 filed Oct. 7, 2002. The contents of the above applications are incorporated herein by reference in their entirety.

BACKGROUND OF THE INVENTION

This invention relates to a novel surgical device scalable to small dimensions for thermally-mediated treatments or thermoplasties of targeted tissue volumes. An exemplary embodiment is adapted for fusing, sealing or welding tissue. The instrument and technique utilizes electrical energy to instantly convert a biocompatible fluid media to a superheated media, perhaps a gas media, within an electrically insulated instrument working end. The altered media is characterized by a (i) a high heat content, and (ii) a high exit velocity from the working end, both of which characteristics are controlled to hydrate tissue and at the same time denature proteins to fuse, seal, weld or cause any other thermally-mediated treatment of an engaged tissue volume—while causing limited collateral thermal damage and while totally eliminating electrical current flow the engaged tissue volume.

Laser and Rf energy applications cause thermal effects in tissue based on different principles. In general, the non-linear or non-uniform characteristics of tissue affect both laser and Rf energy distributions in tissue. For example, FIG. 1A shows a typical pattern of energy distribution and resultant thermal effects in a prior art laser irradiation of tissue. The cross-section of the energy emitter or emission is indicated at ee at the tissue interface wherein a fiber optic interfaces tissue of a light beam strikes the tissue. In the case of a suitable infrared laser emission, water in tissue comprises a chromophore to absorb photonic energy resulting in a thermal effect. The turbidity of tissue scatters photons, and the resulting thermal effect is indicated by arbitrary isotherms 100, 80 and 60 which for example indicate degrees in centigrade. FIG. 1A shows that tissue desiccation d at the surface will occur to prevent photon transmission after a certain interval of energy delivery. If the objective of the thermal therapy in FIG. 1A were to seal or weld tissue, which is assumed to require a threshold temperature of 80° C., it can be seen that deeper tissue indicated at b may not reach the threshold welding temperature before the tissue surface is desiccated. Further, it can be seen that collateral tissue indicated at c may be sealed or welded, even though such tissue is collateral to the cross-section of the energy emission ee.

FIG. 1B next shows a typical energy distribution pattern when using a prior art bi-polar Rf energy delivery. In this schematic illustration, the cross-section of the energy emitter is again indicated at ee which defines the interface between a tissue surface and the electrodes 4a and 4b. As the electrodes are energized from an electrical source, the current flows are in constant flux and flow through random paths of least resistant between the electrodes. The tissue is elevated in temperature by it resistance to current flow, resulting typically in tissue desiccation or charring d at the electrode-tissue interface. When tissue in contact with the electrode is entirely desiccated, the current flow between the electrodes terminates. As represented in FIG. 1B, thermal effects typically occur in regions of tissue (indicated at c) collateral to the targeted tissue between the electrodes. Further, the prior art Rf energy delivery of FIG. 1B causes stray Rf flow in collateral tissues that may be undesirable.

What is needed is an instrument and technique (i) that can controllably deliver thermal energy to non-uniform tissue volumes; (i) that can weld tissue without desiccation or charring of surface tissue layers; (iii) that can weld a targeted tissue volume while preventing collateral thermal damage; and (iv) that does not cause stray Rf current flow in tissue.

This invention additionally relates to the working end of a medical instrument that applies energy to tissue from a fluid within a microfluidic tissue-engaging surface fabricated by soft lithography means together with optional superlattice cooling means that allows for very precise control of energy application, for example in neurosurgery applications.

Various types of radiofrequency (Rf) and laser surgical instruments have been developed for delivering thermal energy to tissue, for example to cause hemostasis, to weld tissue or to cause a thermoplastic remodeling of tissue. While such prior art forms of energy delivery work well for some applications, Rf and laser energy typically cannot cause highly "controlled" and "localized" thermal effects that are desirable in microsurgeries or other precision surgeries. In general, the non-linear or non-uniform characteristics of tissue affect both laser and Rf energy distributions in tissue. The objective of sealing or welding tissue requires means for elevating the tissue temperature uniformly throughout a targeted site.

What is needed is an instrument and technique (i) that can controllably deliver thermal energy to non-uniform tissue volumes; (i) that can shrink, seal, weld or create lesions in selected tissue volumes without desiccation or charring of adjacent tissues; (iii); and (iv) that does not cause stray electrical current flow in tissue.

BRIEF SUMMARY OF THE INVENTION

The present invention is adapted to provide novel systems and techniques capable of controlled thermal energy delivery to localized tissue volumes, for example for sealing, welding or thermoplastic remodeling of tissue. Of particular interest, the system can create thermal welds or seals in a targeted tissue without the use of Rf current flow through the patient's body, which is typical in the prior art. The systems and techniques are particularly adapted for sealing or welding thick tissue and non-uniform tissue layers. The biological mechanisms underlying tissue fusion or welding are complex and is not fully understood Applications of laser and Rf energy can be used to elevate tissue temperatures to the level that causes denaturation of proteins, which is a first step in tissue fusion. The terms fuse, weld and seal are used interchangeably herein, which mean that a temperature-induced protein denaturation process causes such proteins (particularly various types of collagen), water and other tissue constituents to meld into a proteinaceous amalgam. A form of thermal biological glue can occur at temperatures ranging from about 65° C. to 100° C. Upon the cooling of tissue and subsequent healing of the treated tissue, the tissue is fused together or welded as the damaged proteins re-nature in a part of the body's wound healing process.

The probe of the present invention has a working end that defines a tissue-contacting surface with a plurality of media entrance ports. A fluid media source is fluidly coupled to the media entrance ports by a fluid channel. Fluid vaporization comprising paired electrodes are carried within the channel for converting the fluid media from a first liquid state to a second gas state—i.e., a flash vaporization means. The instrument and technique thus utilize electrical energy to convert the biocompatible fluid media to a superheated gas media that has a high heat content that exits the ports at a high velocity into the targeted tissue.

In a further embodiment of the invention, the tissue-contacting surface may carry components of a sensor system which together with a power controller can control the intervals of electrical discharges during a thermotherapy. For example, feedback circuitry for measuring temperatures at one or more temperature sensors may be provided. The power controller can also modulate and control voltage of the discharge to alter media exit velocity, all in order to achieve (or maintain) a particular parameter such as a particular temperature in tissue, an average of temperatures measured among multiple sensors, or a temperature profile (change in energy delivery over time).

The instrument and method of the invention advantageously can cause thermal effects in tissue that do not rely applying an electrical field across the tissue to be treated.

The instrument and method of the invention advantageously can cause thermal effects in tissue that do not rely delivering high-intensity laser energy to the targeted tissue.

The instrument and method of the invention creates thermal effects in targeted tissue that without causing tissue desiccation or surface carbonization common to electrosurgical modalities and laser irradiation modalities.

The instrument and method of the invention advantageously creates thermal effects in a targeted tissue volume with substantially controlled lateral margins between the treated tissue and untreated tissue.

The instrument and method of the invention creates thermal effects in targeted tissues that caused stray electrical current flow in the patient's body.

The present invention is also adapted to provide improved methods of controlled thermal energy delivery to localized tissue volumes, for example for sealing, welding or thermoplastic remodeling of tissue. Of particular interest, the method causes thermal effects in targeted tissue without the use of Rf current flow through the patient's body.

In general, the thermally-mediated treatment method comprises causing a vapor-to-liquid phase state change in a selected media at a targeted tissue site thereby applying thermal energy substantially equal to the heat of vaporization of the selected media to said tissue site. The thermally-mediated therapy can be delivered to tissue by such vapor-to-liquid phase transitions, or "internal energy" releases, about the working surfaces of several types of instruments for endoluminal treatments or for soft tissue thermotherapies. FIGS. 2A and 2B illustrate the phenomena of phase transitional releases of internal energies. Such internal energy involves energy on the molecular and atomic scale—and in polyatomic gases is directly related to intermolecular attractive forces, as well as rotational and vibrational kinetic energy. In other words, the method of the invention exploits the phenomenon of internal energy transitions between gaseous and liquid phases that involve very large amounts of energy compared to specific heat.

It has been found that the controlled application of internal energies in an introduced media-tissue interaction solves many of the vexing problems associated with energy-tissue interactions in Rf, laser and ultrasound modalities. The apparatus of the invention provides a fluid-carrying chamber in the interior of the device or working end. A source provides liquid media to the interior chamber wherein energy is applied to instantly vaporize the media. In the process of the liquid-to-vapor phase transition of a saline media in the interior of the working end, large amounts of energy are added to overcome the cohesive forces between molecules in the liquid, and an additional amount of energy is requires to expand the liquid 1000+ percent (P$\Delta$D) into a resulting vapor phase (see FIG. 2A). Conversely, in the vapor-to-liquid transition, such energy will be released at the phase transitions at the targeted tissue interface. That is, the heat of vaporization is released in tissue when the media transitioning from gaseous phase to liquid phase wherein the random, disordered motion of molecules in the vapor regain cohesion to convert to a liquid media. This release of energy (defined as the capacity for doing work) relating to intermolecular attractive forces is transformed into therapeutic heat for a thermotherapy within a targeted body structure. Heat flow and work are both ways of transferring energy.

In FIG. 2A, the simplified visualization of internal energy is useful for understanding phase transition phenomena that involve internal energy transitions between liquid and vapor phases. If heat were added at a constant rate in FIG. 2A (graphically represented as 5 calories/gm blocks) to elevate the temperature of water through its phase change to a vapor phase, the additional energy required to achieve the phase change (latent heat of vaporization) is represented by the large number of 110+ blocks of energy at 100° C. in FIG. 2A. Still referring to FIG. 2A, it can be easily understood that all other prior art ablation modalities—Rf, laser, microwave and ultrasound—create energy densities by simply ramping up calories/gm as indicated by the temperature range from 37° C. through 100° C. as in FIG. 2A. The prior art modalities make no use of the phenomenon of phase transition energies as depicted in FIG. 2A.

FIG. 2B graphically represents a block diagram relating to energy delivery aspects of the present invention. The system provides for insulative containment of an initial primary energy-media within an interior chamber of an instrument's working end. The initial, ascendant energy-media interaction delivers energy sufficient to achieve the heat of vaporization of a selected liquid media such as saline within an interior of the instrument body. This aspect of the technology requires an inventive energy source and controller—since energy application from the source to the selected media (Rf, laser, microwave, etc.) must be modulated between very large energy densities to initially surpass the latent heat of vaporization of the media within milliseconds, and possible subsequent lesser energy densities for maintaining the media in its vapor phase. Additionally, the energy delivery system is coupled to a pressure control system for replenishing the selected liquid phase media at the required rate—and optionally for controlling propagation velocity of the vapor phase media from the working end surface of the instrument. In use, the method of the invention comprises the controlled deposition of a large amount of energy—the heat of vaporization as in FIG. 2A—when the vapor-toliquid phase transition is controlled at the vapor media-tissue interface. The vapor-to-liquid phase transition can deposit as much as 580 cal/gram within the targeted tissue site to perform the thermal ablation.

This new ablation modality can utilize specialized instrument working ends for several cardiovascular therapies or soft tissue ablation treatments for tissue sealing, tissue shrinkage, tissue ablation, creation of lesions or volumetric removal of tissue. In general, the instrument and method of the invention advantageously cause thermal ablations rapidly and efficiently compared to conventional Rf energy application to tissue.

In one embodiment, the instrument of the invention provides a tissue engaging surface of a polymeric body that carries microfluidic channels therein. The tissue-engaging surfaces are fabricated by soft lithography means to provide the fluidic channels and optional conductive materials to function as electrodes.

In another embodiment, the instrument has a working end with a superlattice cooling component that cooperates with the delivery of energy. For example, in neurosurgery, the superlattice cooling can be used to allow a brief interval of thermal energy delivery to coagulate tissue followed by practically instantaneous cooling and renaturing of proteins in the coagulated tissue to allowing sealing and to prevent the possibility of collateral thermal damage. At the same time, the cooling means insures that tissue will not stick to a jaw structure. In a preferred embodiment, the invention utilizes a thermoelectric cooling system as disclosed by Rama Venkatasubramanian et al. in U.S. patent application Ser. No. 10/265,409 (Published Application No. 20030099279 published May 29, 2003) titled Phonon-blocking, electron-transmitting low-dimensional structures, which is incorporated herein by reference. The cooling system is sometimes referred to as a PBETS device, an acronym relating to the title of the patent application. The inventors (Venkatasubramanian et al) also disclosed related technologies in U.S. Pat. No. 6,300,150 titled Thin-film Thermoelectric Device and Fabrication Method of same, which is incorporated herein by reference.

In another embodiment, the instrument provides a tissue engaging surface with capillary dimension channels to draw a liquid into the channels wherein an energy emitter is used to eject vapor from the open ends of the capillaries.

The instrument and method of the invention advantageously creates thermal effects in a targeted tissue volume with substantially controlled lateral margins between the treated tissue and untreated tissue;

The instrument and method of the invention generate vapor phase media that is controllable as to volume and ejection pressure to provide a not-to-exceed temperature level that prevents desiccation, eschar, smoke and tissue sticking;

The instrument and method of the invention cause an energy-tissue interaction that is imageable with intraoperative ultrasound or MRI;

The instrument and method of the invention advantageously cause thermal effects in tissue that do not rely applying an electrical field across the tissue to be treated; and The instrument and method of the invention advantageously creates thermal effects in a targeted tissue volume with substantially controlled lateral margins between the treated tissue and untreated tissue.

Additional advantages of the invention will be apparent from the following description, the accompanying drawings and the appended claims.

BRIEF DESCRIPTION OF THE SEVERAL VIEWS OF THE DRAWINGS

Various embodiments of the present invention will be discussed with reference to the appended drawings. These drawings depict only illustrative embodiments of the invention and are not to be considered limiting of its scope.

FIG. 6A is a sectional illustration of the delivery of fluid or liquid media to an interior channel or the working end, and FIG. 6B depicting an electrical discharge that causes a liquid-to-gas phase change or that induces flash vaporization of the contained fluid as well as the ejection of the vapor media or a superheated gas into the targeted tissue to cause a thermal weld.

DETAILED DESCRIPTION OF THE INVENTION

1. Type "A" System for Tissue Fusion.

Figure 3A:
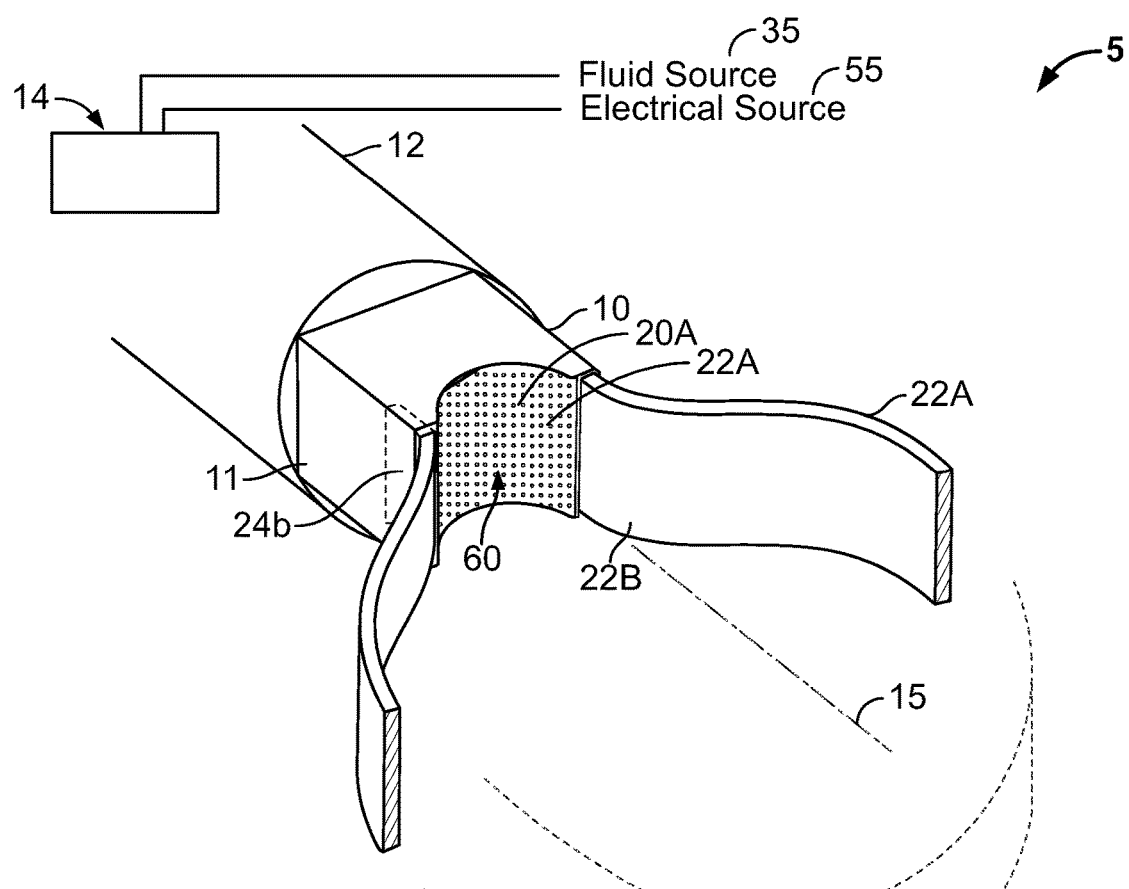
FIG. 3A is a perspective view of the working end of an exemplary Type "A" and/or "C" probe of the present invention with an openable-closeable tissue engaging structure in a first open position.
Figure 3B:
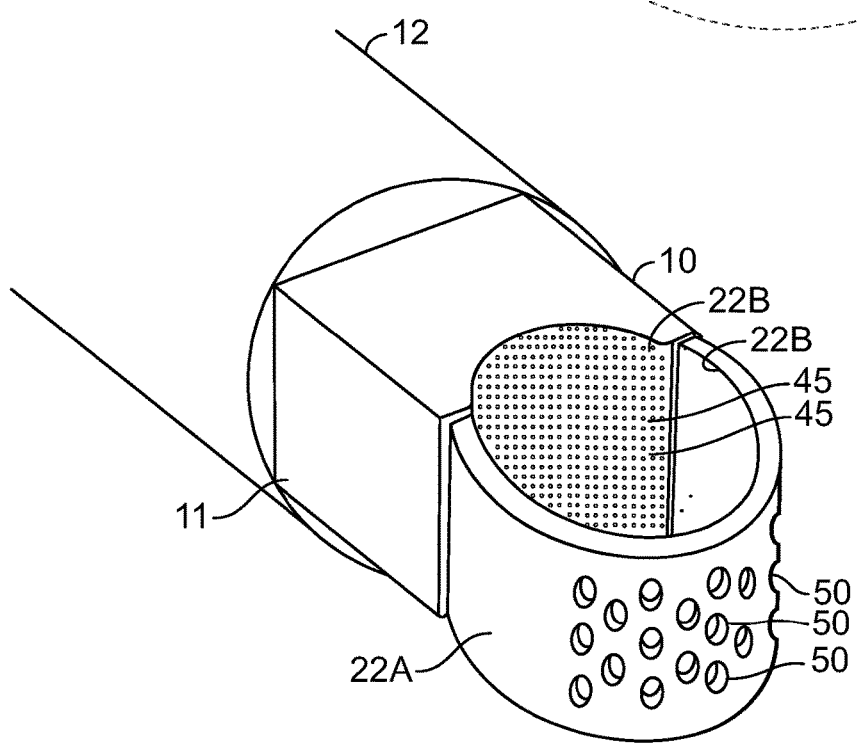
FIG. 3B is a perspective view similar to FIG. 3A probe of the present invention in a second closed position.
Figure 4:
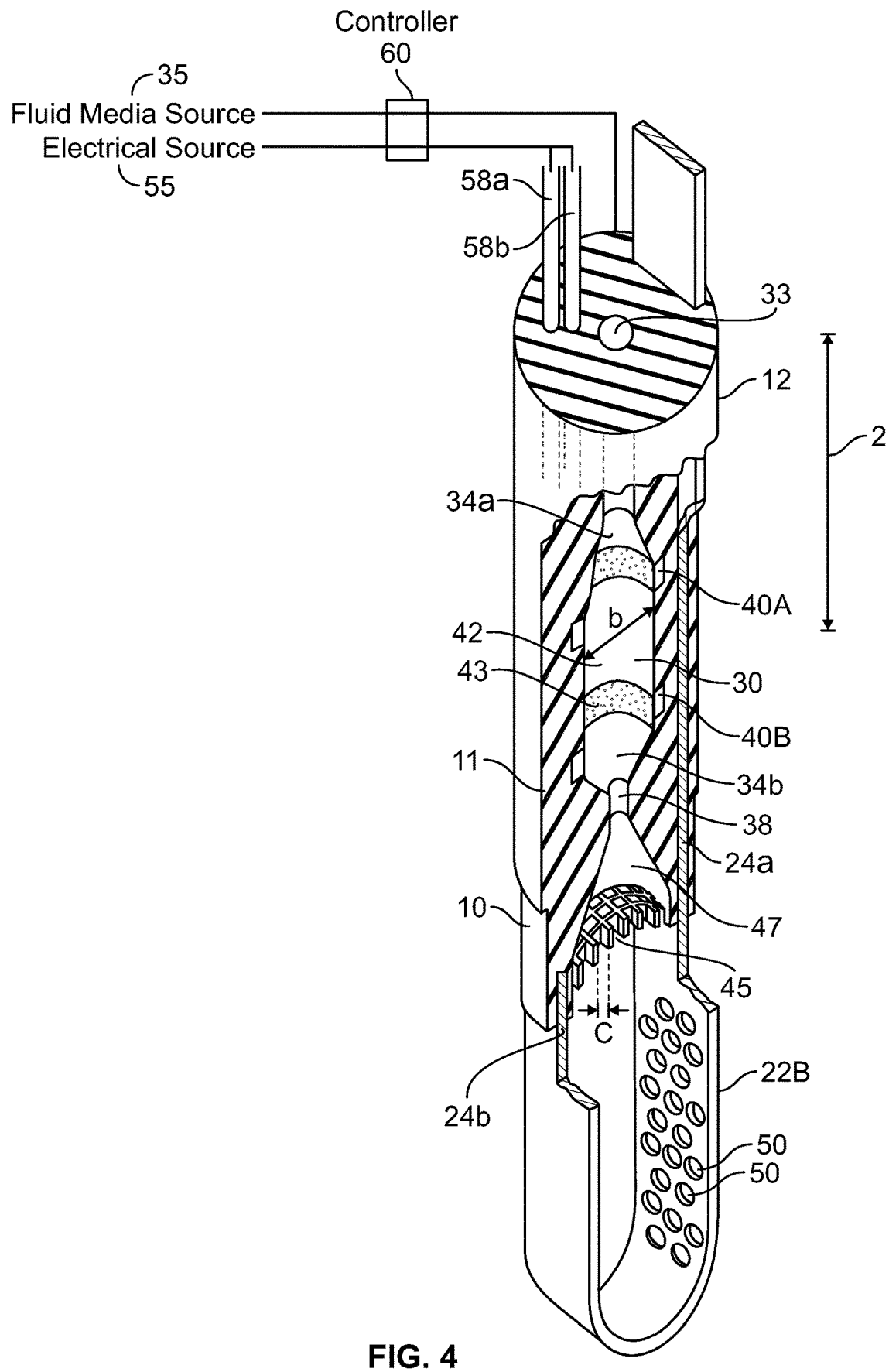
FIG. 4 is a cut-away view of the working end of FIGS. 3A-3B.

Referring to FIGS. 3A-3B and FIG. 4, the working end 10 of a Type "A" system 5 of the present invention is shown that is adapted for endoscopic procedures in which a tissue volume t targeted for fusion (a thermoplasty) can be captured by a loop structure. The working end 10 comprises a body 11 of insulator material (see FIG. 4) coupled to the distal end of introducer member 12 extending along axis 15. In this exemplary embodiment, the working end 10 has a generally cylindrical cross-section and is made of any suitable material such as plastic, ceramic, glass, metal or a combination thereof. The working end 10 is substantially small in diameter (e.g., 2 mm. to 5 mm.) and in this embodiment is coupled to an elongate flexible introducer member 12 to cooperate with a working channel in an endoscope. Alternatively, the working end 10 may be coupled to a rigid shaft member having a suitable 5 mm. to 10 mm. diameter to cooperate with a standard trocar sleeve for use in endoscopic procedures. A proximal handle portion 14 of the instrument indicated by the block diagram of FIG. 3A carries the various actuator mechanisms known in the art for actuating components of the instrument.

In FIGS. 3A-3B and 4, it can be seen that the working end 10 carries an openable and closeable structure for capturing tissue between a first tissue-engaging surface 20A and a second tissue-engaging surface 20B. In this exemplary embodiment, the working end 10 and first tissue-engaging surface 20A comprises a non-moving component indicated at 22A that is defined by the exposed distal end of body 11 of working end 10. The second tissue-engaging surface 20B is carried in a moving component that comprises a flexible loop structure indicated at 22B.

The second moving component or flexible loop 22B is actuatable by a slidable portion 24a of the loop that extends through a slot 25 in the working end to an actuator in the handle portion 14 as is known in the art (see FIG. 4). The other end 24b of the loop structure 22B is fixed in body 11. While such an in-line (or axial) flexible slidable member is preferred as the tissue-capturing mechanism for a small diameter flexible catheter-type instrument, it should be appreciated that any openable and closable jaw structure known in the art falls within the scope of the invention, including forms of paired jaws with cam-surface actuation or conventional pin-type hinges and actuator mechanisms. FIG. 3A illustrates the first and second tissue-engaging surfaces 20A and 20B in a first spaced apart or open position. FIG. 3B show the first and second surfaces 20A and 20B moved toward a second closed position.

Now turning to the fluid-to-gas energy delivery means of the invention, referring to FIG. 4, it can be seen that the insulator or non-conductive body 11 of working end 10 carries an interior chamber indicated at 30 communicating with lumen 33 that are adapted for delivery and transient confinement of a fluid media m that flows into the chamber 30. The chamber 30 communicates via lumen 33 with a fluid media source 35 that may be remote from the device, or a fluid reservoir (coupled to a remote pressure source) carried within introducer 12 or carried within a handle portion 14. The term fluid or flowable media source 35 is defined to include a positive pressure inflow system which may be a syringe, an elevated remote fluid sac that relies on gravity, or any suitable pump-type pressure means known in the art. The fluid delivery lumen 33 transitions to chamber 30 at proximal end portion 34a thereof. The distal end portion 34b of chamber 30 has a reduced cross-section to (optionally) function as a jet or nozzle indicated at 38.

Of particular interest, still referring to FIG. 4, paired electrode elements 40A and 40B with exposed surfaces and that are spaced apart in surface 42 of the interior fluid confinement chamber 30. In this exemplary embodiment, the electrode elements 40A and 40B comprise (i) circumferential exposed surfaces of a conductive material (ii) positioned at opposing proximal and distal ends of interior chamber 30. It should be appreciated that the method of the invention of may utilize any suitable configuration of spaced apart electrodes about at least one confinement chamber 30 or lumen portion. For example, each electrode may be a singular projecting element that projects into the chamber. The exemplary embodiment of FIG. 4 shows an elongate chamber having an axial dimension indicated at a and diameter or cross-section indicated at b. The axial dimension may range from about 0.1 mm. to 20.0 mm. and may be singular or plural as described below. The diameter b may range from micron dimensions (e.g., 5 µm) for miniaturized instruments to a larger dimension (e.g., 5.0 mm) for larger instruments for causing the thermally induced fluid-to-gas transformation required to cause the novel energy-tissue interaction of the invention. The electrodes are of any suitable material such as aluminum, stainless steel, nickel titanium, platinum, gold, or copper. Each electrode surface preferably has a toothed surface texture indicated at 43 that includes hatching, projecting elements or surface asperities for better delivering high energy densities in the fluid proximate to the electrode. The electrical current to the working end 10 may be switched on and off by a foot pedal or any other suitable means such as a switch in handle 14.

FIG. 4 further shows that a preferred shape is formed into the tissue-engaging surface 20A to better perform the method off using tissue. As can be seen in FIGS. 3A and 4, the first tissue-engaging surface 20A is generally concave so as to be adapted to receive a greater tissue volume in the central portion of surface 20A. The second tissue engaging surface 20B is flexible and naturally will be concave in the distal or opposite direction when tissue is engaged between surfaces 20A and 20B. This preferred shape structure allows for controllable compression of the thick targeted tissue volumes t centrally exposed to the energy delivery means and helps prevent conductance of thermal effects to collateral tissue regions ct (see FIG. 5B) and as will be described in greater detail below.

FIGS. 3A and 4 show that first tissue-engaging surface 20A defines an open grid structure of apertures or passageways indicated at 45 that pass therethrough. The apertures 45 may have any cross-sectional shape and linear or angular route through surface 20A with a sectional dimension c in this embodiment ranging upwards from micron dimensions (e.g., 5 µm) to about 2.0 mm. in a large surface 20A. The exemplary embodiment of FIG. 4 has an expanding cross-section transition chamber 47 proximate to the aperture grid that transitions between the distal end 34b of chamber 30 and the apertures 45. However, it should be appreciated that such a transition chamber 47 is optional and the terminal portion of chamber 30 may directly exit into a plurality of passageways that each communicate with an aperture 45 in the grid of the first engaging surface 20A. In a preferred embodiment, the second tissue-engaging surface 20B defines (optionally) a grid of apertures indicated at 50 that pass through the loop 22B. These apertures 50 may be any suitable dimension (cf. apertures 45) and are adapted to generally oppose the first tissue-engaging surface 20A when the surfaces 20A and 20B are in the second closed position, as shown in FIG. 3B.

The electrodes 40A and 40B of working end 10 have opposing polarities and are coupled to electrical generator 55. FIG. 4 shows current-carrying wire leads 58a and 58b that are coupled to electrodes 40A and 40B and extend to electrical source 55 and controller 60. In a preferred embodiment of the invention, either tissue-engaging surface optionally includes a sensor 62 (or sensor array) that is in contact with the targeted tissue surface (see FIG. 3A). Such a sensor, for example a thermocouple known in the art, can measure temperature at the surface of the captured tissue. A thermocouple typically consists of paired dissimilar metals such as copper and constantan that form a T-type thermocouple. The sensor is coupled to controller 60 by a lead (not shown) and can be used to modulate or terminate power delivery as will be described next in the method of the invention.

Figure 5A:
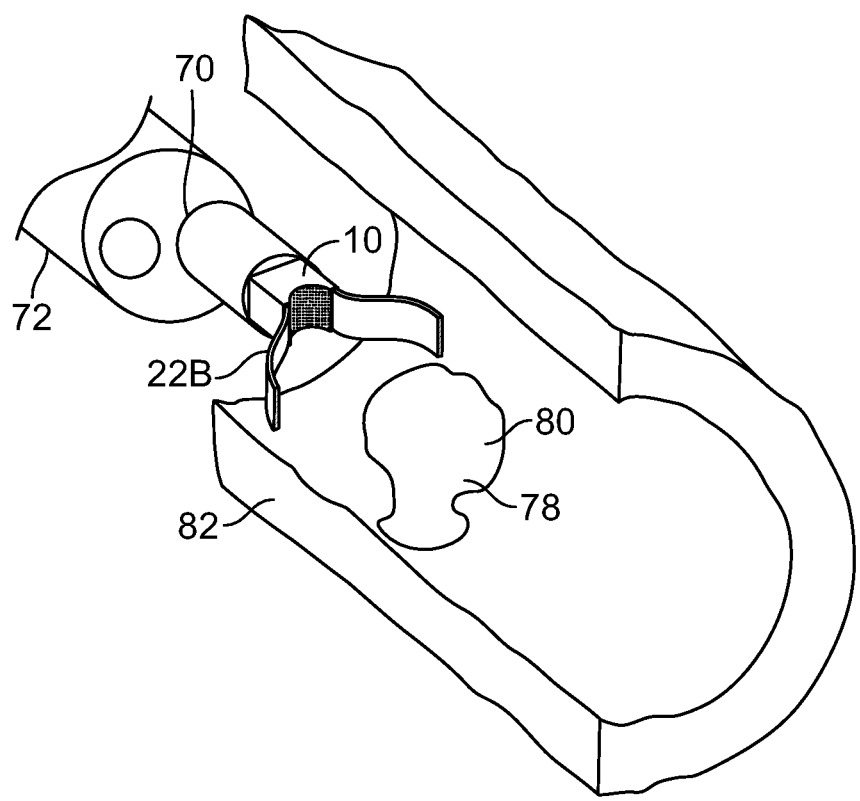
FIGS. 5A-5B are perspective views of the working end of FIG. 4 capturing an exemplary tissue volume, such as a polyp in a patient's colon.
Figure 5B:
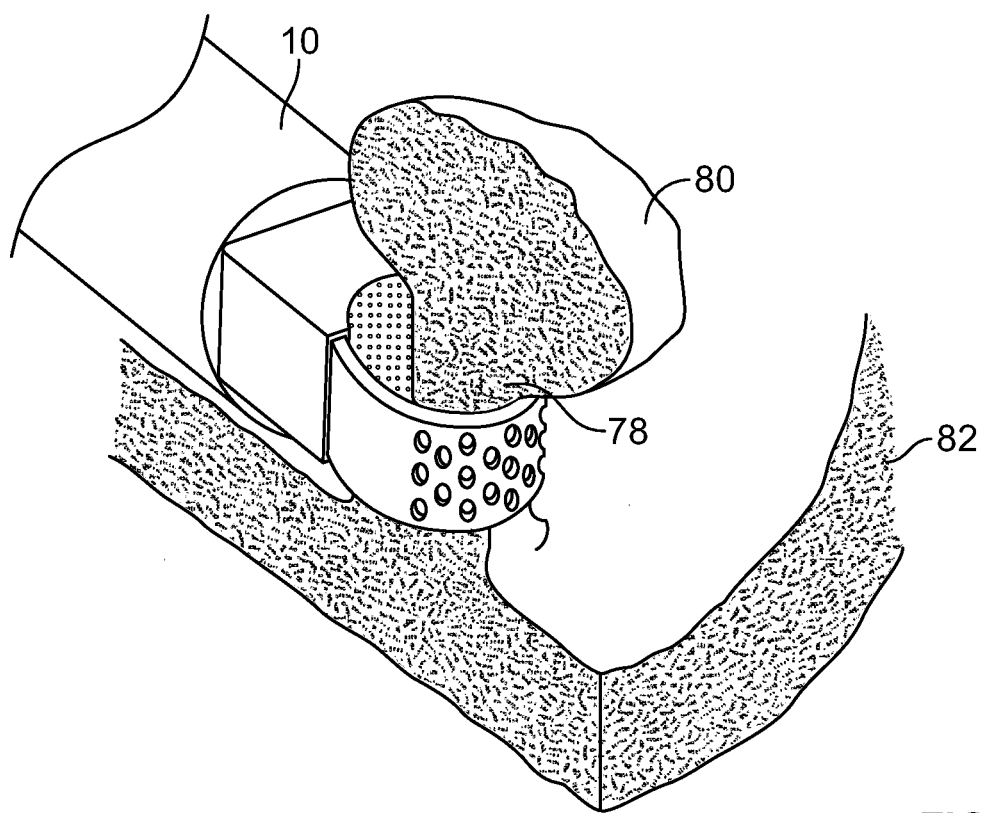

Operation and use of the working end of FIGS. 3A-3B and FIG. 4 in performing a method of the invention can be briefly described as follows in an endoscopic polyp removal procedure. FIGS. 5A-5B show working end 10 carried by an elongate catheter-type introducer member 12 and introduced through a working channel 70 of an endoscope 72 to a working space. In this case, the tissue t targeted for fusing or sealing is a medial portion 78 of a polyp 80 in a colon 82. It can be easily understood that the slidable movement of the loop member 22B can capture the polyp 80 in the device as shown in FIG. 5B after being lassoed. The objective of the tissue treatment is to (i) seal the medial portion of the polyp with the present invention, and thereafter (ii) utilize a separate cutting instrument to cut through the fused or sealed portion; and then (iii) retrieve the excised polyp for biopsy purposes.

Figure 6A:
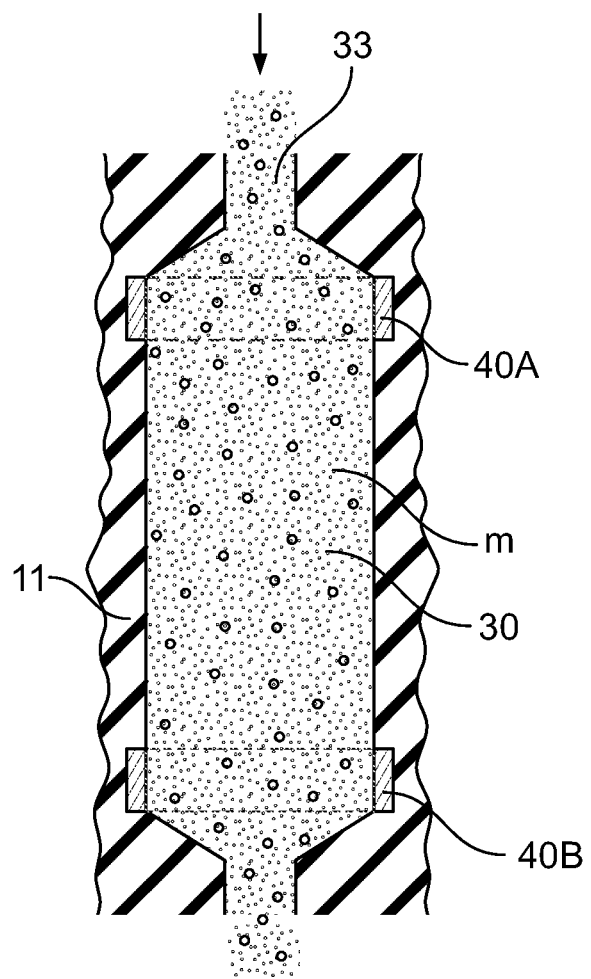
FIGS. 6A-6B are sectional schematic views of working end of FIG. 4 depicting, in sequence, the steps of a method of the present invention to seal or weld a targeted tissue volume.
Figure 6A:
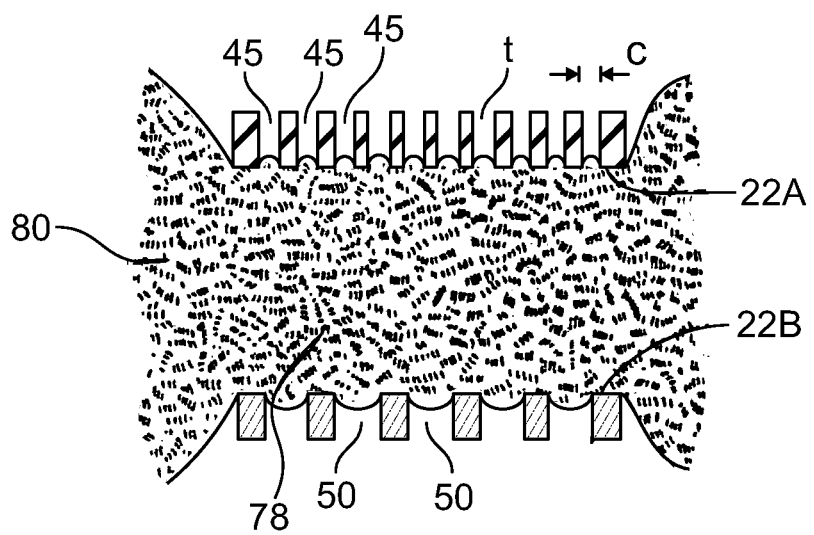
Figure 6B:
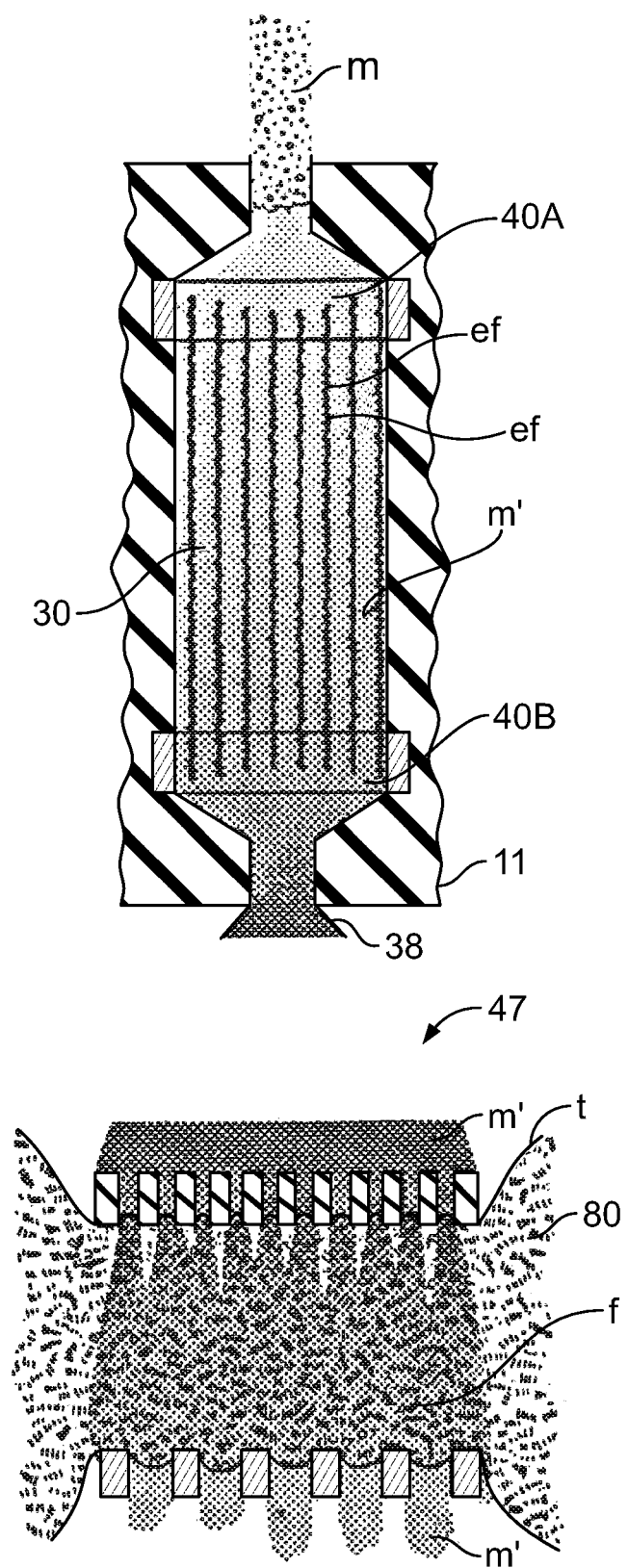

Now turning to FIGS. 6A-6B, two sequential schematic views of the working end engaging tissue t of the medial region of a polyp are provided to illustrate the energy-tissue interaction caused by the fluid-to-gas energy delivery means of the invention. FIG. 6A depicts an initial step of the method wherein the operator sends a signal to the controller 60 to delivery fluid media m (e.g., sterile water or saline solution) through lumen 33 into chamber 30. FIG. 6B depicts the next step of the method wherein the controller delivers an intense discharge of electrical energy to the paired electrode elements 40A and 40B within chamber 30 indicated by electric arc or electric field ef. The electrical discharge causes explosive vaporization of fluid media m (FIG. 6A) into a gas media indicated at m' (FIG. 6B). The greatly increased volume of gas media m' results in the gas being ejected from chamber 30 at high velocity through apertures 45 of the surface 20A and into the targeted tissue t. The fluid-to-gas conversion caused by the electrical discharge also heats the gas media m' to about 100° C. to deliver thermal effects deeply into tissue t, or even through the targeted tissue t, as indicated graphically by the shaded regions of gas flow in FIG. 6B. Depending on the character of the introduced liquid media, the media can be altered from a first lesser temperature to a second greater temperature in the range of 85° to 115° C. It is believed that this form of gas media m' (or steam) can uniformly elevate the temperature of the captured tissue to the desired range of about 65° C. to 100° C. very rapidly (i) to cause hydrothermal 20 denaturation of proteins in the tissue, and (ii) to cause optimal fluid inter-mixing of tissue constituents that will result in an effective seal or weld. At the same time, as the heat of media m' is absorbed by the water in the targeted tissue, the media m' converts back to a fluid (e.g., water) thus hydrating the targeted tissue t. It is believed that such protein denaturation by hydrothermal effects differentiates this method of tissue fusion from all other forms of energy delivery, such as radiofrequency energy delivery. All other forms of energy delivery vaporize intra- and extracellular fluids and cause tissue desiccation, dehydration or charring which is undesirable for the intermixing of denatured tissue constituents into a proteinaceous amalgam.

The above electrical energy deliver step is repeated at a high repetition rate to cause a pulsed form of thermal energy delivery in the engaged tissue. The fluid media m inflow may be continuous or pulsed to substantially fill chamber 30 before an electrical discharge is caused therein. The repetition rate of electrical discharges may be from about 1 Hz to 1000 Hz. More preferably, the repetition rate is from about 10 Hz to 200 Hz. The selected repetition rate preferably provides an interval between electrical discharges that allows for thermal relaxation of tissue, that may range from about 10 ms to 500 ms. The electrical source or voltage source 55 may provide a voltage ranging between about 100 volts and 10,000 volts to cause instant vaporization of the volume of fluid media m captured between the electrode elements 40A and 40B. After a selected time interval of such energy application to tissue t, that may range from about 1 second to 30 seconds, and preferably from about 5 to 20 seconds, the engaged tissue will be contain a core region in which the tissue constituents are denatured and intermixed under relatively high compression between surfaces 20A and 20B. Upon disengagement and cooling of the targeted tissue t, the treated tissue will be fused or welded. Over time, the body's wound healing response will reconstitute the treated tissue with an intermixed collagenous volume or scar-like tissue.

An optional method of controlling the repetition rate of electrical discharges comprises the measurement of electrical characteristics of media m within the chamber 30 to insure that the chamber is filled with the fluid media at time of the electrical discharge. The electrical measurement then would send a control signal to the controller 60 to cause each electrical discharge. For example, the fluid media m can be provided with selected conductive compositions in solution therein. The controller 60 then can send a weak electrical current between the paired electrodes 40A and 40B and thereafter sense the change in an impedance level between the electrodes as the chamber 30 is filled with fluid to generate the control signal.

Figure 1A:
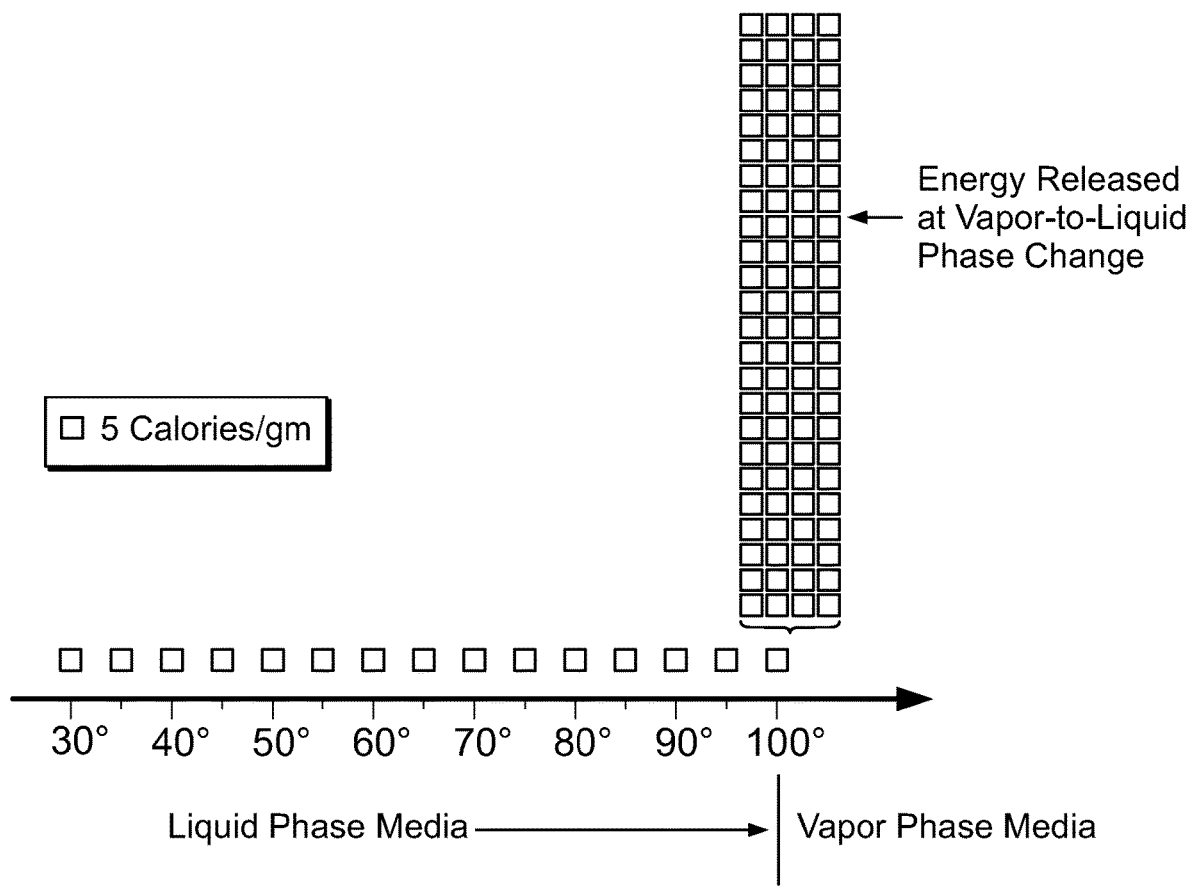
FIG. 1A is an illustration of a prior art laser-induced thermal weld effect in two approximated tissue layers.
Figure 1B:
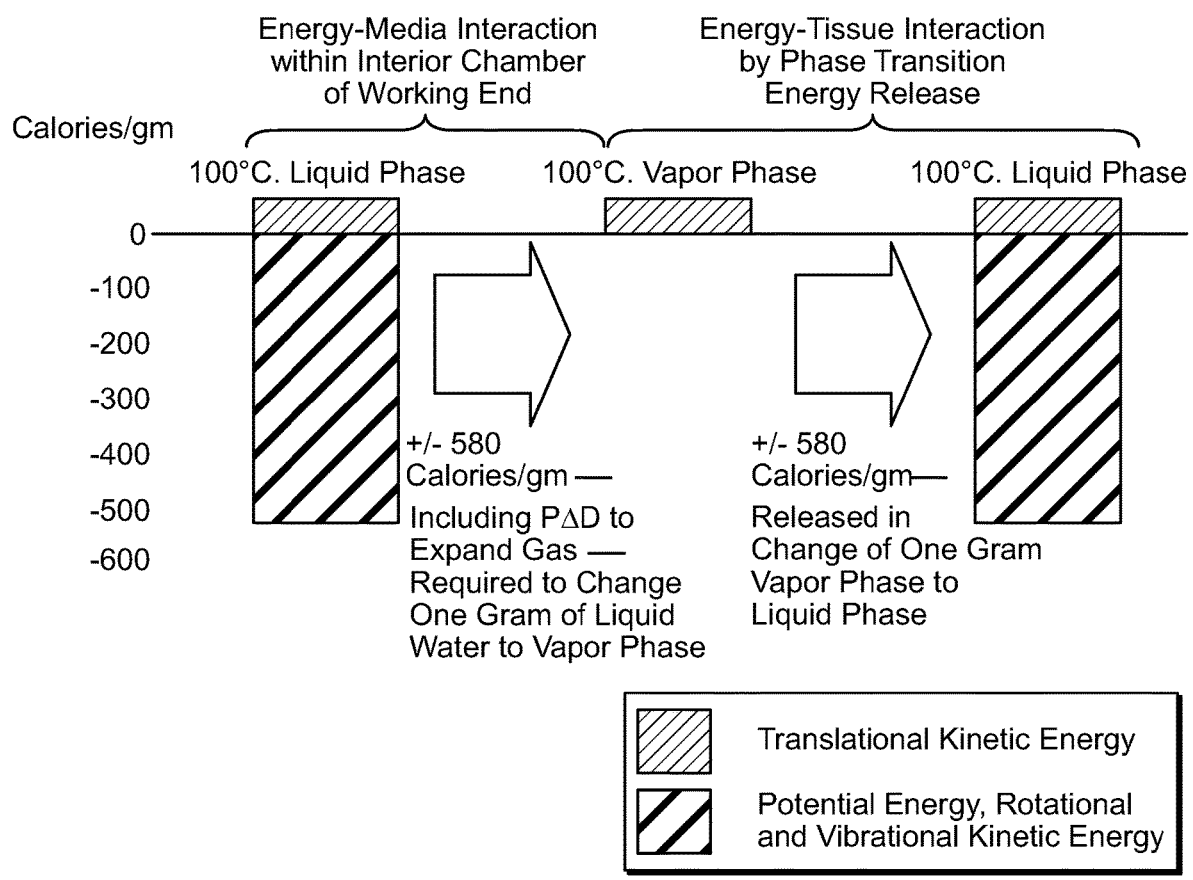
FIG. 1B is an illustration of a prior art radiofrequency energy induced thermal weld effect in two approximated tissue layers.
Figure 2A:
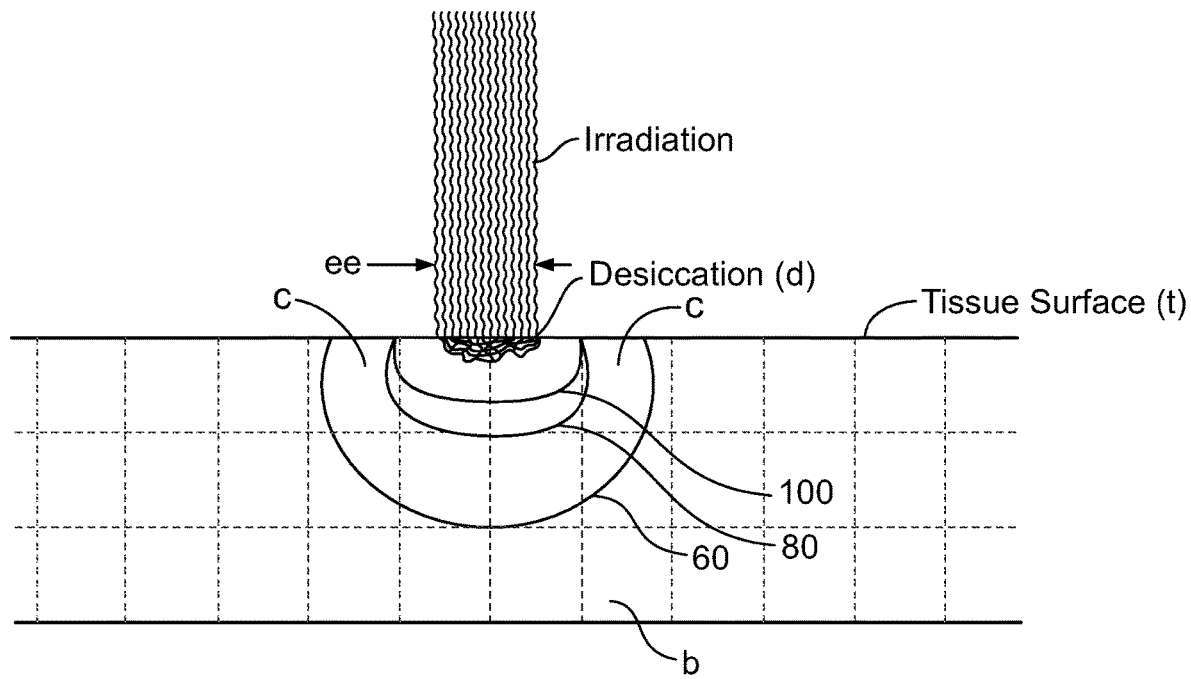
FIG. 2A is a graphical depiction of the quantity of energy needed to achieve the heat of vaporization of water.
Figure 2B:
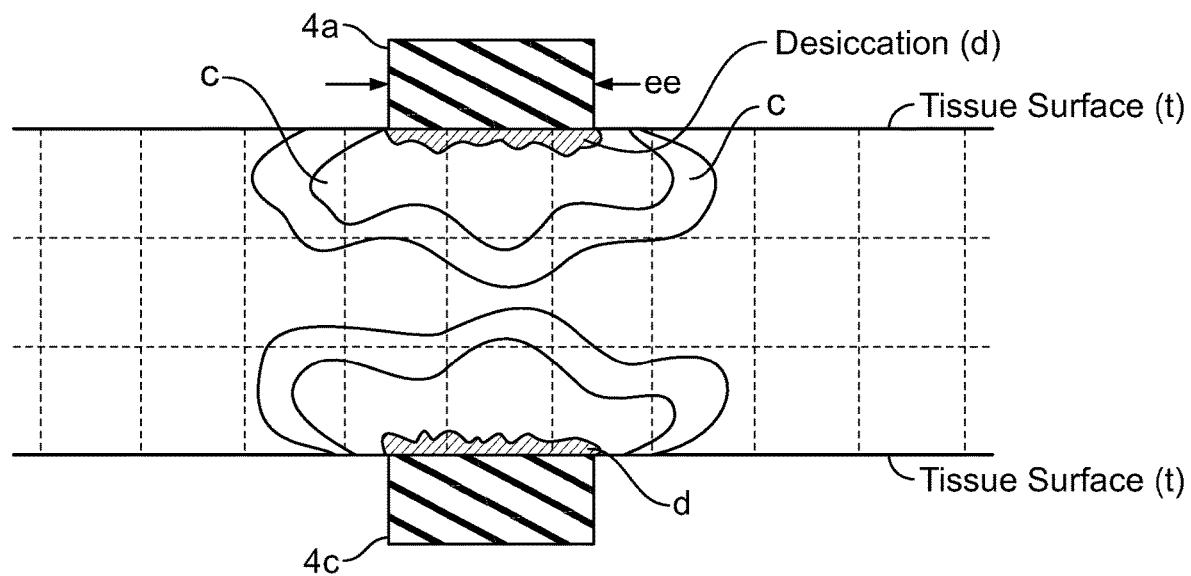
FIG. 2B is a diagram of phase change energy release that underlies one method of the invention.

FIG. 6B further shows that the engaged tissue t of polyp 80 defines a medial portion that comprises the engaged tissue t and collateral tissue regions indicated at ct. It can be seen that the gas media m' will penetrate the medial engaged tissue t of the polyp but will not penetrate the collateral tissue ct not engaged between the engaging surfaces 20A and 20B. Of particular interest, the collateral tissue regions et will thus not be elevated significantly in temperature and little collateral thermal damage will result. This desired lack of collateral thermal damage is to be contrasted with radiofrequency (Rf) energy delivery between one of more electrodes engaging the targeted tissue, in which Rf current will flow outwardly into and through the tissue regions ct and cause collateral thermal damage (see FIG. 1B). In the exemplary polyp removal procedure described herein, the invention's ability to limit collateral thermal damage is important for two reasons. First, it is important to maintain the portion of the polyp to be resected in a non-desiccated condition since it will be biopsied. Second, it is important to prevent thermal damage to the colon wall 94 at the base of the polyp 80, since any damage or perforation of the wall could result in serious complications. Still referring to FIG. 6B, it is estimated that temperature ranges will transition rapidly from a threshold level capable of denaturing proteins in the medial targeted tissue t, to subthreshold levels in the collateral tissue ct. In substantial part, the rapid temperature transition results from the transition between the compressed medial tissue t that in compressed between the engagement surfaces 20A and 20B and the collateral tissue volumes that are not engaged and compressed. It is the combination of tissue compression with the gas media induced elevation in temperature that can cause rapid denaturation of proteins in the targeted tissue t. The non-compressed collateral tissue ct will disperse any heat rapidly to limit collateral thermal damage. FIG. 6B further shows a resection line r along which the polyp can be transected with a separate instrument to leave a sealed margin at the base of the polyp that prevents any bleeding following the resection procedure.

Figure 7A:
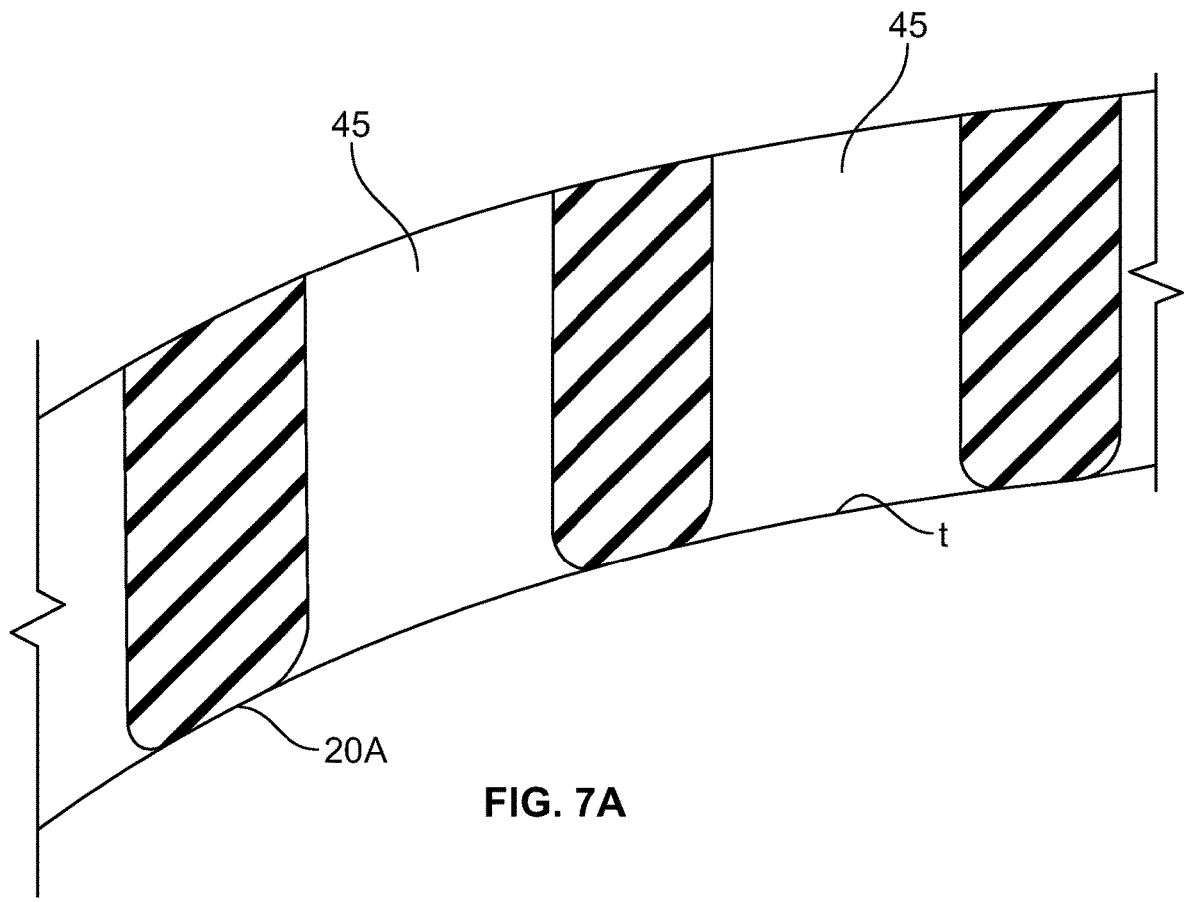
FIGS. 7A-7B are enlarged sectional views of apertures of the working end of FIG. 4 depicting a passive component of the present invention.
Figure 7B:
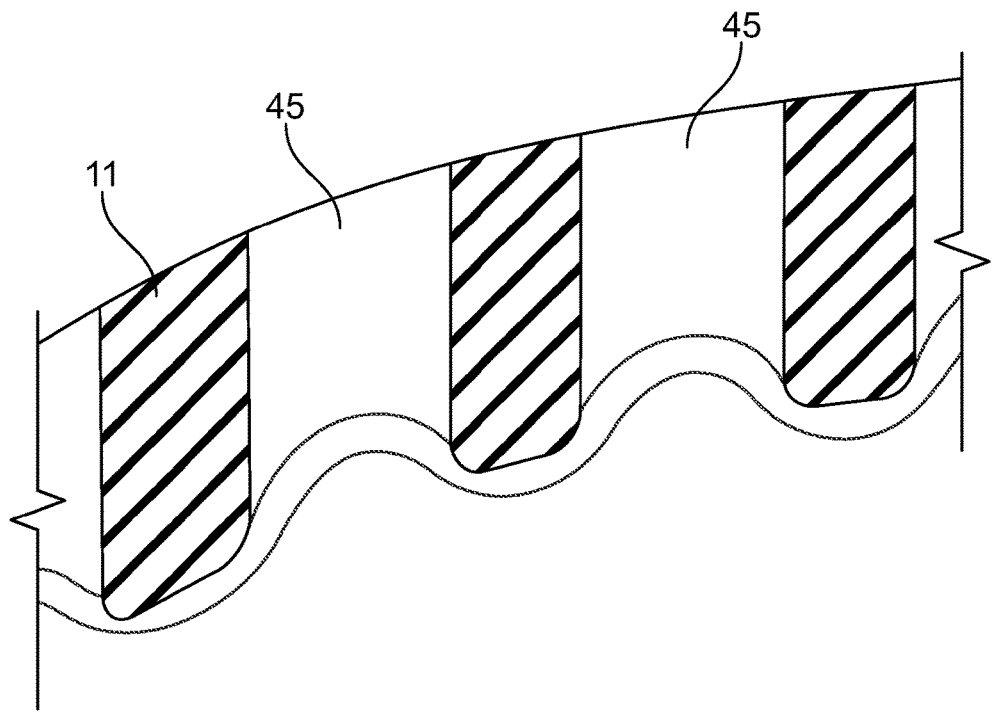

In another aspect of the method of the invention, the engaging surfaces 20A and 20B can provide controllable tissue-compression means that will assist in the fusion of the engaged tissue volume t. Referring to FIGS. 7A-7B, by defining a selected scale of the cross-sectional dimensions c of the apertures 45 and 50 in the engaging surfaces 20A and 20B, the invention provides controllable tissue-compression means for maintaining the targeted tissue t under the approximate desired pressures for causing tissue fusion. The cross-sectional dimension c is intended to represent a minimum side dimension of a rectangular aperture 45, or the diameter of a round aperture 50, as it is believed that the area of the aperture can be engineered to cooperate with a tissue surface s to optimize energy absorption. As can be seen in FIGS. 7A-7B, a targeted tissue volume t that is being treated or fused by the method of the invention is believed to undergo several stages in rapid succession. FIG. 7A shows a greatly enlarged sectional view of the step of capturing the targeted tissue t between the first and second engaging surfaces 20A and 20B before thermal energy delivery. FIG. 7B next depicts the effect of hydrothermal energy delivery in which collagen and other proteins denature as well as hydration of the targeted site t. The denaturation of collagen causes the unwinding of its helical molecular structure and results in an expanded volume of tissue. This protein denaturation and tissue hydration causes the tissue surfaces s to expand and swell in the directions of arrows ar into apertures 45 and 50 as shown in FIG. 7B. The targeted tissue t is unable to swell in the directions of arrows ar' since the tissue is constrained by the side portions 95a and 95b of the working end 10 (see FIG. 4 and FIG. 6A). By providing apertures in the engaging surfaces 20A and 20B of a selected dimension c, the tissue can be controllably allowed to swell or expand into the apertures 45 and 50. It has been observed that overly high compression of tissues is adverse to creating effective tissue fusion, it is believed because such compression reduces the ability of denatured proteins and other tissue constituents to intermix and thereafter fuse uniformly upon healing. After a ramp down in temperature, the fused portion f of FIG. 7B will shrink from within the apertures 45. The invention provides tissue engaging surfaces 20A and 20B that carry a grid of apertures having a selected cross-sectional dimension ranging from about 0.2 mm to 2.0 mm for receiving swelled tissue, and more preferably from about 0.5 mm to 2.0 mm. Thus, the tissue-receiving apertures 45 and 50, by having selected dimensions that can act as a passive component of the invention to transiently receive swelled tissue in the ramp-up in temperature and hydration to slightly reduce tissue compression, and thereafter release the tissue in the ramp-down in temperature and swelling. It should be appreciated that such apertures or recessed portions of a selected dimension may be provided in the engaging surface of any jaw structure (e.g., any Rf electrode jaw) for achieving the purpose of this method.

2. Type "B" System for Tissue Fusion and Method of Making Working End.

Figure 8:
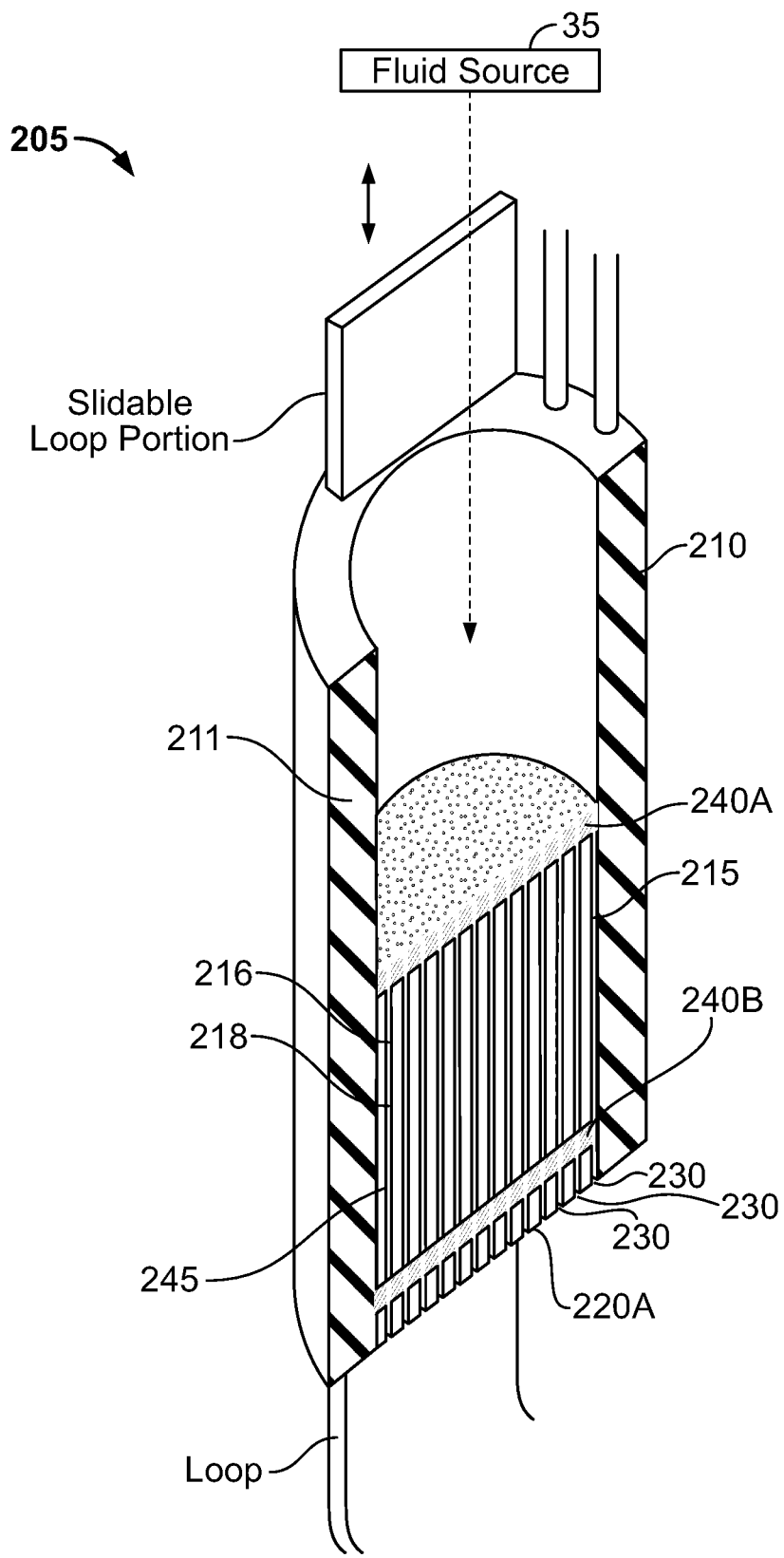
FIG. 8 is sectional views of an exemplary working end of a Type "B" probe of the present invention.

Referring to FIG. 8, a working end 210 of a Type "B" system 205 of the present invention is depicted. The fluid-to-gas energy delivery aspects of the Types "A" and "B" systems are similar with the exception that the Type "B" system provides a significantly reduced dimensions (or micronizanon) of the features of the working end 210. More particularly, a source 35 of fluid media as described above is adapted to flow the media through the introducer body 211 and thereafter into a microchannel body 215 that defines a plurality of fluid or gas passageways or microchannel portions 230 (collectively).

The microchannel body 215 comprises a structure of an electrically insulative material that has a proximal layer portion 216, a medial layer portion 218 and a distal working surface 220A for interfacing the targeted tissue t. The plurality of open passageways or microchannels 230 can be identified as extending through the proximal and medial portions 216 and 218 and exiting the distal working surface 220A. Within the proximal portion 216 of the microchannel body 215 is a first electrode element 240A that may be formed in a plate or layer 242A that intersects the passageways 230. Thus, each channels has a first electrode surface 244a exposed therein. Similarly, the medial portion 218 of microchannel body 215 carries a second electrode element 240B that is formed in a layer 242B to provide a second electrode surface 244b exposed in the microchannels 230.

This Type "B" working end and microchannel body 215 can be fabricated in the following manners. The working surface 220A that carries the microchannel structure proximal thereto can be fabricated by the same processes as a micro-channel plate (MCP). The insulator material 245 of the working surface may be glass, plastic, ceramic, a form of silicon or any other suitable material. As an example of fabricating the microchannels, a microchannel plate (MCP) is a device that is commercially available for photo-detection purposes and may be adapted for use in the present invention. In an MCP, a tubular cladding glass is mechanically supported in its bore by the insertion of a rod of etchable core glass to produce a potential microchannel. The assembly is then pulled through an oven and drawn down in diameter to produce a microchannel (after the core is etched away). A plurality of such drawn-down assemblies then are stacked and drawn down through the oven until a selected diameter is achieved for the core. Thereafter, the assembly is fused together and the cores are etched away leaving the microchannel structure. While commercially available MCP's typically may have channels or capillaries ranging from about 5 µm and 25 µm in diameter, for photo detection purposes, it can be seen that any suitable diameter of channels can be fabricated by the above methods, and a preferred range is from about 0.2 µm to 400 µm in cross-section. More preferably, the range of cross sectional dimension is from about 1.0 µm to 200 µm. Another manner of fabricating the microchannel structure of the present invention is to use conventional semi-conductor processing methods to create both the microchannels and the electrode layers in an insulator material as is known in the art and in the MEMS field (microelectrical machining).

Figure 9:
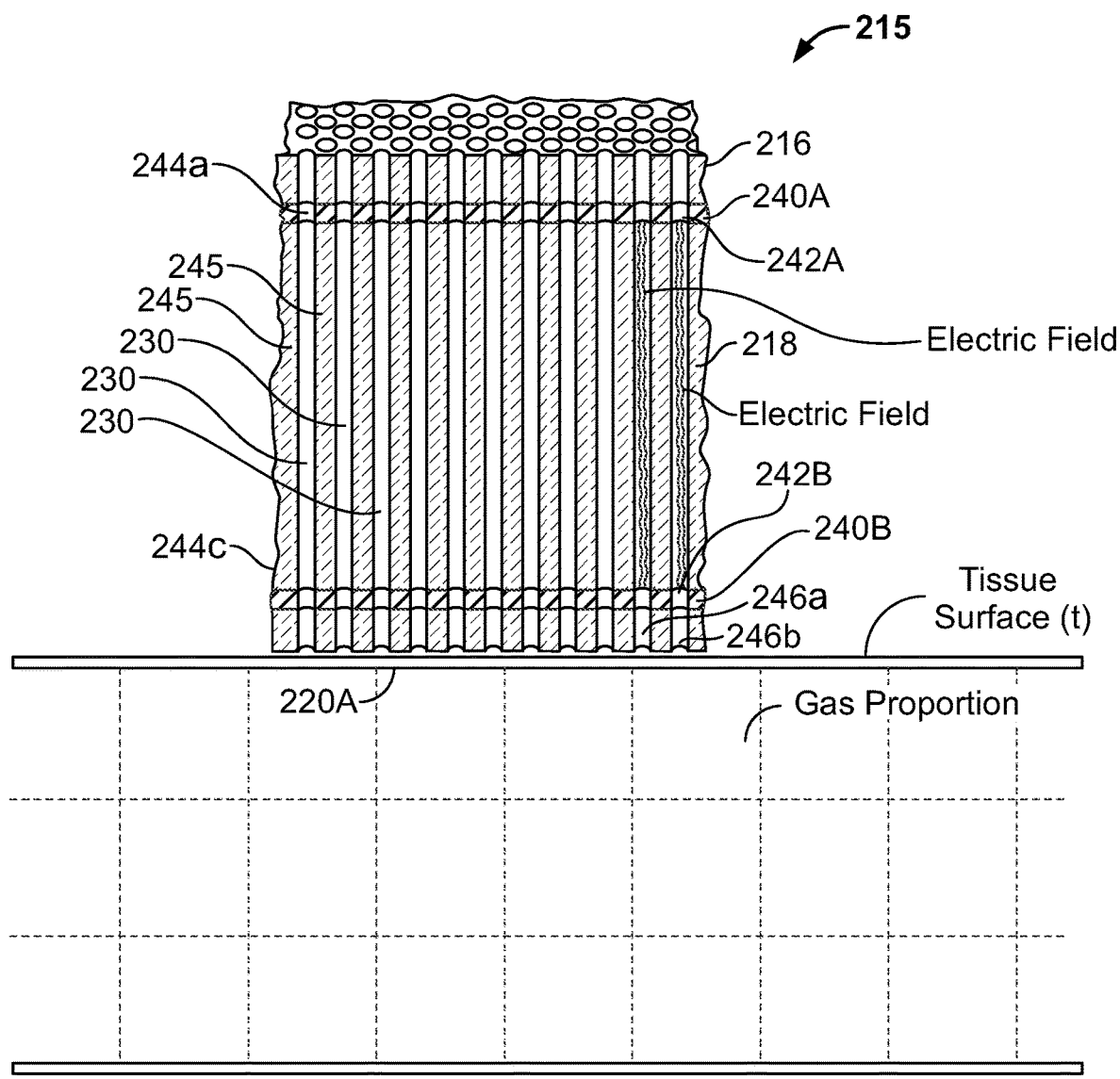
FIG. 9 is a greatly enlarged sectional view of the working end of FIG. 8 showing a microchannel structure and electrode arrangement carried therein.

In FIG. 9, an enlarged sectional view of a very small portion of the microchannel body 215 shows several microchannels 230 with open distal terminations 246a-246b in the working surface 220A. In any embodiment, the electrode layer indicated at 240A provides exposed surfaces 242a (collectively) that interface in a proximal portion of the microchannels. Similarly, the electrode layer 240B provides exposed surfaces 242b (collectively) that interface in a distal portion of the microchannels. It can be easily understood that for testing purposes, two MCP's can be sandwiched together to comprise the desired structure with a layer of insulator material 245 at the tissue engaging surface 220A. The distal electrode surface may be removed. Thus, the distal electrode exposed surfaces 242b are spaced inwardly or proximal from the distal most working surface 220A a selected dimension that ranges from about 5 µm to 500 µm, in general varying in dimension in direct proportion with the cross-section of the channel and the voltage levels used. In other words, the electrode exposed surfaces 242b have a covering layer of insulator material 245 that prevents direct contact of any electrode with tissue in contact with the surface 220A. The method of using the Type "B" embodiment is substantially the same as the previously described to deliver a superheated gas media into targeted tissue, and need not be repeated. It can be easily understood that microchannel bodies 215 of the type shown in FIGS. 9-10 can be provided in one or both jaws of any type of tissue-engaging instrument.

Such a Type "B" channeled structure in a working end also can be carried in the sidewall of a catheter that is from 1.0 to 3.0 mm in diameter (not limiting). The microchannel structure would be oriented so that the heated fluid media is ejected transverse to the axis of the catheter. The targeted tissue t may be myocardium or other cardiac tissue in which it is desirable to create a linear weld, fusion or ablation in the tissue to alter electrical signal transmission in a treatment for atrial fibrillation as is known in the art. It is postulated that the method of the invention can create the desired elongate linear thermal effect in the targeted tissue with greater control over (i) the lateral margins of the treatment path, and (ii) the depth of treatment, when compared to prior art radiofrequency devices that deliver Rf energy that courses through the tissue in an unpredictable manner. A catheter may have with an optional expandable balloon for engaging an opposing wall of a cardiac structure to press the working surface against the targeted tissue t.

A Type "B" working end also may be used in orthopedic procedures to cause hydrothermal shrinkage of collagen, for example in a spinal disc, or a joint capsule to stabilize the joint (see co-pending U.S. patent application Ser. No. 09/049,711 filed Mar. 27, 1998, incorporated herein by this reference). For example, the working end may be painted across a targeted tissue site in a joint capsule to shrink: tissue. The working end maybe stabilized against any collagenous tissue to heat and shrink: collagen in a targeted tissue such as a herniated disc.

The thermal energy delivery means of the invention preferably uses an electrical energy source for flash vaporization of a liquid media. It should be appreciated that an infrared laser source could be used to vaporize water or other lasers could be used to vaporize any other suitable fluid seeded with an absorbing biocompatible chromophore known in the art, and these embodiments fall within the scope of the invention.

Figures 10, 11:
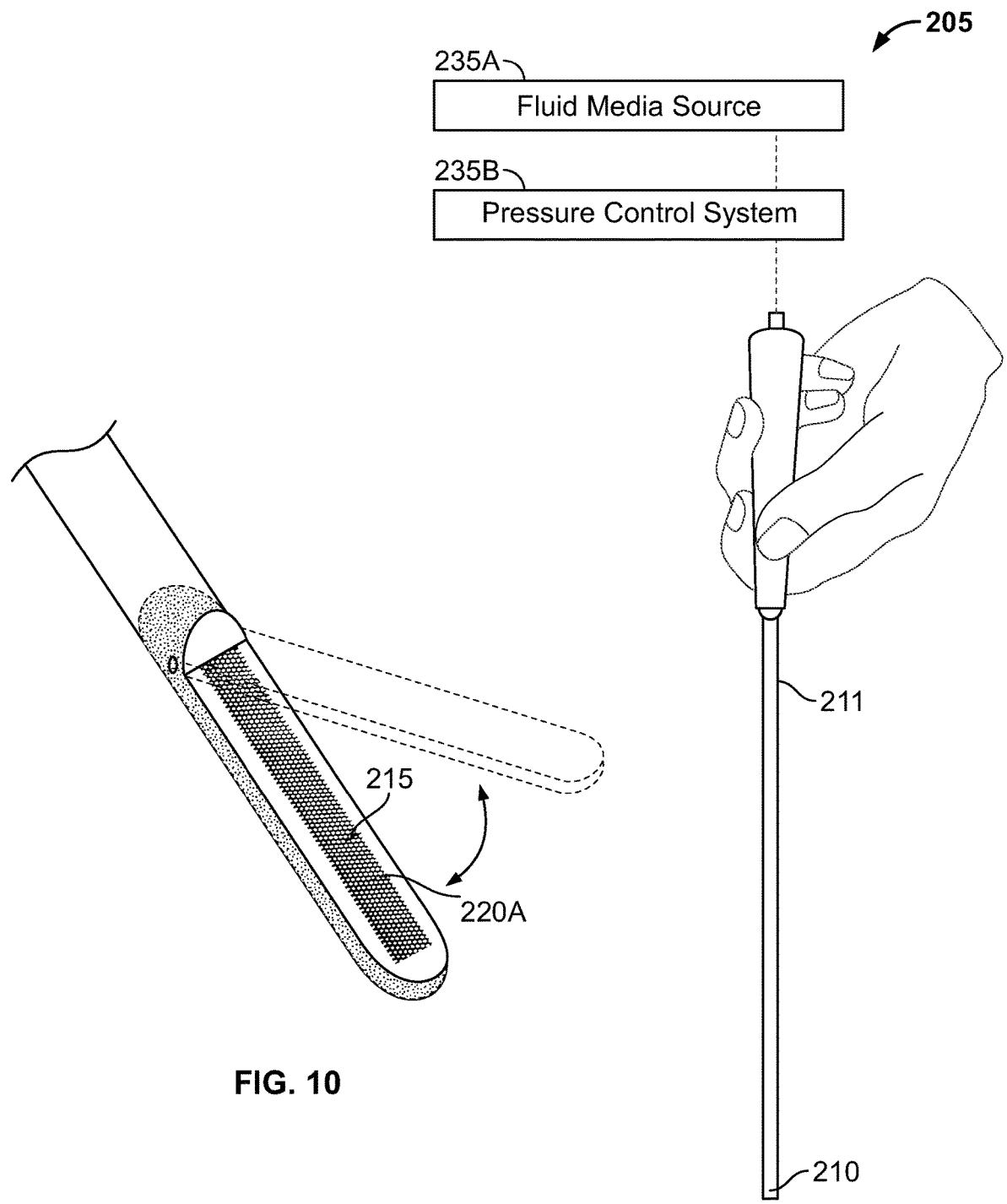
FIG. 10 is a perspective view of an alternative working end of a Type "B" embodiment with the working surface and channeled structure carried in a jaw of a tissue-engaging instrument.
FIG. 11 is a perspective view of an alternative working end of the present invention.

It should be appreciated that the present invention has been described in detail in a particular embodiment suited for fusing or sealing a medial portion of a polyp prior to its resection. A similar working end may be used for capturing and fusing or sealing various other anatomic structures or tissue volumes in an endoscopic or open surgery. The working end of the instrument may be adapted to an open and closeable jaw structure to capture tissue as shown in FIG. 10, rather than a "loop" to lasso tissue as in FIGS. 5A-5B.

3. Type "C" Thermotherapy Instrument.

Referring to FIGS. 3A, 3B and 4, the working end 10 of alternatively a Type "C" system 5 of an embodiment of the present invention is shown that is adapted for endoscopic procedures in which a tissue volume T targeted for treatment (a thermoplasty) can be captured by a loop structure. The working end 10 comprises a body 11 of insulator material (see FIG. 4) coupled to the distal end of introducer member 12 extending along axis 15. In this exemplary embodiment, the working end 10 has a generally cylindrical cross-section and is made of any suitable material such as plastic, ceramic, glass, metal or a combination thereof. The working end 10 is substantially small in diameter (e.g., 2 mm to 5 mm) and in this embodiment is coupled to an elongate flexible introducer member 12 to cooperate with a working channel in an endoscope. Alternatively, the working end 10 may be coupled to a rigid shaft member having a suitable 1 mm to 5 mm or larger diameter to cooperate with a trocar sleeve for use in endoscopic or microsurgical procedures. A proximal handle portion 14 of the instrument indicated by the block diagram of FIG. 3A carries the various actuator mechanisms known in the art for actuating components of the instrument.

In FIGS. 3A, 3B and 4, it can be seen that the working end 10 carries an openable and closeable structure for capturing tissue between a first tissue-engaging surface 20A and a second tissue-engaging surface 20B. In this exemplary embodiment, the working end 10 and first tissue-engaging surface 20A comprises a non-moving component indicated at 22A that is defined by the exposed distal end of body 11 of working end 10. The second tissue-engaging surface 20B is carried in a moving component that comprises a flexible loop structure indicated at 22B.

The second moving component or flexible loop 22B is actuatable by a slidable portion 24a of the loop that extends through a slot 25 in the working end to an actuator in the handle portion 14 as is known in the art (see FIG. 4). The other end 24b of the loop structure 22B is fixed in body 11. While such an in-line (or axial) flexible slidable member is preferred as the tissue-capturing mechanism for a small diameter flexible catheter-type instrument, it should be appreciated that any openable and closable jaw structure known in the art falls within the scope of the invention, including forms of paired jaws with cam-surface actuation or conventional pin-type hinges and actuator mechanisms. FIG. 3A illustrates the first and second tissue-engaging surfaces 20A and 20B in a first spaced apart or open position. FIG. 3B shows the first and second surfaces 20A and 20B moved toward a second closed position.

Now turning to the fluid-to-gas energy delivery means of the invention, referring to FIG. 4, it can be seen that the insulated or non-conductive body 11 of working end 10 carries an interior chamber indicated at 30 communicating with lumen 33 that are together adapted for delivery and transient confinement of a fluid media M that flows into chamber 30. The chamber 30 communicates via lumen 33 with a fluid media source 35 that may be remote from the device, or a fluid reservoir (coupled to a remote pressure source) carried within introducer 12 or carried within a handle portion 14. The term fluid or flowable media source 35 is defined to include a positive pressure inflow system which may be a syringe, an elevated remote fluid sac that relies on gravity, or any suitable pump-type pressure means known in the art. The fluid delivery lumen 33 transitions to chamber 30 at proximal end portion 34a thereof. The distal end portion 34b of chamber 30 has a reduced cross-section to (optionally) function as a jet or nozzle indicated at 38.

Of particular interest, still referring to FIG. 4, paired electrode elements 40A and 40B with exposed surfaces and that are spaced apart in surface 42 of the interior fluid confinement chamber 30. In this exemplary embodiment, the electrode elements 40A and 40B comprise circumferential exposed surfaces of a conductive material positioned at opposing proximal and distal ends of interior chamber 30. It should be appreciated that the method of the invention of may utilize any suitable configuration of spaced apart electrodes (e.g., spaces apart helical electrode elements or porous electrodes) about at least one confinement chamber 30 or lumen portion. Alternatively, each electrode can be a singular projecting element that projects into the chamber. The exemplary embodiment of FIG. 4 shows an elongate chamber having an axial dimension indicated at A and diameter or cross-section indicated at B. The axial dimension may range from about 0.1 mm to 20.0 mm and may be singular or plural as described below. The diameter B may range from micron dimensions (e.g., 0.5 μm) for miniaturized instruments to a larger dimension (e.g., 5.0 mm) for larger instruments for causing the thermally induced fluid-to-gas transformation required to enable the novel phase change energy-tissue interaction of the invention. The electrodes are of any suitable material such as aluminum, stainless steel, nickel titanium, platinum, gold, or copper. Each electrode surface preferably has a toothed surface texture indicated at 43 that includes hatching, projecting elements or surface asperities for better delivering high energy densities in the fluid proximate to the electrode. The electrical current to the working end 10 may be switched on and off by a foot pedal or any other suitable means such as a switch in handle 14.

FIG. 4 further shows that a preferred shape is formed into the tissue-engaging surface 20A to better perform the method of fusing tissue. As can be seen in FIGS. 3B and 4, the first tissue-engaging surface 20A is generally concave so as to be adapted to receive a greater tissue volume in the central portion of surface 20A. The second tissue-engaging surface 20B is flexible and naturally will be concave in the distal or opposite direction when tissue is engaged between surfaces 20A and 20B. This preferred shape structure allows for controllable compression of the thick targeted tissue volumes T centrally exposed to the energy delivery means and helps prevent conductance of thermal effects to collateral tissue regions CT (see FIG. 5B) and as will be described in greater detail below.

FIGS. 3A and 4 show that first tissue-engaging surface 20A defines an open structure of at least one aperture or passageway indicated at 45 that allows vapor pass therethrough. The apertures 45 may have any cross-sectional shape and linear or angular route through surface 20A with a sectional dimension C in this embodiment ranging upwards from micron dimensions (e.g., 0.5 μm) to about 2.0 mm in a large surface 20A. The exemplary embodiment of FIG. 4 has an expanding cross-section transition chamber 47 proximate to the aperture grid that transitions between the distal end 34b of chamber 30 and the apertures 45. However, it should be appreciated that such a transition chamber 47 is optional and the terminal portion of chamber 30 may directly exit into a plurality of passageways that each communicate with an aperture 45 in the grid of the first engaging surface 20A. In a preferred embodiment, the second tissue-engaging surface 20B defines (optionally) a grid of apertures indicated at 50 that pass through the loop 22B. These apertures 50 may be any suitable dimension (cf. apertures 45) and are adapted to generally oppose the first tissue-engaging surface 20A when the surfaces 20A and 20B are in the second closed position, as shown in FIG. 3B.

The electrodes 40A and 40B of working end 10 have opposing polarities and are coupled to electrical generator 55. FIG. 4 shows current-carrying wire leads 58a and 58b that are coupled to electrodes 40A and 40B and extend to electrical source 55 and controller 60. In a preferred embodiment of the invention, either tissue-engaging surface optionally includes a sensor 62 (or sensor array) that is in contact with the targeted tissue surface (see FIG. 3A). Such a sensor, for example a thermocouple known in the art, can measure temperature at the surface of the captured tissue. The sensor is coupled to controller 60 by a lead (not shown) and can be used to modulate or terminate power delivery as will be described next in the method of the invention.

Operation and use of the working end of FIGS. 3A, 3B and 4 in performing a method of treating tissue can be briefly described as follows, for example in an endoscopic polyp removal procedure. As can be understood from FIG. 5B, the working end 10 is carried by an elongate catheter-type member 12 that is introduced through a working channel 70 of an endoscope 72 to a working space. In this case, the tissue T targeted for sealing is a medial portion 78 of a polyp 80 in a colon 82. It can be easily understood that the slidable movement of the loop member 22B can capture the polyp 80 in the device as shown in FIG. 5B after being lassoed. The objective of the tissue treatment is to seal the medial portion of the polyp with the inventive thermotherapy. Thereafter, utilize a separate cutting instrument is used to cut through the sealed portion, and the excised polyp is retrieved for biopsy purposes.

Now turning to FIGS. 6A and 6B, two sequential schematic views of the working end engaging tissue T are provided to illustrate the energy-tissue interaction caused by the method of the invention. FIG. 6A depicts an initial step of the method wherein the operator sends a signal to the controller 60 to delivery fluid media M (e.g., saline solution or sterile water) through lumen 33 into chamber 30. FIG. 6B depicts the next step of the method wherein the controller delivers an intense discharge of electrical energy to the paired electrode elements 40A and 40B within chamber 30 indicated by electric arc or electric field EF. The electrical discharge provides energy exceeding the heat of vaporization of the contained fluid volume. The explosive vaporization of fluid media M (of FIG. 6A) into a vapor or gas media is indicated at M' in FIG. 6B. The greatly increased volume of gas media M' results in the gas being ejected from chamber 30 at high velocity through apertures 45 of surface 20A into the targeted tissue T. The liquid to gas conversion caused by the electrical discharge also heats the gas media M' to about 100° C. to deliver thermal effects into tissue T, or even through the targeted tissue T, as indicated graphically by the shaded regions of gas flow in FIG. 6B. The fluid source and its pressure or pump mechanism can provide any desired level of vapor ejection pressure. Depending on the character of the introduced liquid media, the media is altered from a first lesser temperature to a second greater temperature in the range of 100° C. or higher depending on pressure. The ejection of vapor media M' will uniformly elevate the temperature of the engaged tissue to the desired range of about 65° C. to 100° C. very rapidly to cause hydrothermal denaturation of proteins in the tissue, and to cause optimal fluid intermixing of tissue constituents that will result in an effective seal. In effect, the vapor-to-liquid phase transition of the ejected media M' will deposit heat equal to the heat of vaporization in the tissue. At the same time, as the heat of vaporization of media M' is absorbed by water in the targeted tissue, the media converts back to a liquid thus hydrating the targeted tissue T. It is believed that such protein denaturation by hydrothermal effects differentiates this method of tissue sealing or fusion from all other forms of energy delivery, such as radiofrequency energy delivery. All other forms of energy delivery vaporize intra- and extracellular fluids and cause tissue desiccation, dehydration or charring which is undesirable for the intermixing of denatured tissue constituents into a proteinaceous amalgam.

The above electrical energy deliver step is repeated at a high repetition rate to cause a pulsed form of thermal energy delivery in the engaged tissue. The fluid media M inflow may be continuous or pulsed to substantially fill chamber 30 before an electrical discharge is caused therein. The repetition rate of electrical discharges may be from about 1 Hz to 1000 Hz. More preferably, the repetition rate is from about 10 Hz to 200 Hz. The selected repetition rate preferably provides an interval between electrical discharges that allows for thermal relaxation of tissue, that may range from about 10 ms to 500 ms. The electrical source or voltage source 55 may provide a voltage ranging between about 100 volts and 10,000 volts to cause instant vaporization of the volume of fluid media M captured between the electrode elements 40A and 40B. After a selected time interval of such energy application to tissue T, that may range from about 1 second to 30 seconds, and preferably from about 5 to 20 seconds, the engaged tissue will be contain a core region in which the tissue constituents are denatured and intermixed under relatively high compression between surfaces 20A and 20B. Upon disengagement and cooling of the targeted tissue T, the treated tissue will be fused or welded. Over time, the body's wound healing response will reconstitute the treated tissue with an intermixed collagenous volume or scar-like tissue.

An optional method of controlling the repetition rate of electrical discharges comprises the measurement of electrical characteristics of media M within the chamber 30 to insure that the chamber is filled with the fluid media at time of the electrical discharge. The electrical measurement then would send a control signal to the controller 60 to cause each electrical discharge. For example, the liquid media M can be provided with selected conductive compositions in solution therein. The controller 60 then can send a weak electrical current between the paired electrodes 40A and 40B and thereafter sense the change in an impedance level between the electrodes as the chamber 30 is filled with fluid to generate the control signal.

Referring to FIG. 11, a working end 210 of an alternative instrument 205 of the present invention is depicted. The phase transitional energy delivery aspects of the invention are the same as described above. The instrument 205 differs in that it utilizes significantly reduced dimensions (or micronization) of features in the working end 210. More particularly, a fluid media source 235A and pressure control system 235B are adapted to provide pressurized flows of liquid media M through the introducer body 211 and thereafter into microchannel body or structure indicated at 215 (see FIG. 12). The microchannel or microporous body defines therein plurality of small diameter fluid passageways or microchannel portions 216 (collectively). The microchannel body 215 also can be a microporous trabecular material to provide open-cell flow passageways therethrough.

Figure 12:
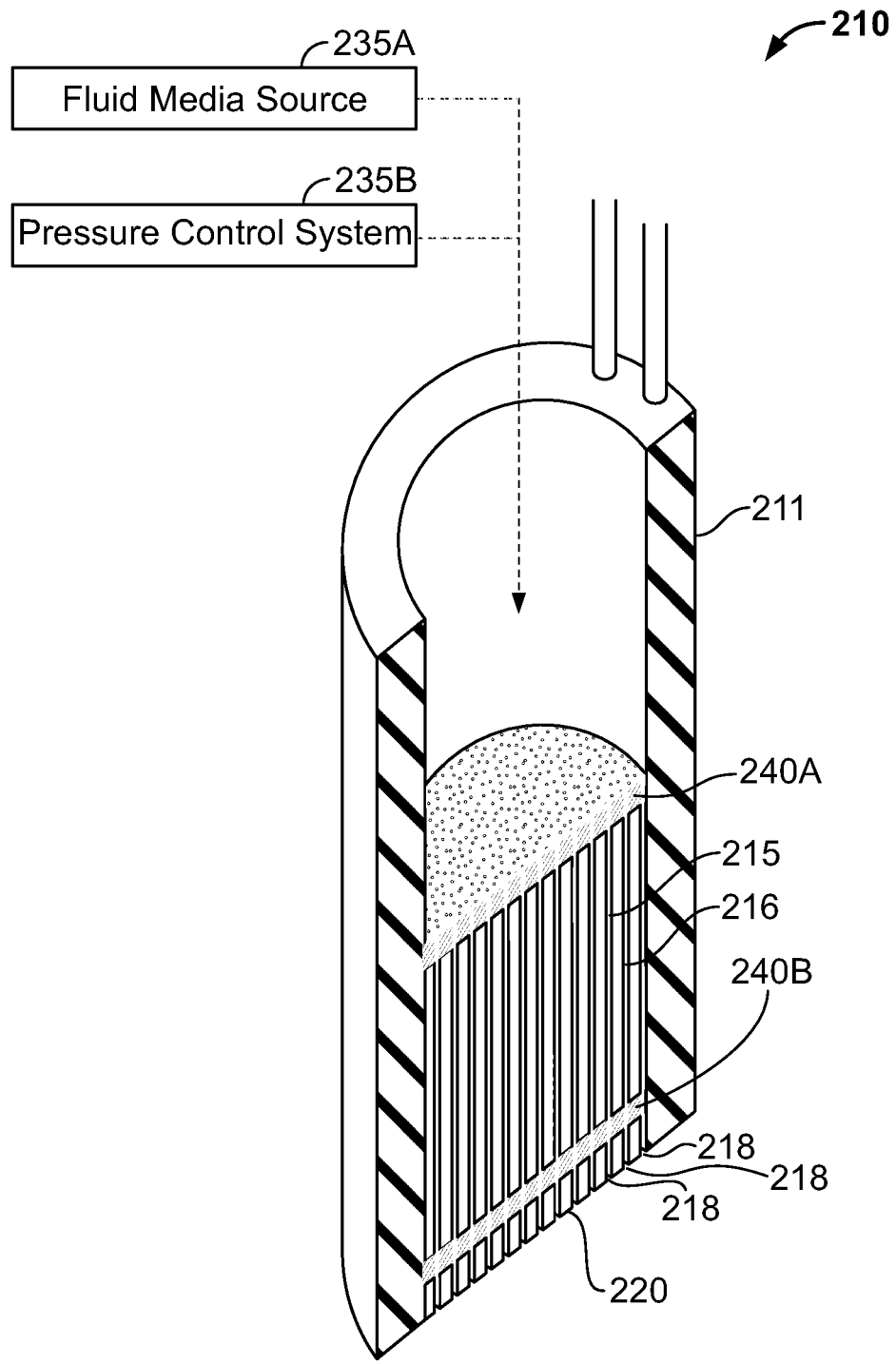
FIG. 12 is a sectional view of the working end of FIG. 11 showing a microchannel structure.
Figure 13:
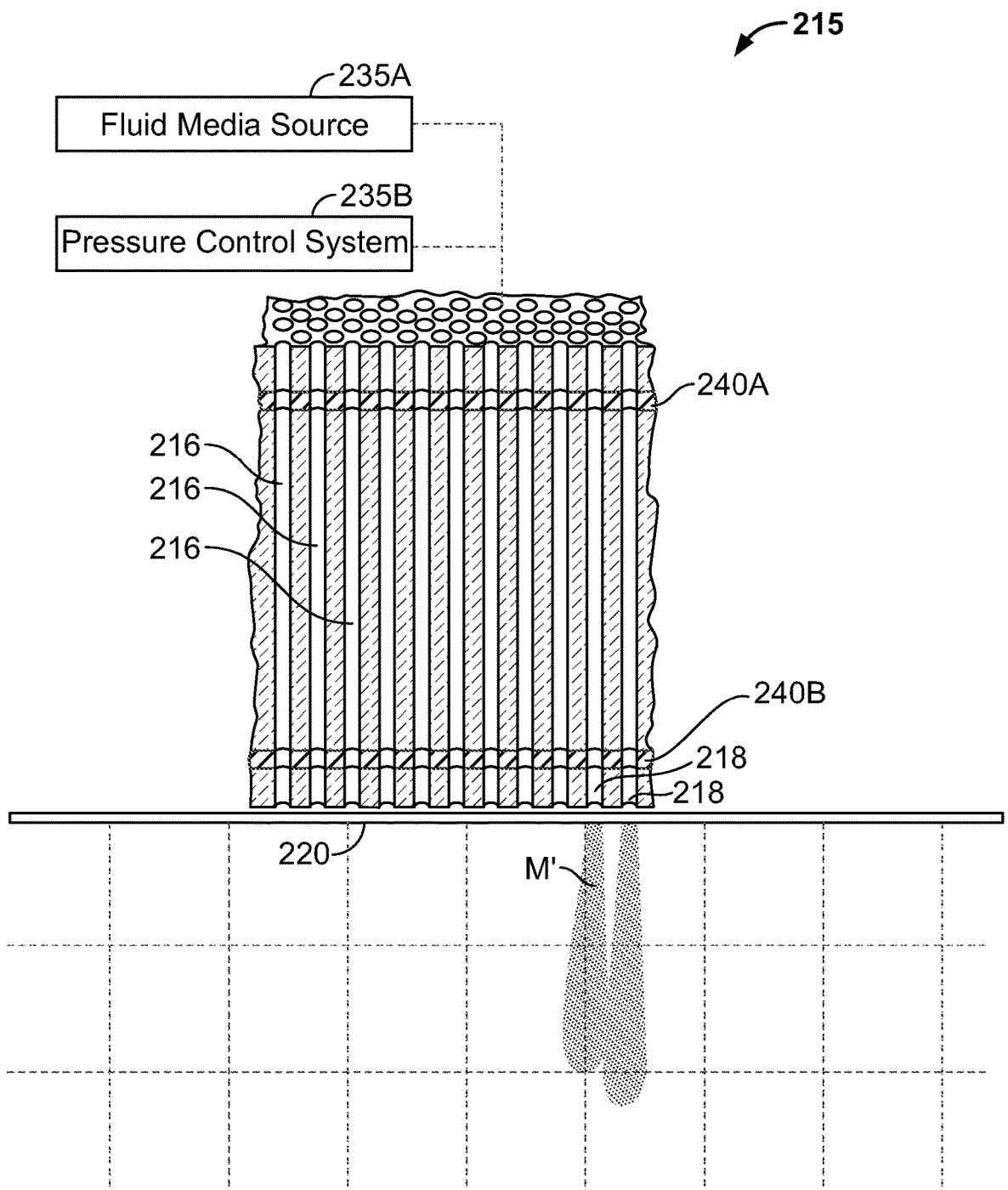
FIG. 13 is a greatly enlarged sectional view of the microchannel structure of FIG. 12 depicting the electrode arrangement carried therein.

In FIG. 12, it can be seen that the microchannel body 215 comprises a structure of an electrically insulative material (or a conductive material with an insulative coating) that defines open flow passageways or channels 216 therethrough that have open terminations or ports 218 in the working surface 220. At an interior of the microchannel body 215, an intermediate region of the open flow channels 216 is exposed to first and second electrode elements 240A and 240B. The electrode elements 240A and 240B can be formed in a plates or layers of channeled material or trabecular material that extends transverse to passageways 216. Thus, the channels are exposed to surfaces of the electrode elements 240A and 240B interior of the working surface 220 that interfaces with the targeted tissue T. As depicted in FIG. 13, electrical energy is applied between the electrodes to cause vaporization of the inflowing liquid media M which is converted to a vapor media M' within the interior of the channels 216 for ejection from the working surface 220 to interact with tissue as described above.

A working end similar to that of FIGS. 11-12 can be used in various thermotherapy procedures. For example, a rigid probe can be used in orthopedic procedures to cause hydrothermal shrinkage of collagen, for example in a spinal disc, or a joint capsule to stabilize the joint (see U.S. patent application Ser. No. 09/049,711 filed Mar. 27, 1998, incorporated herein by this reference). In an arthroscopic procedure, the working end is painted across a targeted tissue site in a joint capsule to shrink tissue. In another procedure, the working end may be stabilized against any collagenous tissue to heat and shrink collagen in a targeted tissue such as a herniated disc. In another procedure, the working end can be painted across the surface of a patient's esophagus to ablate abnormal cells to treat a disorder known as Barrett's esophagus. As described previously, the thermal energy delivery means of the invention preferably uses an electrical energy source and spaced apart electrodes for flash vaporization of a liquid media. It should be appreciated that a resistive element coupled to an electrical source also can be used. For example, a resistive element can fabricated out of any suitable material such a tungsten alloy in a helical, tubular or a microporous form that allows fluid flow therethrough.

Figure 14:
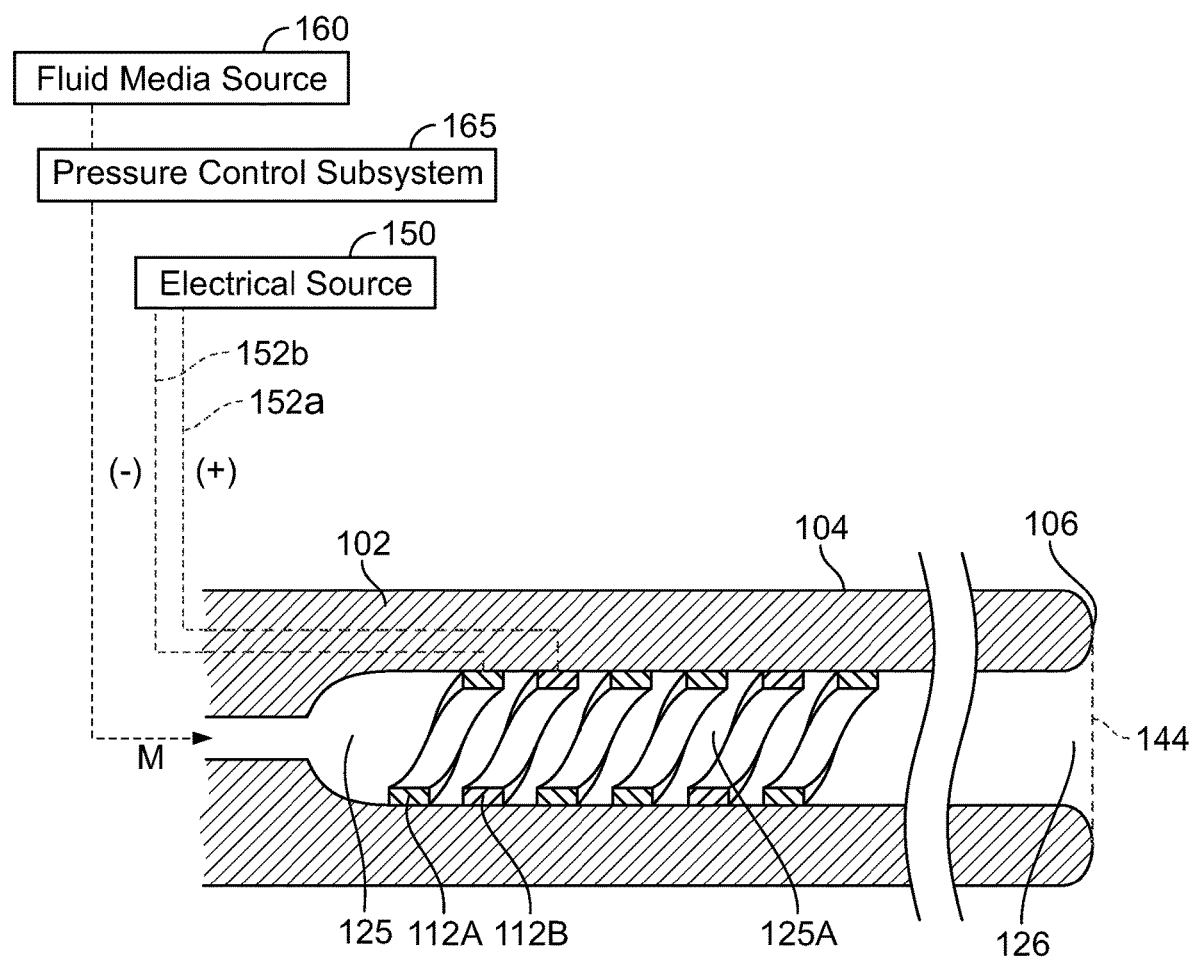
FIG. 14 is a schematic sectional view of an alternative working end with a helical electrode arrangement in the interior chamber.
Figure 15:
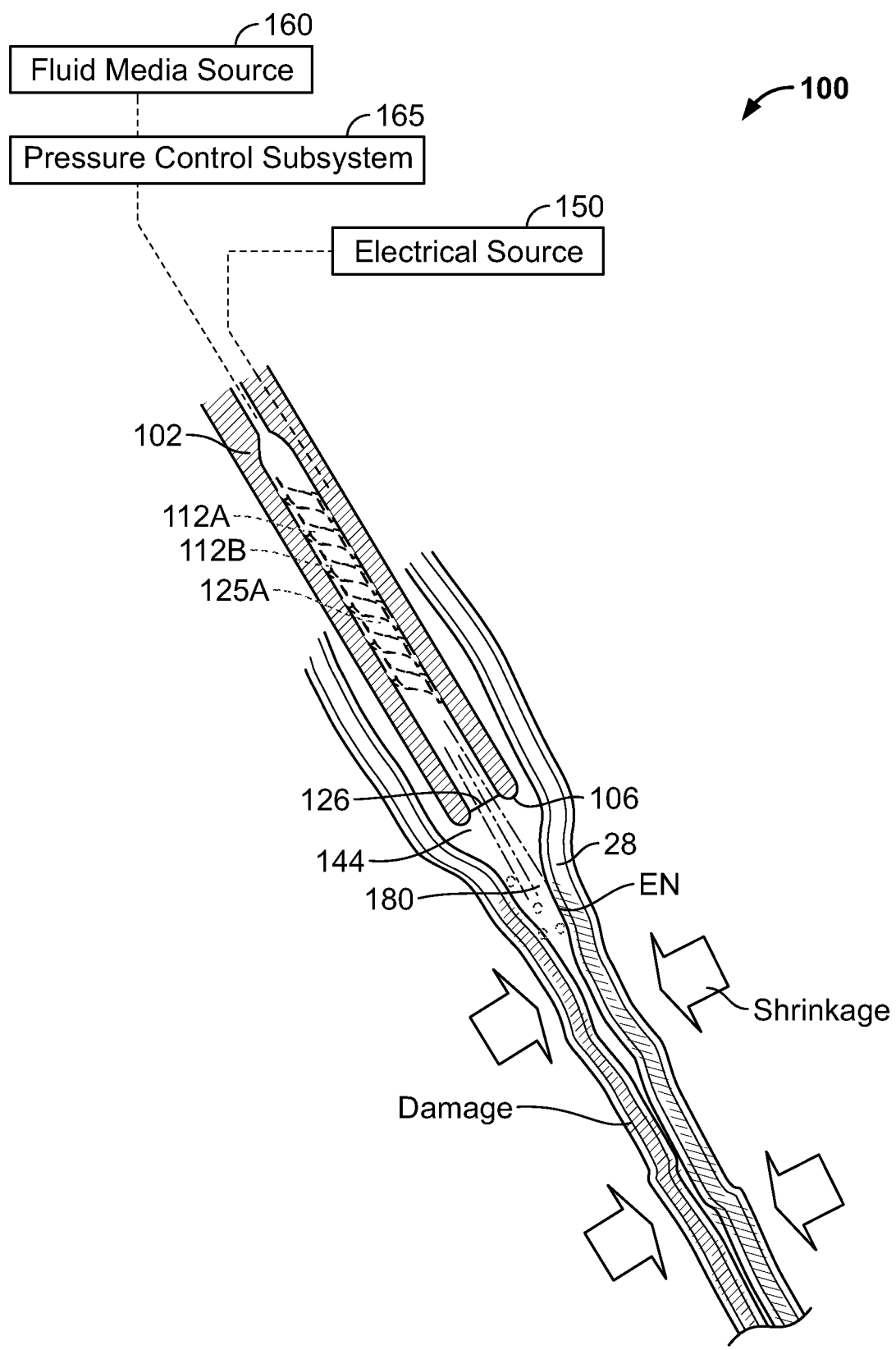
FIG. 15 illustrates a method of the invention in treating a blood vessel disorder with the device of FIG. 14.

Now referring to FIGS. 14 and 15, another embodiment of instrument working end 300 is shown in schematic sectional view. The previous devices were shown and optimized for having a working surface that engages tissue, and for controlling and limiting thermal effects in engaged tissue. In the embodiment of FIG. 14, the working end is adapted for controlled application of energy by means of phase change energy release in an endovascular application, or in media within or about other body lumens, ducts and the like.

FIG. 14 illustrates the working end 300 of a member or catheter body 305 that is dimensioned for introduction into a patient's vasculature or other body lumen. The diameter of body 305 can range from about 1 Fr. to 6 Fr. or more. The working end 300 typically is carried at the distal end of a flexible catheter but may also be carried at the distal end of a more rigid introducer member. In a rigid member, the working end also can be sharp for penetrating into any soft tissue (e.g. a fibroid, breast lesion or other organ such as a prostate) or into the lumen of a vessel.

The working end 300 of FIG. 14 has an interior chamber 310 again in communication with fluid media inflow source 335A and pressure control system 335B. The interior chamber 310 carries opposing polarity electrodes 315A and 315B as thermal energy emitters. The distal terminus or working surface 320 of the catheter has media entrance port 322 therein. In this embodiment, the electrodes 315A and 315B are spaced apart, indicated with (+) and (−) polarities coupled to electrical source 355, and are of a flexible material and configured in an intertwined helical configuration to provide a substantially large surface area for exposure to inflowing fluid media M. The electrodes can extend axially from about 1 mm to 50 mm and are spaced well inward, for example from 1 mm to 100 mm from the distal working surface 320. This type of electrode arrangement will enhance energy delivery to the liquid media M to allow effective continuous vaporization thereof. The lumen or chamber portion between electrodes 315A and 315B allows for focused energy application to create the desired energy density in the inflowing media M to cause its immediate vaporization. The vapor is then propagated from the working surface 320 via port 322 to interact with the endoluminal media. It should be appreciated that the instrument may have a plurality of media entrance ports 322 in the working surface, or additionally the radially outward surfaces of the catheter.

In the system embodiment of FIG. 14, the electrodes 315A and 315B are coupled to electrical source 355 by leads 356a and 356b. The working end 300 also is coupled to fluid media source 335A that carries pressurization means of any suitable type together with a pressure control system indicated at 335B.

In FIG. 15, the method of the invention is shown graphically wherein the distal end 300 is introduced into vasculature for the purpose of creating thermal effects in the vessel walls 360. In one targeted endovascular procedure, as depicted in FIG. 15, the objective is to apply controlled thermal energy to tissue to shrink and/or damage vessel walls to treat varicose veins. Most endothelial-lined structures of the body, such as blood vessel and other ducts, have substantially collagen cores for specific functional purposes. Intermolecular cross-links provide collagen connective tissue with unique physical properties such as high tensile strength and substantial elasticity. A well-recognized property of collagen relates to the shrinkage of collagen fibers when elevated in temperature to the range 60° to 80° C. Temperature elevation ruptures the collagen ultrastructural stabilizing cross-links, and results in immediate contraction in the fibers to about one-third of their original longitudinal dimension. At the same time, the caliber of the individual collagen fibers increases without changing the structural integrity of the connective tissue.

As represented in FIG. 15, the delivery of energy from the electrodes 315A and 315B to an inflow of liquid media M, such as any saline solution, will cause its instant vaporization and the expansion of the vapor (in addition to pressure from pressure source 335B) will cause high pressure gradients to propagate the heated vapor from port 322 to interact with endovascular media. The pressurized fluid media source 335A and pressure control subsystem 335B also can be adapted to create a pressure gradient, or enhance the pressure gradients caused by vapor expansion, to controllably eject the heated vapor from the working surface 320. As depicted in FIG. 15, the vaporized media M' deposits energy to the vessel walls in the vapor to liquid phase change energy release. The vaporized media is at about 100° C. as it crosses the interface between the working surface 320 and blood and will push the blood distally while at the same time causing the desired thermal effects in the vessel wall 360.

As shown in FIG. 15, the collagen in the vessel walls will shrink and/or denature (along with other proteins) to thereby collapse the vessel. This means of applying thermal energy to vessel walls can controllably shrink, collapse and occlude the vessel lumen to terminate blood flow therethrough, and offers substantial advantages over alternative procedures. Vein stripping is a much more invasive treatment. Rf closure of varicose veins is known in the art. Typically, a catheter device is moved to drag Rf electrodes along the vessel walls to apply Rf energy to damage the vessel walls by means of causing ohmic heating. Such Rf ohmic heating causes several undesirable effects, such as (i) creating high peak electrode temperatures (up to several hundred degrees C.) that can damage nerves extending along the vessel's exterior, (ii) causing non-uniform thermal effects about valves making vessel closure incomplete, and (iii) causing vessel perforations as the catheter working end is dragged along the vessel walls. In contrast, the energy delivery system of the invention utilizes the heat of a vapor media that cannot exceed about 100° C. (or slightly higher depending on pressure) to apply energy to the vessel walls. This method substantially prevents heat from being propagated heat outwardly by conduction—thus preventing damage to nerves. There is no possibility of causing ohmic heating in nerves, since a principal advantage of the invention is the application of therapeutic heat entirely without electrical current flow in tissue. Further, the vapor and its heat content can apply substantially uniform thermal effects about valves since the heat transfer mechanism is through a vapor that contacts all vessel wall surfaces—and is not an electrode that is dragged along the vessel wall. In one method of the invention, the vapor M' can be propagated from working end 300 while maintained in a single location. Thus, the system of the invention may not require the navigation of the catheter member 305 through tortuous vessels. Alternatively, the working end 300 may be translated along the lumen as energy is applied by means of vapor-to-liquid energy release.

Another advantage of the invention is that the system propagates a therapeutic vapor media M' from the working surface 320 that can be imaged using conventional ultrasound imaging systems. This will provide an advantage over other heat transfer mechanisms, such as ohmic heating, that cannot be directly imaged with ultrasound.

Another embodiment of the invention is shown in FIGS. 16-19 and is adapted for enhancing energy application to tissue by phase change energy releases in more precise tissue treatments, or to treat only surface layers of tissue. For example, the inventive system can be carried in a probe working end as in FIGS. 16 and 17 for applying thermal energy to a limited depth in a skin treatment. Alternatively, the system can be used in forceps as in FIG. 18 that is suited for neurosurgery and other precise surgeries for coagulating tissue while insuring that tissue sticking cannot occur.

In general, this embodiment includes (i) a polymeric monolith with microfluidic circuitry at an interior of the engagement surface for controlling the delivery of energy from the fluid to the engaged tissue; (ii) optional contemporaneous cooling of the microfluidic circuitry and engagement surface for controlling thermal effects in tissue; and (iii) optional coupling of additional Rf energy to the fluid media contemporaneous with ejection from the engagement surface to enhance energy application at the tissue interface.

Figure 16:
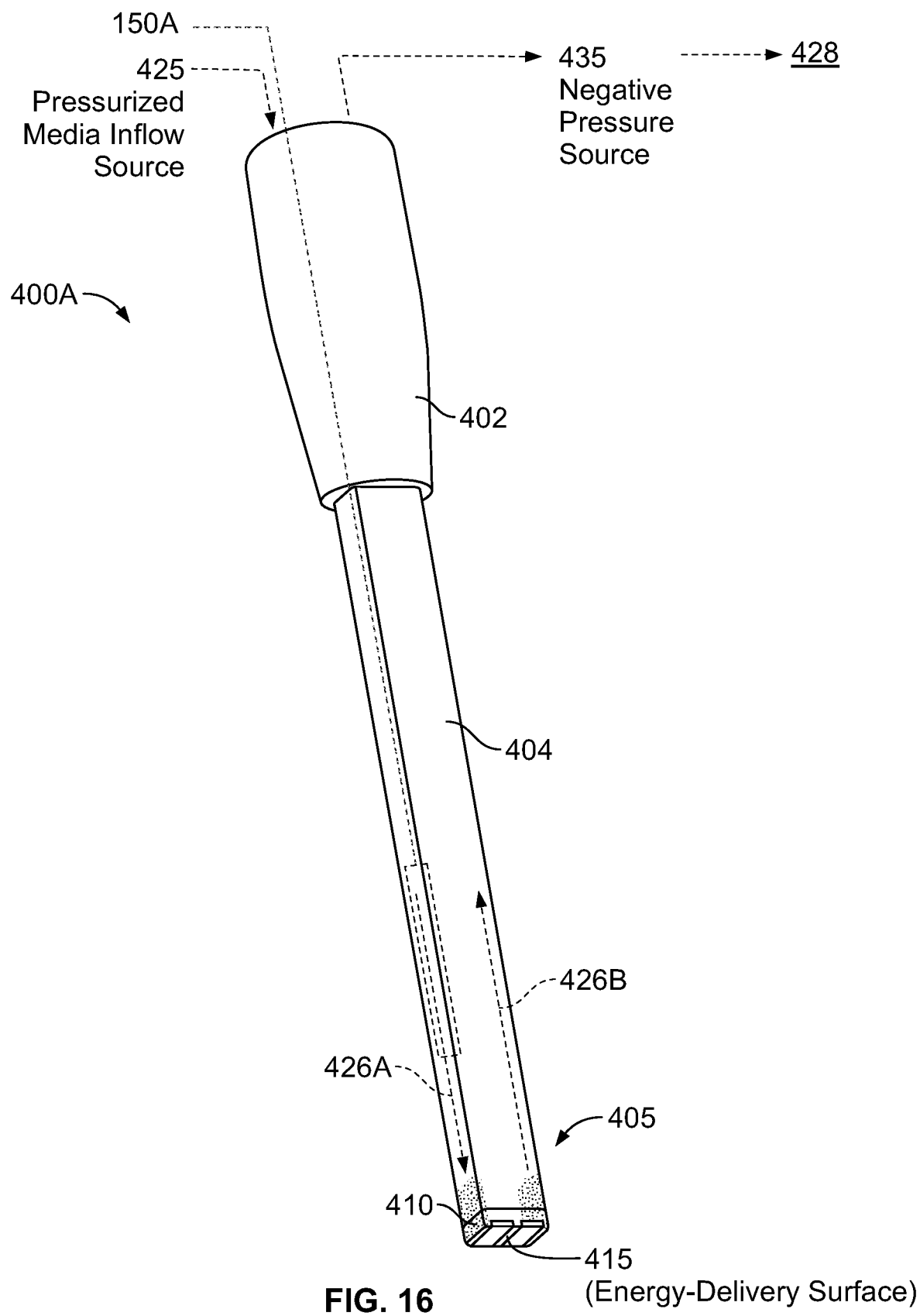
FIG. 16 illustrates a probe-type medical instrument that carries a tissue-engaging surface comprising a polymeric monolith with microfluidic interior channels that carry an energy-delivery fluid media.
Figure 17:
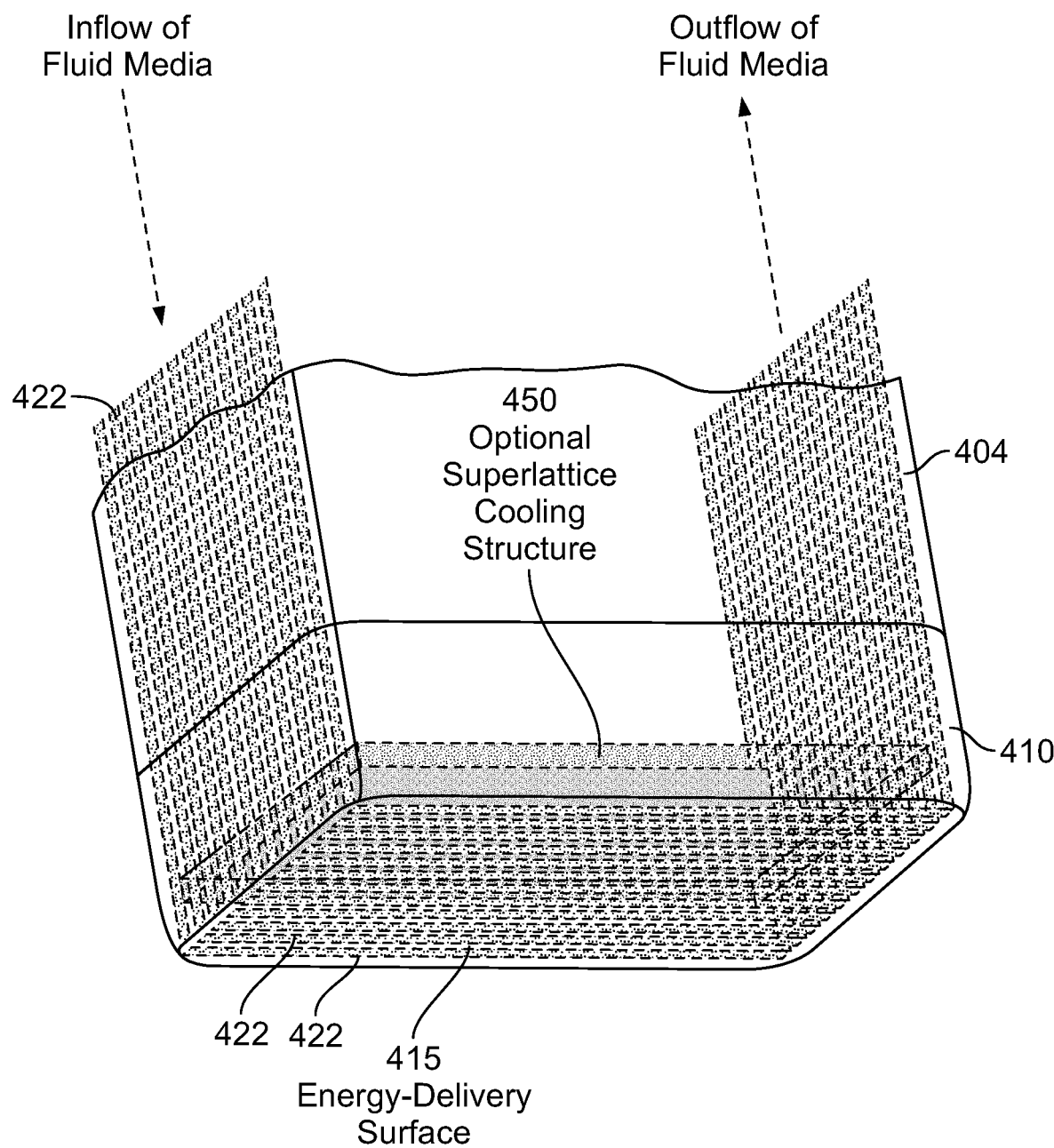
FIG. 17 illustrates an enlarged view of the working end of the instrument of FIG. 16.

FIGS. 16 and 17 illustrate a probe-type instrument 400A corresponding to the invention that is adapted for microscale energy delivery to tissue, such as a patient's skin. More in particular, the instrument 400 has a handle portion 402 and extension portion 404 that extends to working end 405. The working end carries a polymer microfluidic body 410 with an engagement surface 415 for engaging tissue. The engagement surface 415 can be flat or curved and have any suitable dimension. Its method of use will be described in more detail below.

Figure 18:
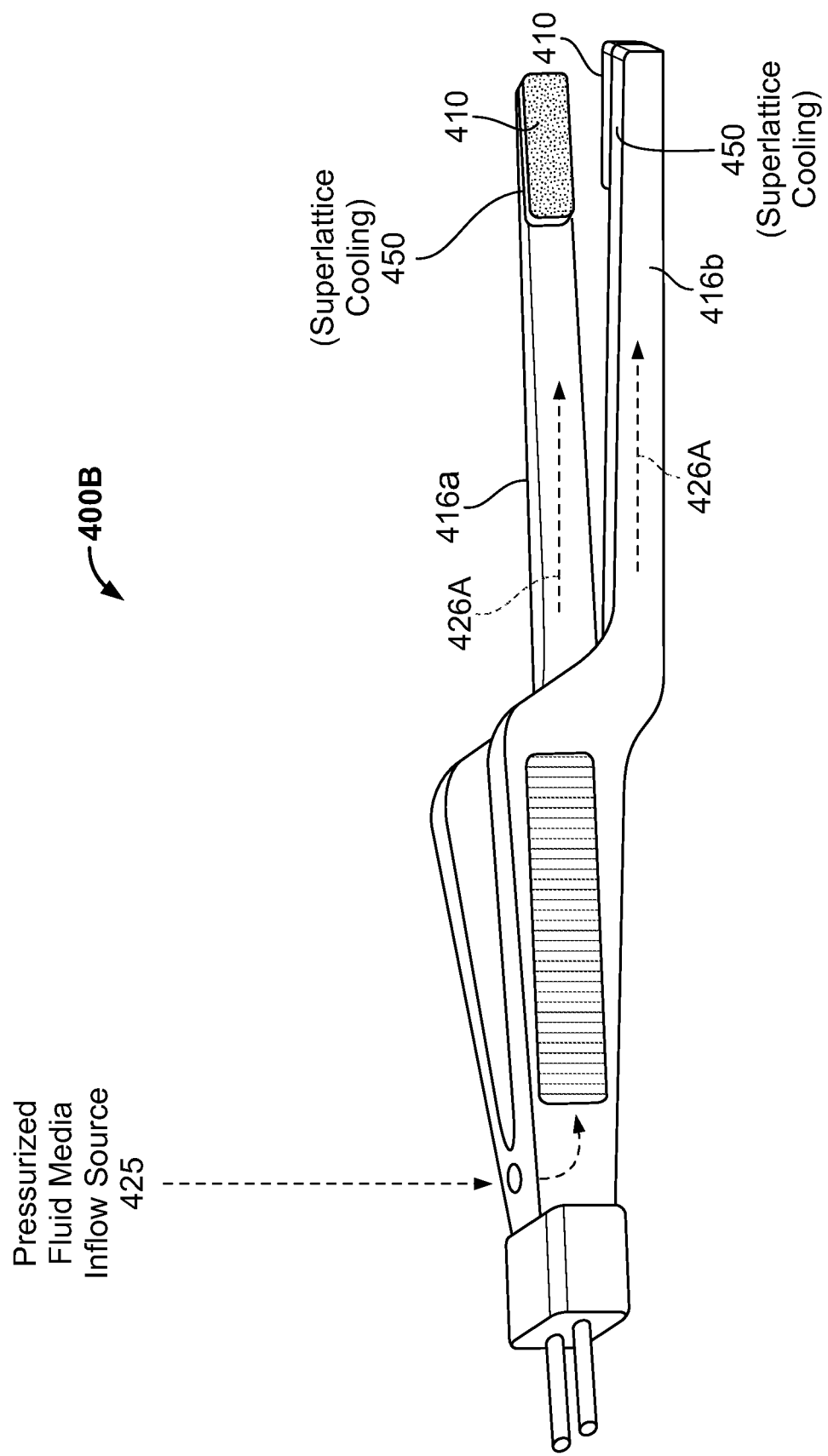
FIG. 18 is a view of a forceps-type instrument that carries a tissue-engaging surface similar to that of FIGS. 16 and 17 comprising a polymeric monolith with microfluidic channels for applying energy to tissue.

FIG. 18 illustrates a forceps-type instrument 400B having a configuration that is common in neurosurgery instruments. The instrument of FIG. 18 has first and second tines or jaw elements 416a and 416b wherein at least one jaw carries a microfluidic body 410 having an engagement surface 415 for engaging tissue. It should be appreciated that the jaws can have any suitable dimensions, shape and form.

Figure 19:
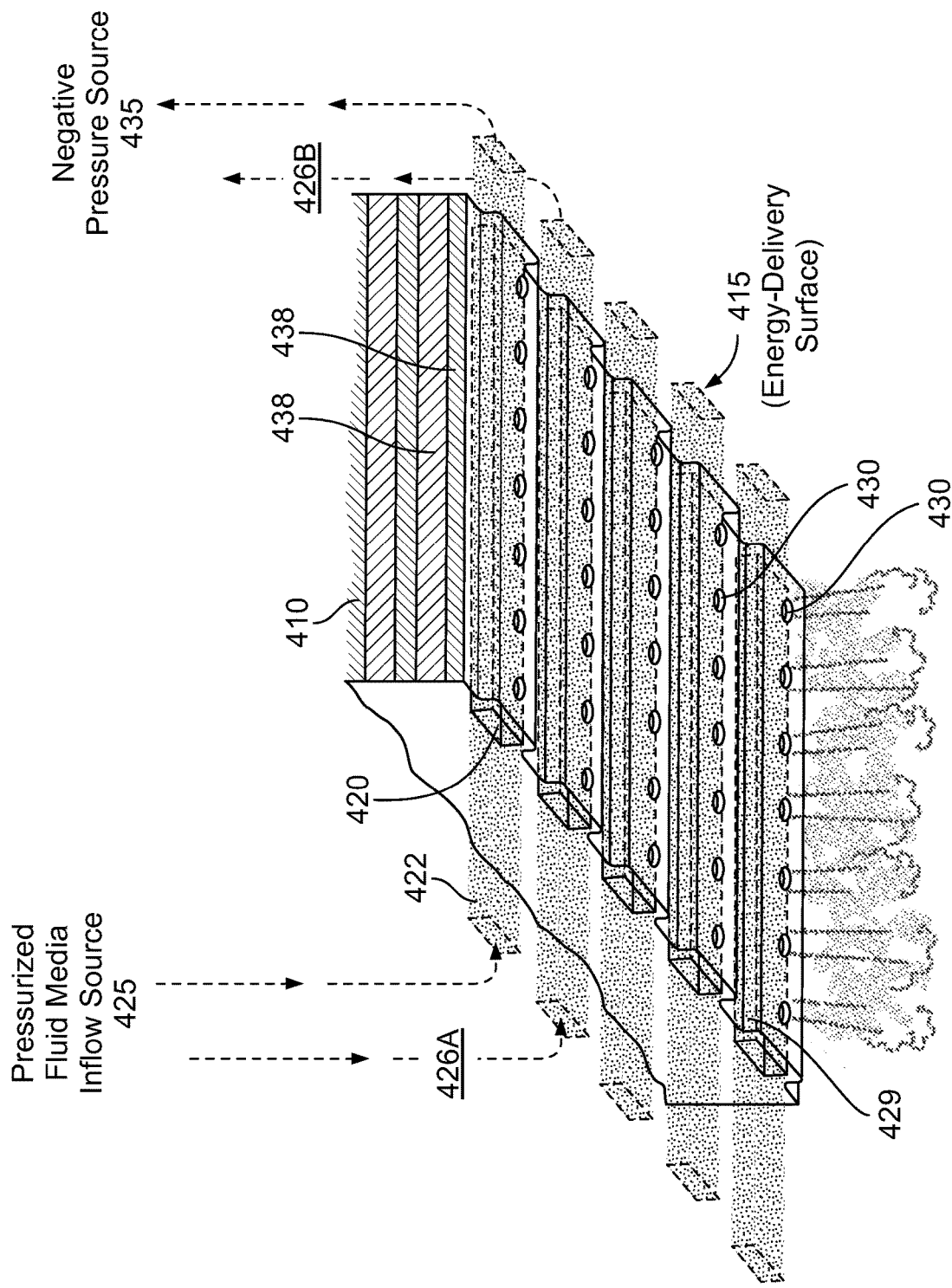
FIG. 19 is a greatly enlarged cut-away view of the tissue-engaging surface of FIGS. 17 and 18 with microfluidic interior channels that carry an energy-delivery vapor media adapted for release from outlets in the engagement surface.

Now referring to FIG. 19, a greatly enlarged view of body 410 and engagement surface 415 of FIGS. 17 and 18 is shown. In one aspect of the invention, the microfabricated body 410 carries microfluidic channels 420 adapted to carry a fluid media 422 from a pressurized media source 425 as described in previous embodiments. The media 422 is carried from source 425 by at least one inflow lumen 426A to the microfluidic channels 420 in body 410 (see FIGS. 16-18). In some embodiments, an outflow lumen 426B is provided in the instrument body to carry at least part of fluid 422 to a collection reservoir 428. Alternatively, the fluid 422 can move in a looped flow arrangement to return to the fluid media source 425 (see FIGS. 16-18). The engagement surface can be smooth, textured or having surface features for gripping tissue. In the embodiment of FIG. 19, the surface is provided with grooves 429 that provide a grip surface that is useful in jaw structures as in FIG. 18. The microfluidic channels have a mean cross section of less than 1 mm. Preferably, the channels have a mean cross section of less than 0.5 mm. The channels 420 can have any cross-sectional shape, such as rectangular or round that is dependent on the means of microfabrication.

FIG. 19 depicts one exemplary embodiment of engagement surface 415 that further carries a large number of open terminations or ports 430 in the surface for permitting propagation of vapor phase media 422 from the ports 430. In this aspect of the invention, the system applies energy to tissue as described in the earlier embodiments (see FIGS. 6A-6B and 11-14). The microfluidic channels 420 extend in any suitable pattern or circuitry from at least one inflow lumen 426A. The system can be designed to eject 100% of the vapor phase media from the ports 430 for thermal interaction with tissue. In a preferred embodiment, the microfluidic channels 420 extend across the engagement surface 415 and then communicate with at least one outflow lumen 426B (see FIGS. 16 and 17). In the embodiment of FIG. 19, the ejection of vapor media through ports 430 then can be modulated by both inflow pressures and by suction from the optional negative pressure source 435 coupled to the outflow lumen 426B (see FIGS. 16 and 17). The flow channels 420 further can have an increase in cross-sectional dimension proximate the surface 415 or proximate each port 430 to allow for lesser containing pressure on the vapor to assist in its vapor to liquid phase transition.

In another embodiment, the engagement surface can have other suction ports (not shown) that are independent of the fluidic channels 420 for suctioning tissue into contact with the engagement surface 415. A suction source can be coupled to such suction ports.

In the embodiment of FIGS. 17 and 18, the system includes an electrical source 355 and fluid media source 355A as described above for converting a liquid media to a vapor media in a handle or extension portion, 402 or 404, of the instrument. The system further has a fluid pressure control system 335B for controlling the media inflow pressures as in the embodiment of FIGS. 14-16.

Of particular interest, the microfabricated body 410 can be of an elastomer or other suitable polymer of any suitable modulus and can be made according to techniques based on replication molding wherein the polymer is patterned by curing in a micromachined mold. A number of suitable microfabrication processes are termed soft lithography. The term multilayer soft lithography combines soft lithography with the capability to bond multiple patterned layers of polymers to form a monolith with fluid and electric circuitry therein. A multilayer body 410 as in FIGS. 19 and 20 can be constructed by bonding layers 438 of a selected polymer, each layer of which is separately cast from a micromachined mold. An elastomer bonding system can be a two component addition-cure of silicone rubber typically.

The scope of the invention encompasses the use of multilayer soft lithography microfabrication techniques for making thermal vapor delivery surfaces and electrosurgical engagement surfaces, wherein such energy delivery surfaces consist of multiple layers 438 fabricated of soft materials with microfluidic circuitry therein as well as electrical conductor components.

In an optional embodiment illustrated in FIG. 20, as will be further described below, the microfluidic circuitry further carries electrodes 440A and 440B for coupling electrical energy to a conductive fluid 422 that flows within the microchannels 420. Multilayer soft lithographic techniques for microfluidics are described, in general, in the following references which are incorporated herein by this reference: Marc A. Unger, Hou-Pu Chou, Todd Thorsen, Axel Scherer, and Stephen R. Quake, "Monolithic Microfabricated Valves and Pumps by Multilayer Soft Lithography" (http://thebig-one.caltech.edu/quake/publications/scienceapr0-0.pdf) and Younan Xia and George M. Whitesides, "Soft Lithography", (http://web.mit.edu/10.491/softlithographyreview.pdf).

In any embodiment of polymer body 410, as described above, the layers 438 can be microfabricated using soft lithography techniques to provide an open or channeled interior structure to allow fluid flows therethrough. The use of resilient polymers (e.g., silicone) is preferred and the more particular microfabrication techniques include any of the following. For example, microtransfer molding is used wherein a transparent, elastomeric polydimethylsiloxane (PDMS) stamp has patterned relief on its surface to generate features in the polymer. The PDMS stamp is filled with a prepolymer or ceramic precursor and placed on a substrate. The material is cured and the stamp is removed. The technique generates features as small as 250 nm and is able to generate multilayer body 410 as in FIG. 19. Replica molding is a similar process wherein a PDMS stamp is cast against a conventionally patterned master. A polyurethane or other polymer is then molded against the secondary PDMS master. In this way, multiple copies can be made without damaging the original master. The technique can replicate features as small as 30 nm. Another process is known as micromolding in capillaries (MIMIC) wherein continuous channels are formed when a PDMS stamp is brought into conformal contact with a solid substrate. Then, capillary action fills the channels with a polymer precursor. The polymer is cured and the stamp is removed. MIMIC can generate features down to 1 μm in size. Solvent-assisted microcontact molding (SAMIM) is also known wherein a small amount of solvent is spread on a patterned PDMS stamp and the stamp is placed on a polymer, such as photoresist. The solvent swells the polymer and causes it to expand to fill the surface relief of the stamp. Features as small as 60 nm have been produced. A background on microfabrication can be found in Xia and Whitesides, Annu. Rev. Mater. Sci. 1998 28:153-84 at p. 170 FIG. 7d (the Xia and Whitesides article incorporated herein by reference). In any embodiment of polymer body 410, the polymer can have a "surface modification" to enhance fluid flows therethrough, and at the exterior surface to prevent the possibility of adherence of body materials to the surfaces. For example, the channels can have ultrahydrophobic surfaces for enabling fluid flows, and the fluids or surfaces can carry any surfactant.

In a working end embodiment that is particularly adapted for microsurgery, as in the forceps of FIG. 18, the microfluidic body 410 with engagement surface 415 is substantially thin and is coupled to superlattice thermoelectric cooling means indicated at 450. Thus, the scope of the invention extends to two complementary novel structures and components: (i) bipolar microfluidic, flowable electrodes, and (ii) a superlattice cooling structure. The components will be described in order.

Figure 20:
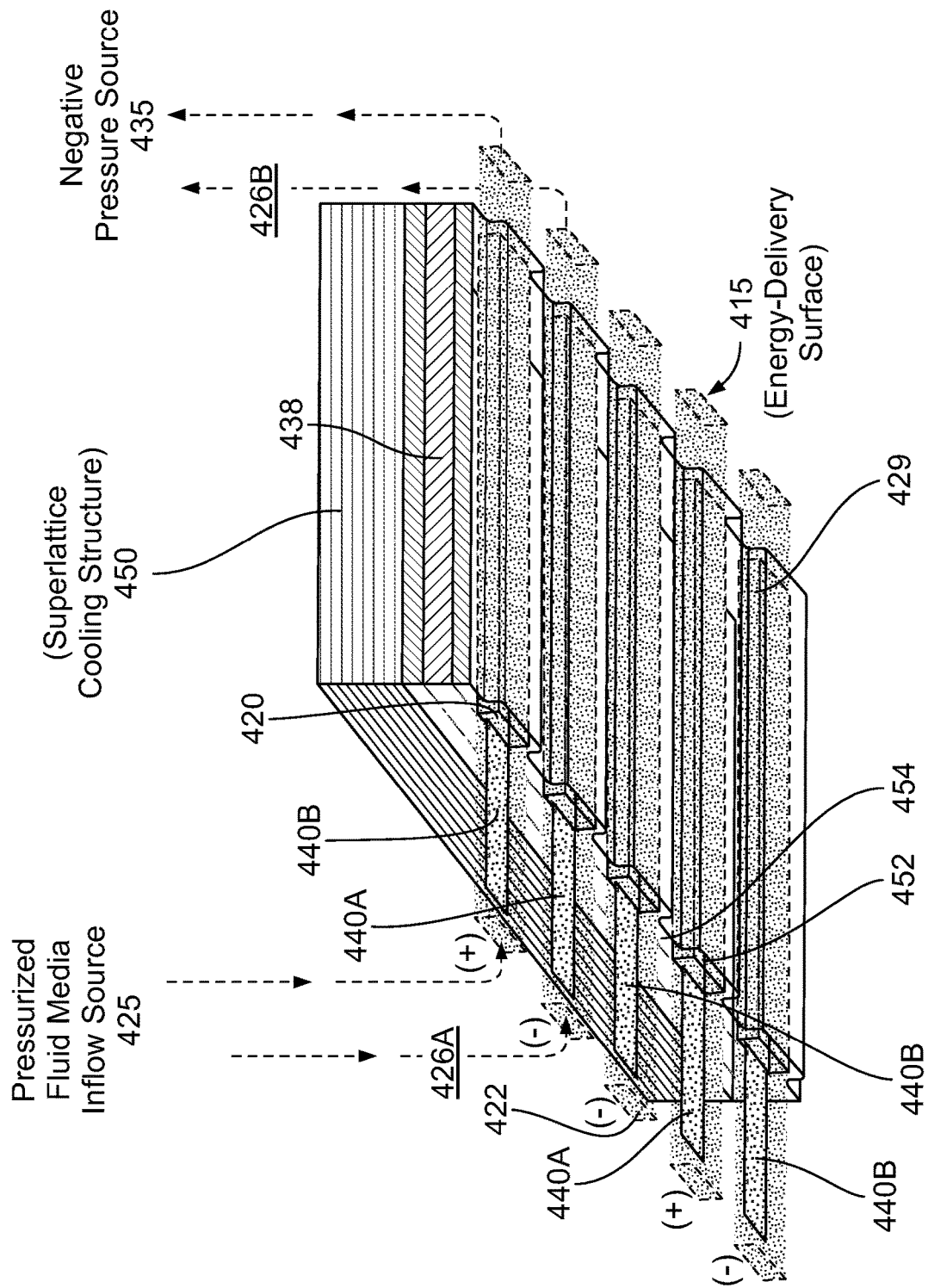
FIG. 20 is a cut-away view of an alternative tissue-engaging surface similar to FIG. 19 with microfluidic interior channels that carry a flowing conductive liquid media for coupling energy to tissue in a bi-polar mode.
Figure 21A:
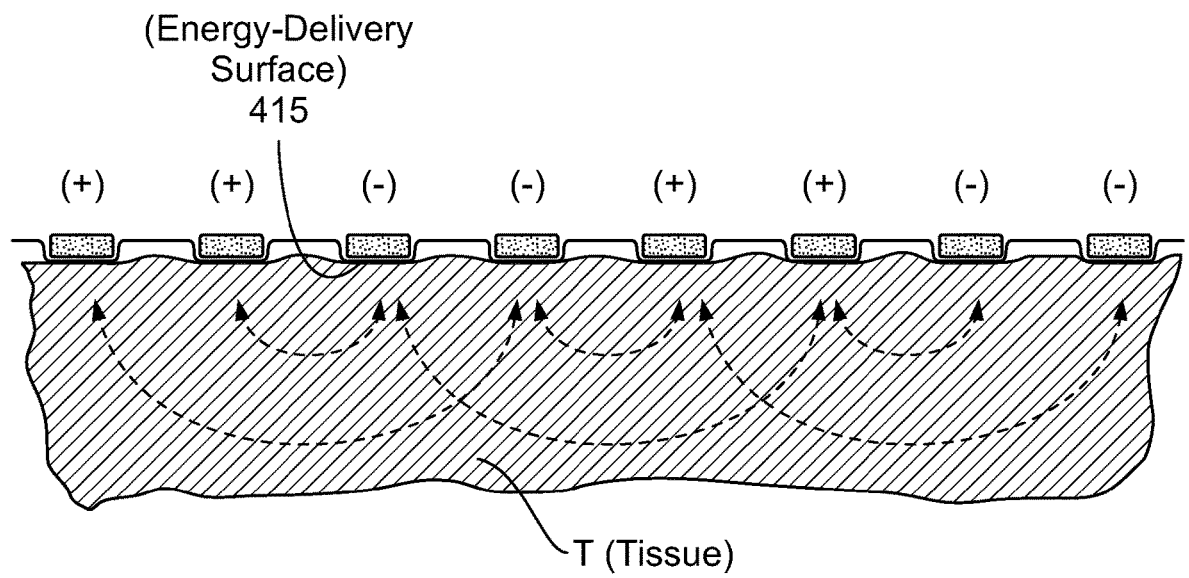
FIGS. 21A-21B illustrate the tissue-engaging surface of FIG. 20 with electrical circuitry adapted to alter the polarity of groups of fluidic channels that each carry a flowing conductive liquid media.
Figure 21B:
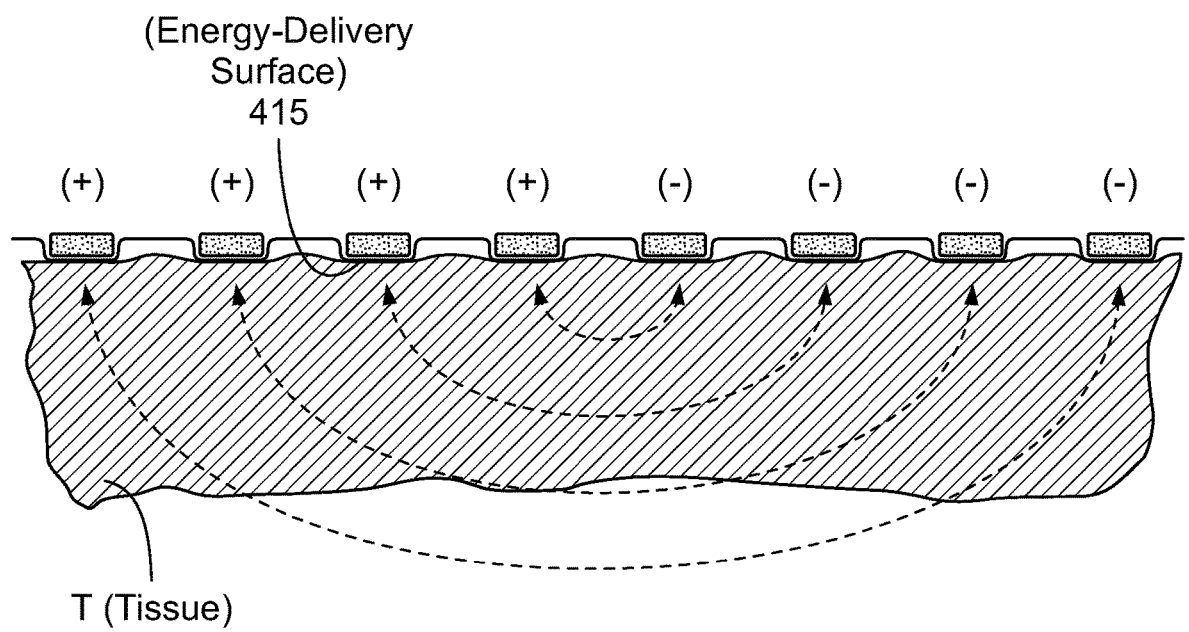

FIGS. 20 and 21A-21B illustrate the microfluidic body 410 with channels 420 that carry a flowing conductive fluid 422 such as hypertonic saline. The fluid 422 is delivered in a liquid form to the forceps schematically shown in FIG. 18. The fluid remains in a liquid state as it cycles through channels 420 of the engagement surface 410 as in FIG. 20. The microfluidic body 410 can be adapted to delivery energy in either a monopolar or bipolar mode. In a monopolar mode, radiofrequency energy is coupled to the flowing fluid 422 by an active electrode arrangement having a single polarity, wherein the targeted tissue is treated when an electrical circuit is completed with a ground pad comprising a large area electrode coupled to the patient at a location remote from the targeted tissue. In a bipolar mode, radiofrequency energy is coupled to flowing fluid 422 by first and second opposing polarity electrodes 440A and 440B in different channels 420, or different groups of channels (see FIG. 20).

In FIG. 20, the polymeric body 410 carries electrodes 440A and 440B having exposed surfaces in the interior of channels 420 for coupling electrical energy to the conductive fluid 422. The surface layer 452 of polymeric material overlying channels 420 is substantially thin and allows from capacitive coupling of electrical energy to engaged tissue. The polymer is selected from a class of material known in the art that optimizes the delivery of electrical energy therethrough, wherein the polymer has limited capacitance. The interior regions 454 of polymeric material between channels 420 has a greater dimension than the surface layer 452 to prevent substantial current flow between the channels at the interior of body 410. Also, the interior layer 456 that carries the channels can be microfabricated of a different substantially insulative polymer to prevent current flows in the interior of body 410 between the opposing polarity channels, indicated with (+) and (−) signs.

In FIG. 20, the body 410 is illustrated in a bipolar configuration with electrodes 440A and 440B comprising a microfabricated metal layer or a conductively doped polymer. The electrodes 440A and 440B alternatively can comprise conductive wires inserted into the channels or can be a conductive coating fabricated into the channel walls. Soft lithography methods also can deposit conductive layers or conductive polymers to provide the electrode functionality of the invention. Alternative means for fabricating channels with conductive coatings are described in the following patents to W. Hoffman et al., which are incorporated herein by reference: U.S. Pat. Nos. 6,113,722; 6,458,231; 6,194,066; 6,588,613; 6,059,011; 5,352,512; 5,298,298; and 5,011,566.

FIGS. 21A-21B illustrate the microfludic body 410 as in FIG. 20 with electrical circuitry for altering the polarity of electrodes to provides a first polarity to a first group of fluidic channels (indicated as (+) positive pole) and a provides the second opposing polarity to a second group of fluidic channels (indicated as (−) negative pole). By this means, the depth of ohmic heating in tissue can be adjusted as is known in the art. In a preferred embodiment, each conductive region or electrode is coupled to a controller and multiplexing system to allow bipolar energy application within engaged tissue between selected individual electrodes having transient opposing polarities, or any first polarity set of electrodes and fluidic channels 420 that cooperate with any set of second polarity electrodes and channels. The system can have independent feedback control based on impedance or temperature for each activated set of electrodes. In this embodiment, the polymer layer overlying the channel also can be microporous or macroporous to allow the conductive fluid 422 to seep through this fluid permeable layer to directly couple electrical energy to the engaged tissue.

Now turning to the superlattice cooling component 450 of the invention, it can be seen in FIGS. 17, 18 and 20 that the superlattice component can be carried interior of body 410 and engagement surface 415. As described above, one preferred nanolattice cooling system was disclosed by Rama Venkatasubramanian et al. in U.S. patent application Ser. No. 10/265,409 (Published Application No. 20030099279 published May 29, 2003) which is incorporated herein by reference. For convenience, this class of thin, high performance thermoelectric device is referred to herein for convenience as a superlattice cooling device.

Superlattice cooling devices provide substantial performance improvements over conventional thermoelectric structures, also known as Peltier devices. It has been reported that superlattice thermoelectric material having a surface dimension of about 1 cm$^2$ can provide 700 watts of cooling under a nominal temperature gradient. This would translate into an efficiency at least double that of conventional thermoelectric devices. The use of a superlattice cooling device in a surgical instrument further provides the advantage of wafer-scalability and the use of known processes for fabrication. The author first disclosed the use of thermoelectric cooling devices in a thermal-energy delivery jaw structure in U.S. Pat. No. 6,099,251 issued Aug. 8, 2000 (see Col. 21, lines 38-52).

In a typical embodiment, the thin-film superlattice cooling structure comprises a stack of at least 10 alternating thin semiconductor layers. More preferably, the superlattice structure includes at least 100 alternating layers, and can comprise 500 or more such nanoscale layers. In one embodiment, the thin film superlattice structure comprises alternating stacks of thin film layers of bismuth telluride and antimony telluride. The thin film superlattice structure thus comprises a circuit including a plurality of thin film layers of at least two dissimilar conductors wherein current propagates heat toward one end of the circuit thereby cooling the end of the circuit coupled to the energy-emitting surface. The superlattice cooling structures are coupled to an electrical source by independent circuitry, and can also be coupled with a control system to operate in a selected sequence with thermal energy delivery.

Figure 22A:
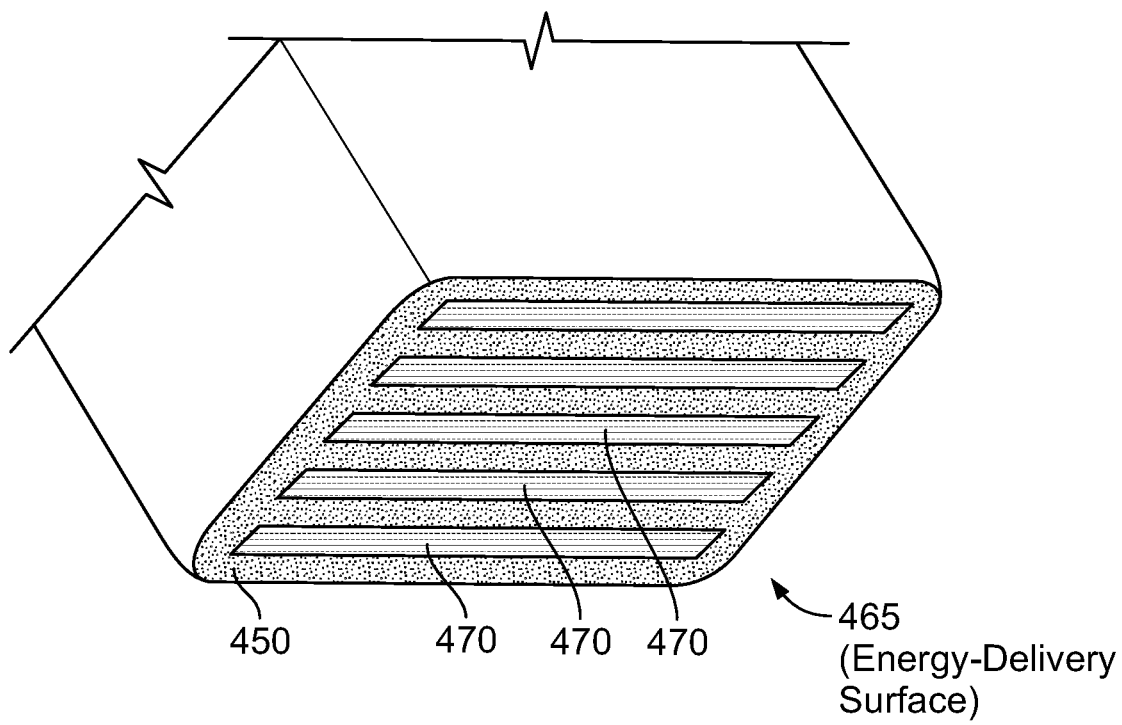
FIGS. 22A-22B are view of exemplary tissue-engaging surfaces that includes first surface portions of a superlattice cooling structure and second surface portions of a thermal-energy emitter.
Figure 22B:
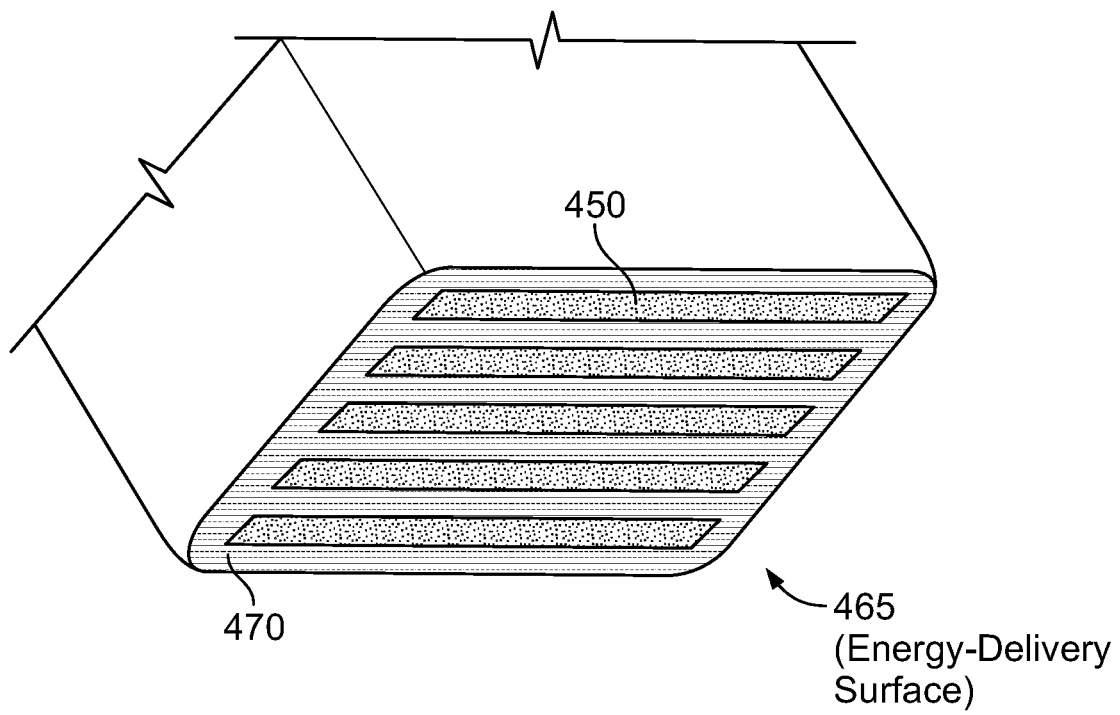
Figure 23:
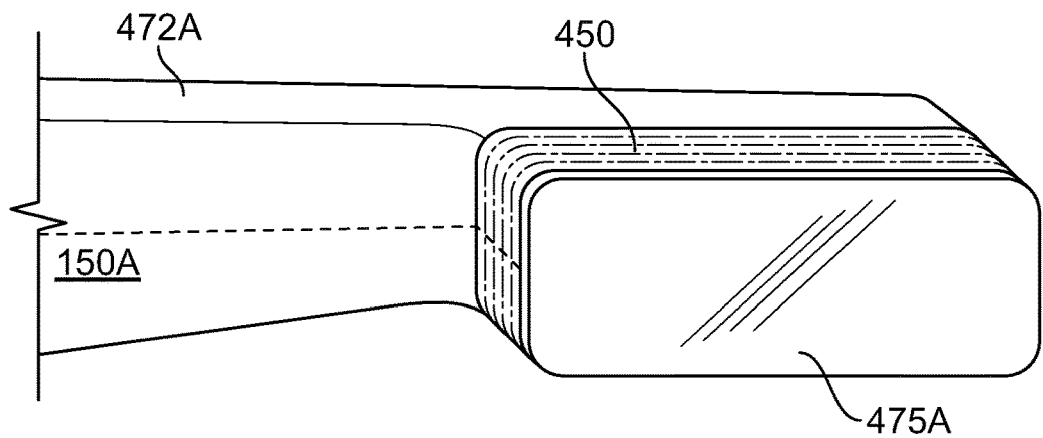
FIG. 23 is a view of a neurosurgery forceps jaw that includes a superlattice cooling structure together with a bipolar electrode.

Referring to FIGS. 22A-22B, the scope of the invention extends to a surgical energy-emitting surface 465 for applying energy to tissue wherein the superlattice cooling structure 450 is interior of the energy-emitting surface and/or adjacent to the energy-emitting surface for engaging and cooling tissue. A tissue-engaging surface can include a first surface portion 470 of a thermal energy emitter and second surface portion 450 of the superlattice cooling device as in FIGS. 22A and 22B. The first and second surface portions 470 and 450 can be provided in any suitable pattern. A working end as in FIGS. 22A and 22B can be used for treating skin, for example in cosmetic treatments for shrinking collagen or for damaging or stimulating subsurface tissues to thereby cause collagen formation. The system can deliver a burst of thermal energy followed by a surface cooling to localize heat at a selected depth while preventing excessive damage to the epidermal layer. In a preferred embodiment, the energy-emitting surface is thin microfluidic body 410 as depicted in FIG. 19 above. In another embodiment in FIG. 23, a jaw arms 472A that is of a forceps-type instrument as in FIG. 18, can comprise a bipolar metal film electrode 475A overlying a superlattice cooling structure 450. Each jaw arm can include such an electrode coupled to an Rf source 150A to provide for bipolar energy delivery between the jaws. Such a bi-polar jaw structure with active superlattice cooling would prevent tissue sticking. It should be appreciated that other thermal energy-emitting surfaces are possible, such as laser emitters, microwave emitters and resistive heating elements.

Figure 24:
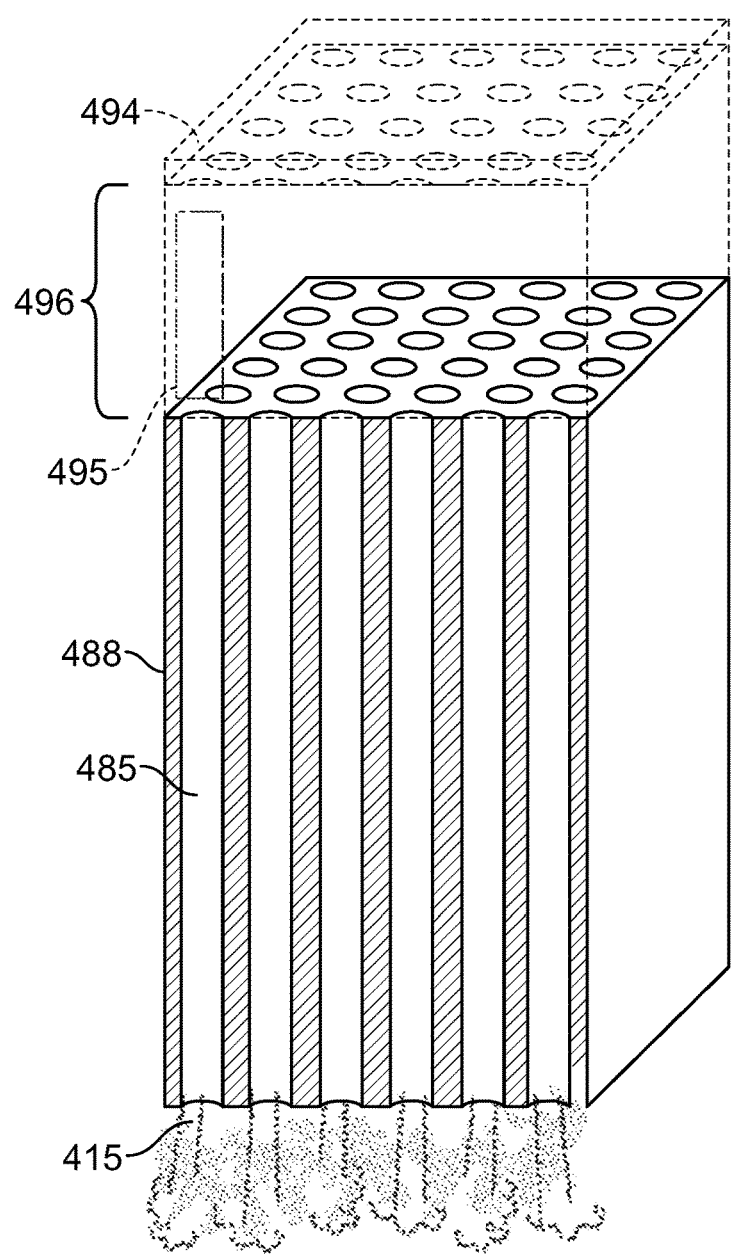
FIG. 24 is a cut-away view of an alternative tissue-engaging surface having microfluidic channels that utilize a capillary effect to draw a liquid media into the channels wherein electrical energy causes a liquid-to-vapor conversion and ejection of the vapor media from the engagement surface.

Now turning to FIG. 24, an alternative instrument with thermal energy delivery surface 415 is shown. In this embodiment, the open-ended capillary microchannels 485 are formed in a body 488 of a selected material and have a selected cross-sectional dimension to provide a capillary effect to draw liquid media 422 into the capillary channels. This embodiment can be fabricated of a polymer by soft lithography means. Alternatively, the tissue-engaging body can be of a ceramic, metal or a combination thereof. As can be seen in FIG. 24, the plurality of capillary channels have an interior end 492 that communicates with a liquid reservoir 494. In operation, the capillaries will draw liquid 422 into the channels by means of normal capillary forces. The capillary channels 485 further carry a thermal energy emitter about interior channel regions for vaporizing the liquid 422 that is drawn into the channels. The thermal energy emitter is operatively coupled to a source selected from the class consisting of a Rf source, microwave source, laser source and resistive heat source. In operation, the capillaries will draw liquid 422 into the channels 485 wherein vaporization will eject the vapor outwardly from the surface 415 to apply thermal energy to tissue as described in earlier embodiments. The advantage of the invention is that the capillary channels can continuously draw liquid 422 into the microchannels from a substantially static liquid reservoir without the need for a substantial pressurization means. At the same time, the vaporization of the liquid media 422 will cause pressures to cause ejection of the vapor from the surface 415 since that is the direction of least resistance. The surface 415 can further carry any monopolar of bipolar electrode arrangement to couple energy to the ejected vapor and engaged tissue.

Figure 25:
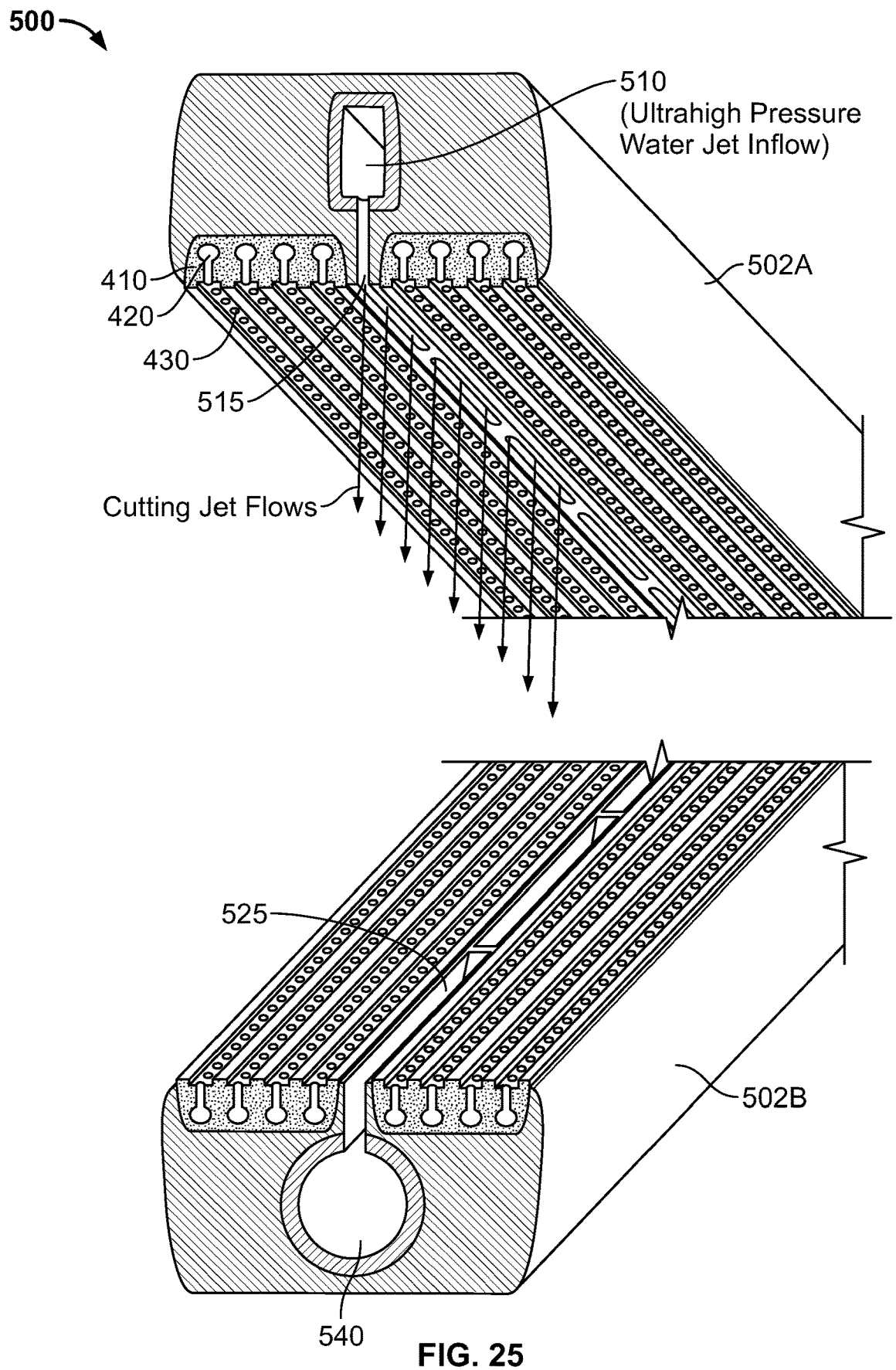
FIG. 25 illustrates a jaw structure that carries engagement surfaces with soft lithography microfabricated energy delivery surfaces of the invention together with very high pressure water jetting means for transecting sealed tissue.

FIG. 25 illustrates an alternative jaw structure 500 for sealing tissue with first and second jaws 502A and 502B. Each jaw carries a body 410 with capillaries channels 420 and vapor delivery ports as in FIG. 19. The jaws structure includes a system that transects tissue by hydrojet means that can cooperate with the fluid media source of the invention. Of particular interest, one jaw carries an ultrahigh pressure water inflow lumen 510 that exits at least one thin linear port 515 wherein the jetting of water has sufficient velocity to cut the engaged tissue. Depending on the length of the jaws, the jetting port(s) 515 can be singular or plural, an overlapping if required to insure transection of any engaged tissue volume. In another embodiment (not shown) the jaw can have a moveable jet member that axially translates in the jaw to cut tissue. Electrical energy can be coupled to a fluid jet to further apply energy along a cut line. The jetted fluid is received by elongate channel 525 in the opposing jaw that communicates with extraction lumen 540 and an aspiration source. Such a jaw can have an interlock mechanism to insure that the hydrojet cutting means can only be actuated when the jaws are in a closed position. This embodiment provides the advantage of having a non-stick tissue-sealing jaw structure together with a transecting means that operates without moving parts. It should be appreciated that the scope of the invention includes the use of such a hydrojet cutting means to any surgical jaw structure that is adapted to seal tissue or organ margins.

4. Type "D" Thermotherapy Device.

Figure 26:
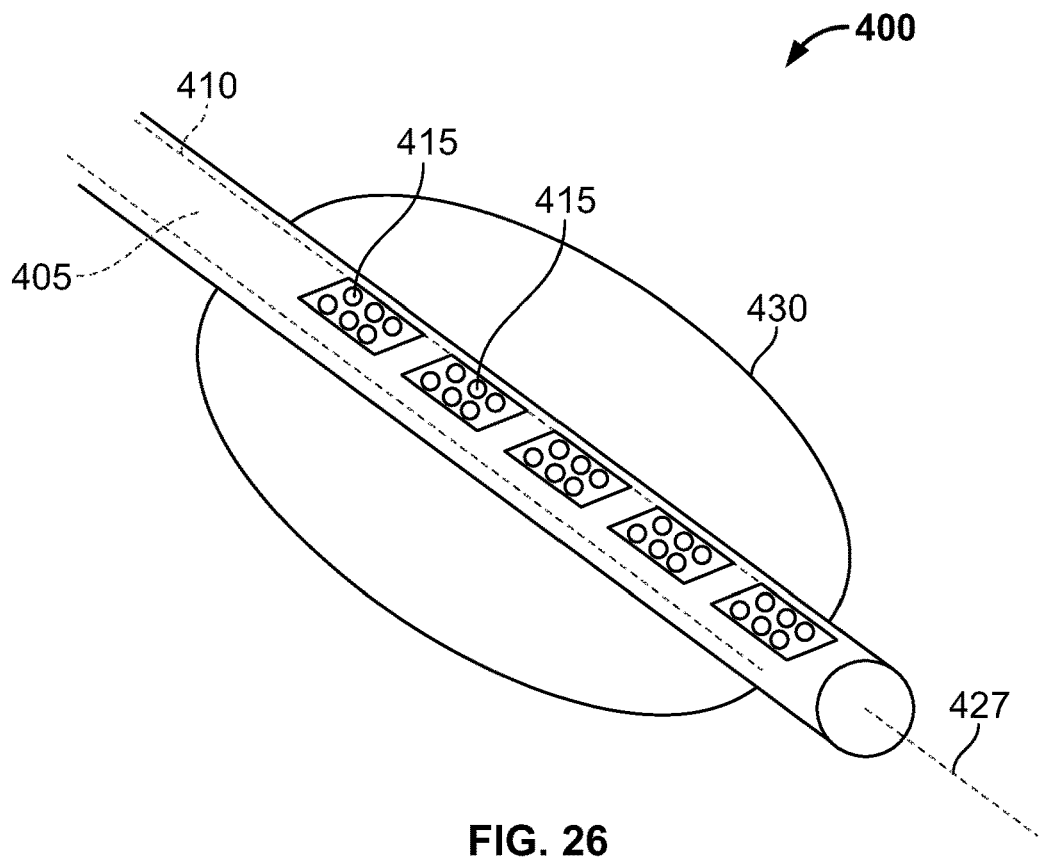
FIG. 26 is a perspective view of an alternative working end of a Type "D" embodiment with a plurality of microchanneled structures in a catheter.

FIG. 26 illustrates an alternative working end 400 carried by an elongate flexible catheter body 405 of the type used in interventional cardiology. The working end 400 carries at least one microchannel structure 415 in working surface 420 as described above or applying energy by pressing surface 420 against targeted tissue. FIG. 26 depicts a plurality of microchannel bodies or structures 415 in the sidewall of a catheter working end to allow for flexibility, with the catheter body 405 being from 1.0 to 2.0 mm in diameter (not limiting). The microchannel structure is oriented so that vapor media M' is ejected substantially transverse to the axis 427 of the catheter. The targeted tissue T may be veins, myocardium or other cardiac tissue in which it is desirable to create a linear transmural lesion or ablation to alter electrical signal transmission in a treatment for atrial fibrillation as is known in the art. As shown in FIG. 26, the working end 400 is configured with a balloon 430 as is known in the art for positioning the working end in a treatment location. It is believed that the method of the invention can create the desired elongate linear thermal effect in the targeted tissue with greater control over (i) the lateral margins of the treatment path, and (ii) the depth of treatment, when compared to prior art radiofrequency devices that deliver Rf energy that courses through the tissue in an unpredictable manner.

Figure 27:
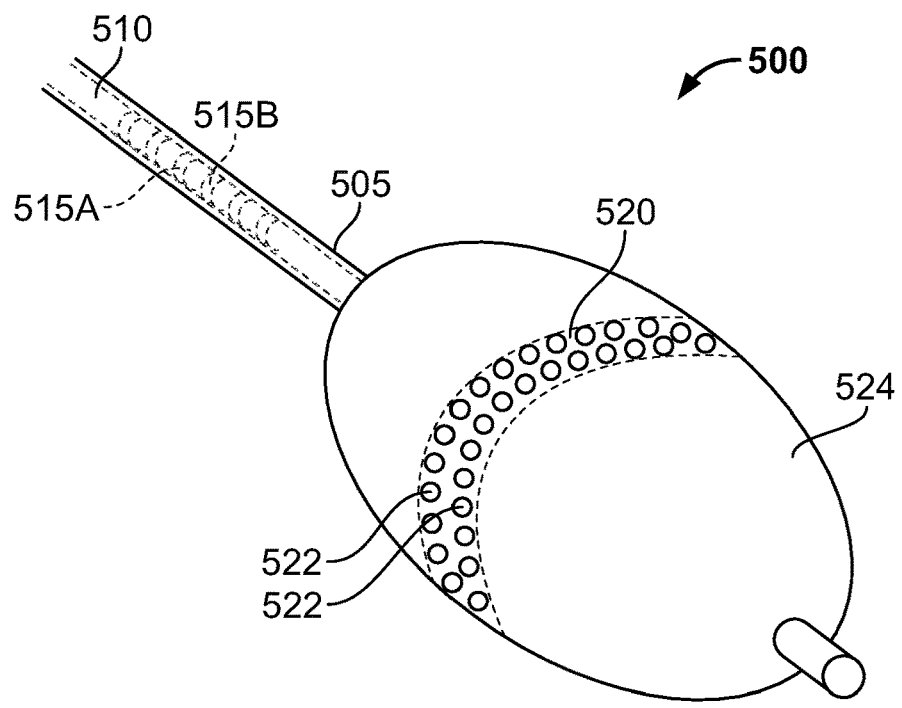
FIG. 27 is a perspective view of an alternative working end with apertures in the surface of an expandable structure.
Figure 28:
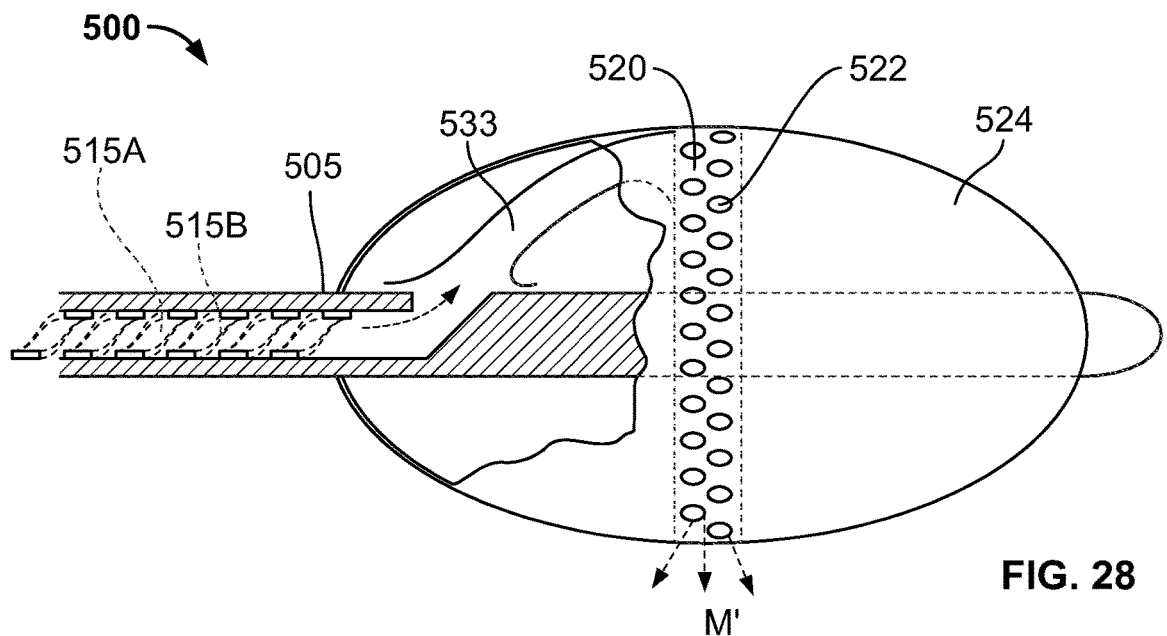
FIG. 28 is a cut-away view of the working end of a FIG. 27.

FIGS. 27 and 28 illustrate another embodiment of working end 500 for an endoluminal thermotherapy wherein the catheter body 505 carries interior chamber 510 and cooperating electrodes 515A and 515B (or a microchannel structure as in FIG. 12) for applying energy to inflowing liquid media M to cause it change in phase to vapor media M'. In this embodiment, the tissue-engaging surface 520 and outflow ports 522 are about the exterior of an expandable structure 524 that is distal to the interior chamber 510 and electrodes 515A and 515B. The interior chamber is coupled to the channel 525 by a flexible film lumen portion indicated at 533 in FIG. 28. The expandable structure 524 expands radially outward from the catheter axis to provide a linear, circumferential lesion. The outflow ports 522 are in the channel 525 formed in a temperature resistant laminate of the thin film polymer layers. The expandable structure can be an expandable balloon or mechanically actuated structure. In one embodiment as in FIGS. 27-28, the expandable structure 524 is a balloon of a non-distensible polymer that is expanded by a liquid that can be cooled to assist in controlled application of energy to tissue along the line of the outflow ports 522. The balloon inflation lumen is not shown for convenience. The working surface 520 can create circumferential lesions in pulmonary veins that are needed in treating atrial fibrillation—the most common form of cardiac arrhythmia (abnormal electrical signals in the heart), affecting more than 5 million people worldwide. It should be appreciated that the flex structure can be con configured about a deflectable working end of an instrument to engage about the exterior of a pulmonary vein for a pulmonary vein ablation treatment as is known in the art. The method of fabricating the flexible structure 524 is described below.

Figure 29:
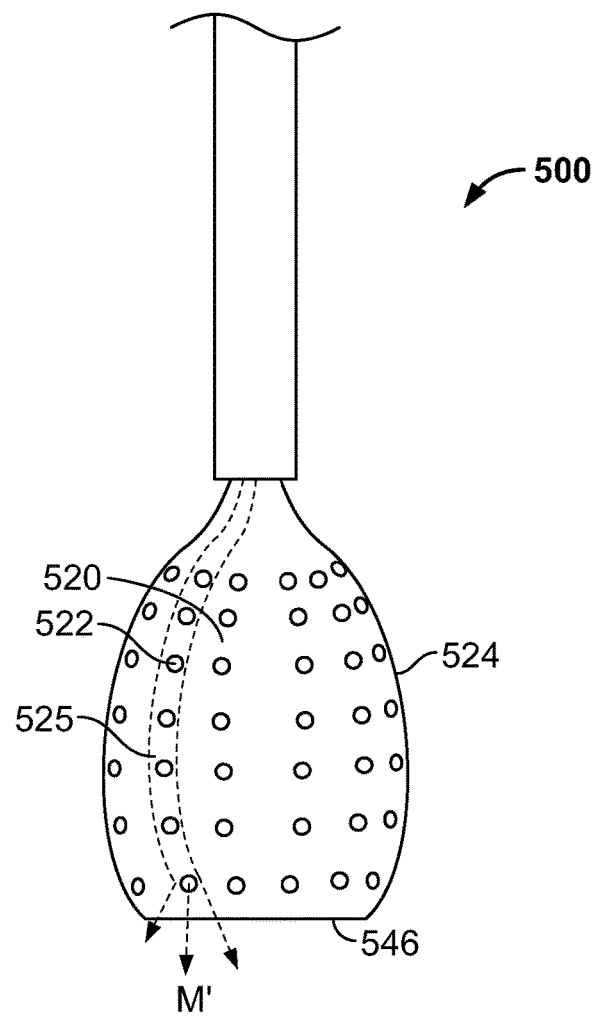
FIG. 29 is a plan view of an alternative working end with apertures in the surface of a thin-film structure for engaging and collapsing in a body cavity.

FIG. 29 illustrates another exemplary embodiment 500 with working surface 520 and inflow ports 522. This alternative flexible structure 524 is preformed for engaging the interior geometry of a lumen or cavity in any body structure or organ. The flexible structure 524 can be an expandable balloon, a structure expandable by any mechanical mechanism or a shape memory alloy or shape memory polymer, or an open web structure, for example expanded by gel infusion. Or the device as in FIG. 29 can have an open end 546 and be expanded to net shape of the structure as vapor media in pushed into channels 525 under pressure. The flexible structure 524 has a plurality if channels 525 with openings 522 therein to allow the exit a vapor phase media M' that is delivered under controlled pressure to the channels. The embodiment of FIG. 29, for example, can be used for applying energy to the wall 360 of an aneurysm. It should be appreciated that the flexible structure 524 also can take form of a highly elongate sleeve with perforations therein (not shown) for treating varicose veins. The flexible sleeve structure 524 would be inserted along the targeted length of the vein, and the openings in the sleeve would diffuse the delivery of vapor into all surfaces of the vessel. The ports 522 can be directed away from perforator vessels. Such a sleeve 524 can be releasable from the instrument and of a bioasorbable polymer. The sleeve can be left in place in the blood vessel. Such a device would be capable of directing high pressure flows in the desired direction and expand under inflow pressures of vapor media M'—and then collapse under the force of vessel shrinkage. The device would prevent thermal migration into perforators that extend between surface and deep vein systems.

Figure 30A:
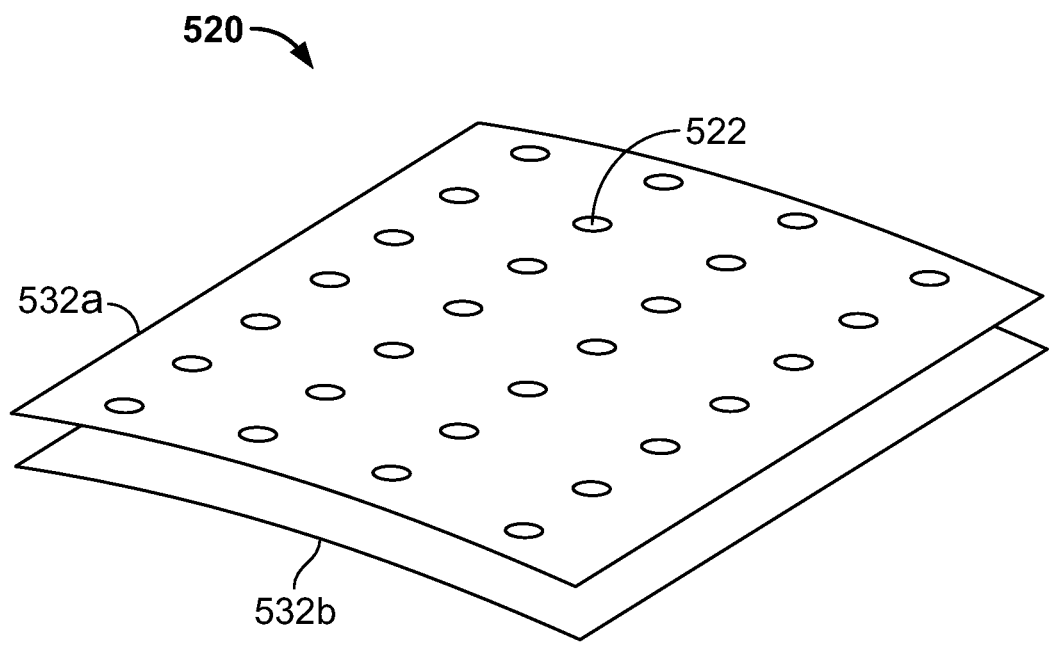
FIG. 30A is a view of a method of fabricating the thin-film structure of FIG. 29.
Figure 30B:
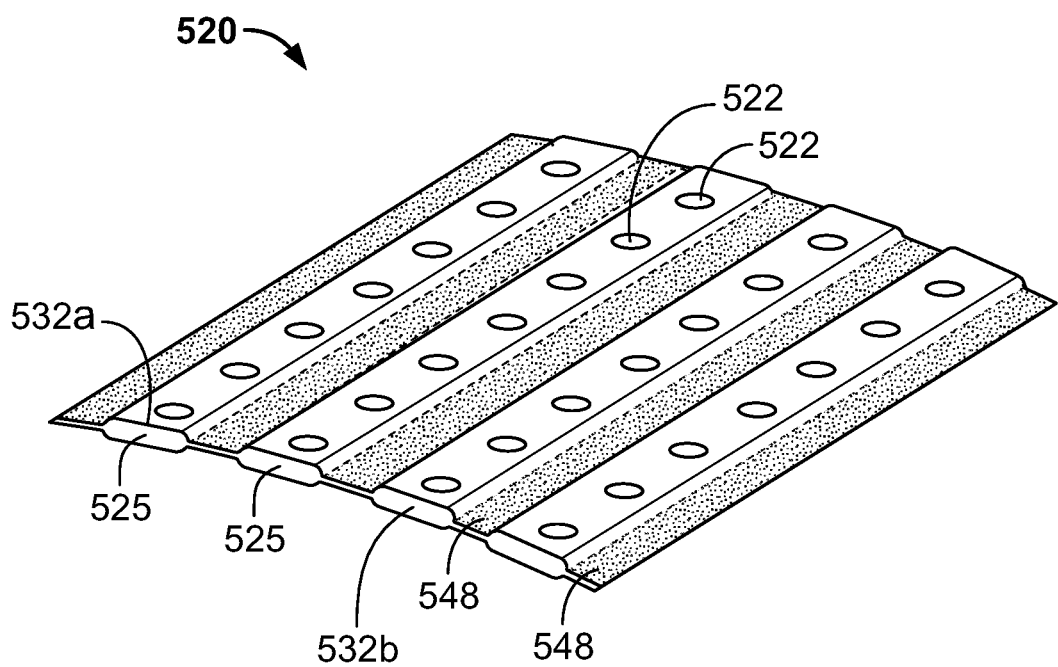
FIG. 30B is another view of a method of fabricating the thin-film structure of FIG. 29.

FIGS. 30A and 30B illustrate the method of making the expandable structure and working surface 520 of the device of FIG. 29. Thin film materials 532a and 532b of a temperature resistant material can be used and bonded (thermally or with adhesives etc.) along weld lines 548 to create channels 525. The openings or ports 522 can be laser cut or created in cooperating patterns by any suitable means. The ports and channel dimensions can have cross-sections (or branches) in controlled varied dimensions or shapes for causing a uniform outflow of vapor phase media M' along the length of an elongate channel.

Figure 31:
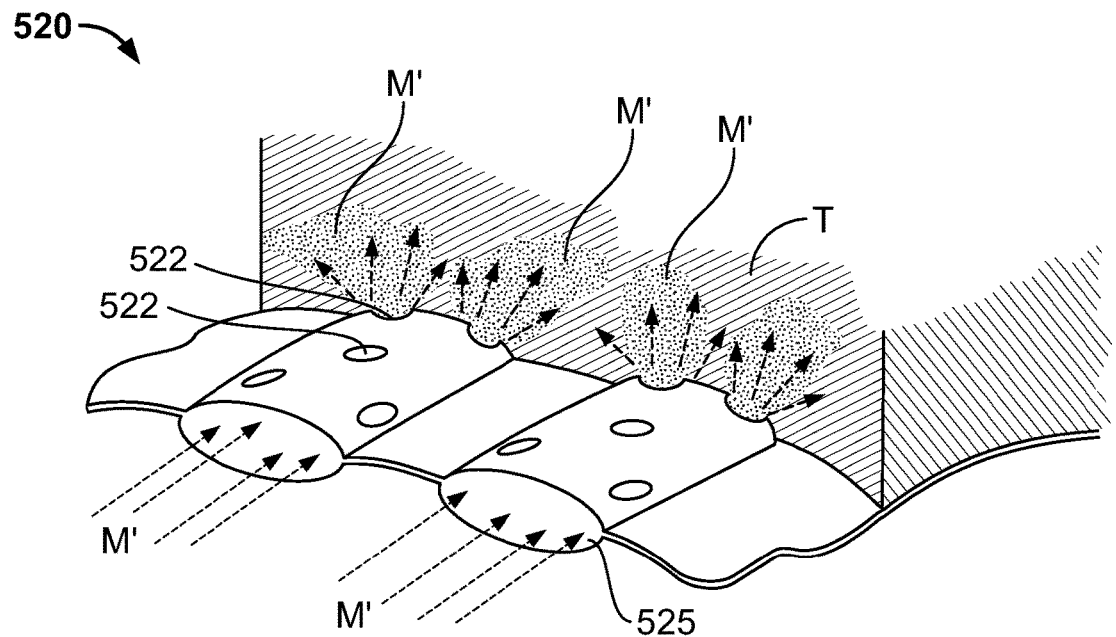
FIG. 31 illustrates the thermotherapy method utilizing the thin-film structure of FIG. 29.

FIG. 31 illustrates an exemplary cut-away view of a working surface 520 and channels 525 and further illustrating the release of the heat of vaporization to the engaged tissue in the vapor-to-liquid phase transition as vapor media exits ports 522. The tissue can be any interior of any body organ, such as a patient's uterus in an endometrial ablation treatment.

Figure 32A:
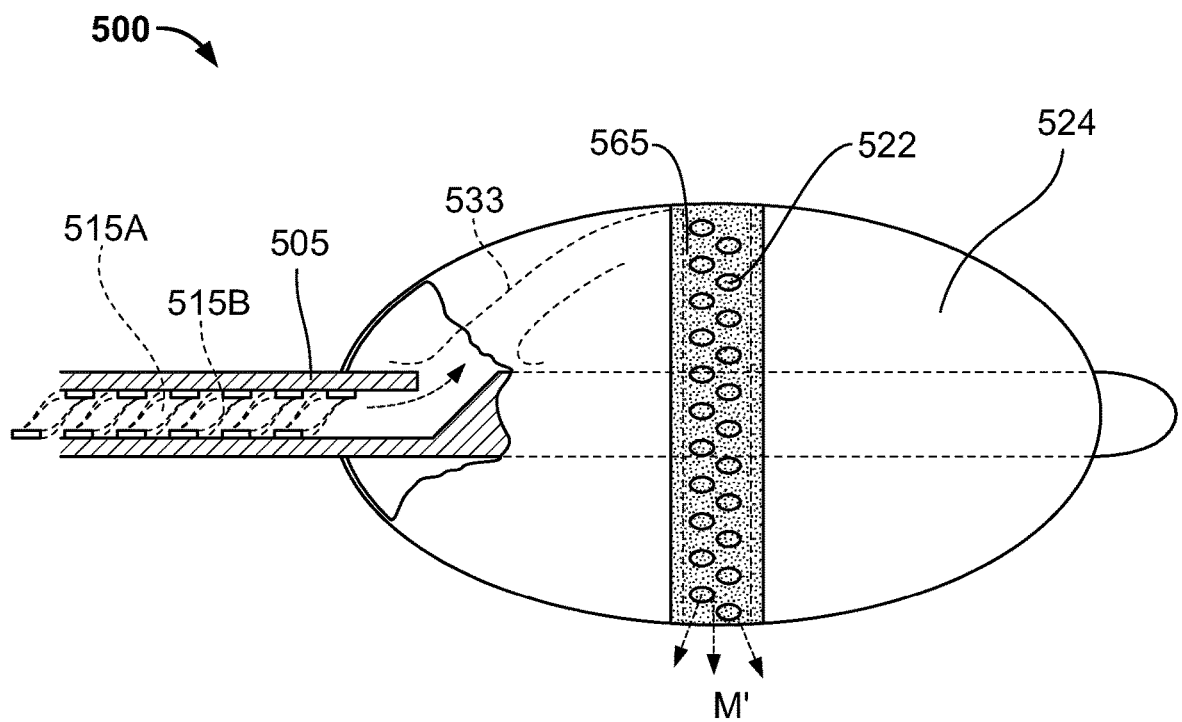
FIG. 32A is a plan view of an alternative working end.
Figure 32B:
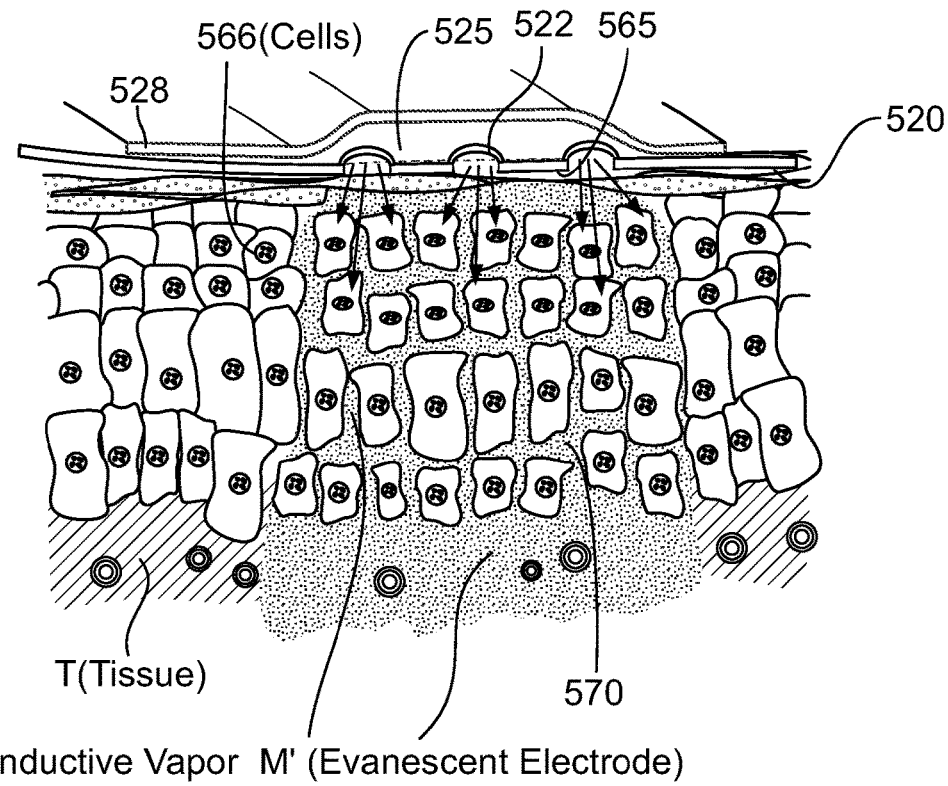
FIG. 32B depicts a greatly enlarged schematic view of the thin-film structure of FIG. 32A showing electrical energy delivery to conductive vapor media injected deep into a soft tissue volume.

FIG. 32A-32B illustrates an enhanced means of energy delivery to tissue from an expandable flex structure 524 similar to that depicted in FIGS. 27 and 31. The expandable structure 524 in FIG. 32A carries an additional conductive surface (electrode) layer indicated at 565 about the surface of the structure proximate the inflow ports 522. It should be appreciated that the conductive surface 565 can be provided in any working surface (or interior of any working surface) in the various embodiments described above. The conductive surface 565 is coupled to an electrical source and a controller but is adapted to function independently from, or in cooperation with, the electrical discharges that convert the liquid media to vapor media. Electrical energy delivery to surface electrode 565 can be intermittent a high Hz rate of energy delivery to the vaporizing electrodes 515A and 515B, or out of phase, for example. FIG. 32B is a schematic view of the method of the invention, showing a small portion of expandable structure 524 and channel 525 pressed against tissue. Vapor media M' is ejected under high pressure from ports 522 deep into tissue as depicted above in FIG. 31. The media is a high saline content solution that is vaporized in the instrument working end as described above and injected under high pressure into soft tissue T. It has been found that such vapor injection migrates in intracellular spaces between cells 566. The vapor media M' is also conductive (as it consists of a transient ionized plasma) as it extend very deep into soft tissue under the high pressure propagation before it condenses and delivers energy to tissue in the phase change release. At the time that the vapor media M' is with within the intracellular spaces 570, it can serve as a gas electrode (or evanescent electrode) that can conduct high voltage in cooperation with a ground pad until the vapor plume collapses. The method of the invention thus comprises applying voltage to the gas electrode (from conductive surface 565) within the intracellular spaces or deep tissue spaces to apply ablative energy to the tissue T. Thus, the phase transition energy release can be enhanced by energy delivery via the evanescent electrode means. This form of enhanced energy delivery will be uniform about the surface of the—in effect—gas electrode that evanesces (vanishes) leaving only dispersed water droplets. By these means, thermal ablation or shrinkage of vessel lumens or soft tissues can be accomplished very rapidly, under ultrasound visualization. In soft tissue applications, it has been found that the vapor media can be introduced deep into tissue volumes through intracellular fluid spaces to apply high energy densities throughout the targeted tissue volume. In effect, the evanescent electrode for micro-second or longer time scale extends throughout the tissue-not just contacting the tissue surface as is mono-polar or bi-polar Rf. While the method of applying electrical energy the conductive plasma or vapor is shown in soft tissue in FIG. 32B, the method applies equally to use in body lumens as in the treatment of varicose veins.

Figure 33:
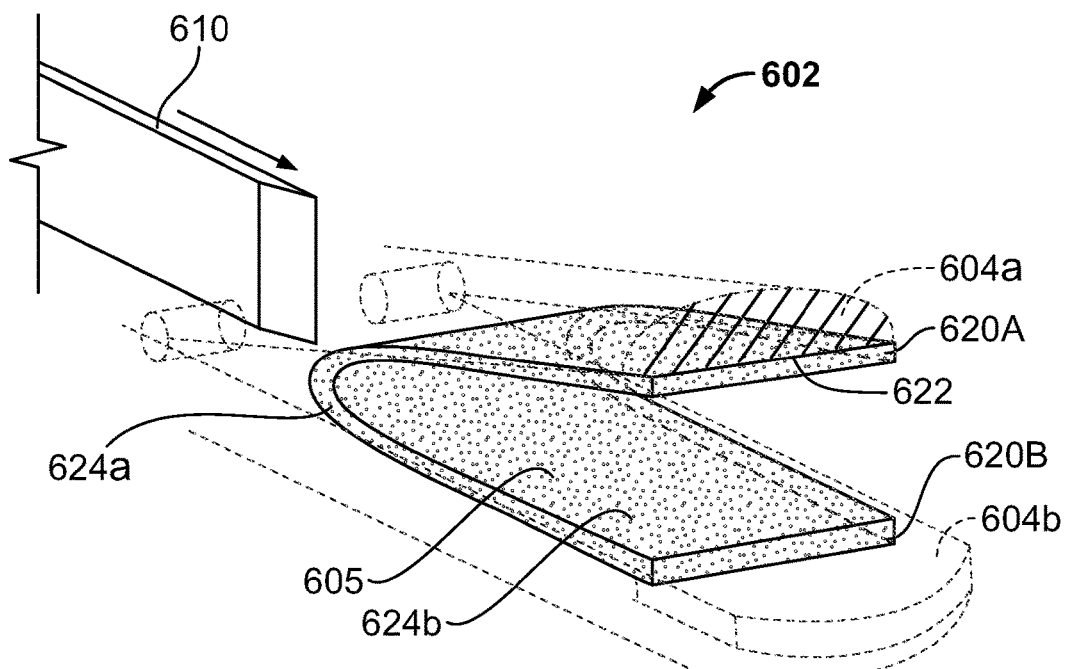
FIG. 33 is a schematic view of an alternative instrument working end for sealing/transecting tissue with a jaw structure that carries a releasable weldable polymer clip of a bioresorbable composition.

FIG. 33 illustrates an alternative working end 600 that comprises an openable-closeable jaw structure 602 with first and second jaws 604a and 604b that are moveable between a first open position and a second closed position to compress engaged tissue together with a releasable polymer clip-like element 605 carried within the jaws. The clip element 605 is adapted for providing sealing functionality in addition to the thermal sealing caused by energy delivery as described above. The sealed vessel also optionally can be transected with a blade 610 in the jaw structure 604 as in known in the art. In this working end, the jaw structure 602 carries a de-matable weldable clip of a heat shrinkable polymer or a similar shape memory polymer. Preferably, the clip 605 is biodegradable. In FIG. 33, the surfaces of one or both jaws comprise working surfaces 620A and 620B that have ports 622 therein from which vapor media M' is ejected under high pressure as described above. In one embodiment, the jaws carry opposing bi-polar electrodes or another heating elements to fuse together the ends 624a and 624b of clip 605 about the tissue. The polymer clip 605 is substantially porous for allowing vapor media M' to propagate directly through the polymer to interact with, and further seal the tissue.

Figure 34A:
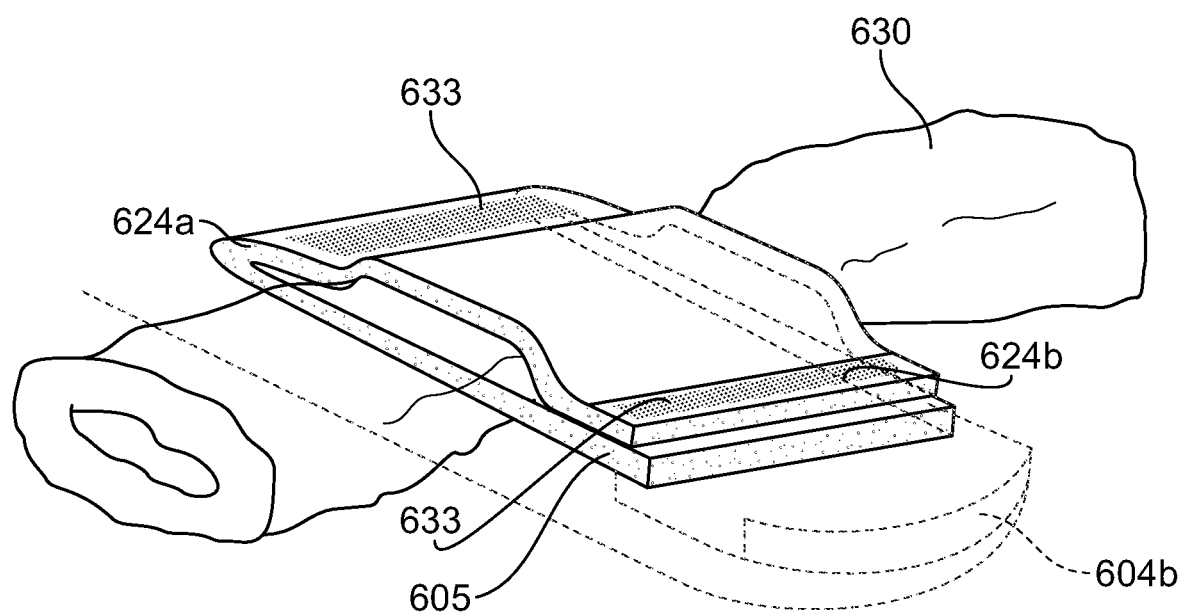
FIG. 34A is a schematic view of the working end and polymer clip of FIG. 33 depicting a first step in its method of use being clamped around a blood vessel and welded at the clip's free ends.
Figure 34B:
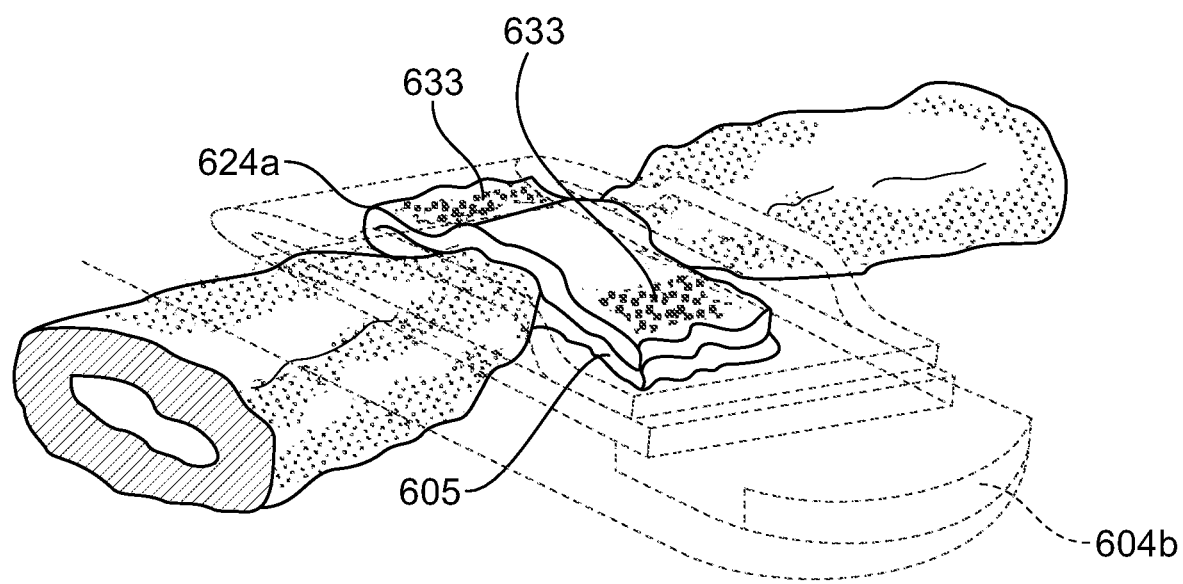
FIG. 34B is a schematic view of the polymer clip of FIG. 34A depicting the next step in its method of use wherein a vapor media is ejected through the polymer clip to seal the tissue and shrink the polymer.

FIG. 34A is a phantom view of jaw structure 602 (upper jaw not shown) clamping about a blood vessel 630 with the polymer clip 605 being compressed about the tissue. FIG. 34A also shows the ends 624a and 624b of clip 605 being welded at weld regions indicated at 633. FIG. 34B contemporaneously shows the method of shrinking the clip 620 wherein vapor media M' is ejected into the polymer clip from the jaws to seal the tissue while at the same time shrinking the biodegradable polymer within and about the captured tissue. The scope of the invention includes using the vapor media to melt and inject strands or webs of melted polymer through the captured tissue. Upon cooling, the polymer and tissue then form an integrated renatured composition for permanent sealing. It should be appreciated that the scope of the inventive clip extends to any form of energy delivery to shrink the clip, for example, Rf energy or laser energy. In one embodiment, the clip has projecting elements or barbs (not shown) to penetrate the tissue and any fascia to assist in vapor penetration into the captured tissue for more rapid delivery of thermal energy from the vapor to create a tissue seal. An instrument can be fabricated that carries a plurality of clips that can be advanced to the working end, much like a mechanical clip applier. The polymer clips also can carry imageable or radiopaque compositions.

Although particular embodiments of the present invention have been described above in detail, it will be understood that this description is merely for purposes of illustration. Specific features of the invention are shown in some drawings and not in others, and this is for convenience only and any feature may be combined with another in accordance with the invention. Further variations will be apparent to one skilled in the art in light this disclosure and are intended to fall within the scope of the appended claims.

I claim:

1. A method of ablating target tissue within a lumen in a patient's body, the method comprising:
    placing a working end of an elongate vapor delivery tool into the lumen;
    expanding at least one expandable member carried by the working end of the vapor delivery tool to place the at least one expandable member in contact with tissue; and
    delivering vapor from the working end of the vapor delivery tool to ablate the target tissue and to control a depth of the ablative treatment and a lateral margin of the ablative treatment.

2. The method of claim 1 wherein the placing step comprises inserting a catheter into the patient's body.

3. The method of claim 1 wherein the placing step comprises inserting an endoscope into the patient's body.

4. The method of claim 1 wherein the vapor comprises water vapor.

5. The method of claim 4 further comprising vaporizing liquid water prior to the delivering step.

6. The method of claim 1 further comprising condensing the vapor on the target tissue.

7. The method of claim 1 wherein the delivering step comprises delivering vapor to target tissue for 1-30 seconds.

8. The method of claim 1 wherein the delivering step comprises delivering vapor to target tissue for 5-20 seconds.

9. The method of claim 1 further comprising ablating target tissue in 360° around the lumen.

* * * * *